(12) United States Patent
Shulman et al.

(10) Patent No.: US 8,742,079 B2
(45) Date of Patent: Jun. 3, 2014

(54) SACCHARIDE-CONTAINING PROTEIN CONJUGATES AND USES THEREOF

(75) Inventors: Avidor Shulman, Rakefet-Doar-Na Misgav (IL); Ilya Ruderfer, Haifa (IL)

(73) Assignee: Protalix Ltd., Carmiel (IL)

( * ) Notice: Subject to any disclaimer, the term of this patent is extended or adjusted under 35 U.S.C. 154(b) by 254 days.

(21) Appl. No.: 12/673,987

(22) PCT Filed: Aug. 20, 2008

(86) PCT No.: PCT/IL2008/001143
§ 371 (c)(1),
(2), (4) Date: Feb. 18, 2010

(87) PCT Pub. No.: WO2009/024977
PCT Pub. Date: Feb. 26, 2009

(65) Prior Publication Data
US 2011/0105379 A1    May 5, 2011

Related U.S. Application Data

(60) Provisional application No. 60/935,587, filed on Aug. 20, 2007.

(51) Int. Cl.
| C07H 23/00 | (2006.01) |
| C07H 17/02 | (2006.01) |
| A61K 38/14 | (2006.01) |
| A01N 43/04 | (2006.01) |
| A61K 31/70 | (2006.01) |
| C07K 1/00 | (2006.01) |
| C07K 17/00 | (2006.01) |

(52) U.S. Cl.
USPC ........ 536/17.1; 536/17.9; 530/395; 514/20.9; 514/25

(58) Field of Classification Search
None
See application file for complete search history.

(56) References Cited

U.S. PATENT DOCUMENTS

| 5,580,757 A | 12/1996 | Desnick et al. |
| 5,595,756 A | 1/1997 | Bally et al. |
| 5,614,587 A | 3/1997 | Rhee et al. |
| 5,766,897 A | 6/1998 | Braxton |
| 5,994,086 A | 11/1999 | Benoff |
| 6,309,646 B1 * | 10/2001 | Lees ........................ 424/195.11 |
| 6,395,884 B1 | 5/2002 | Selden et al. |
| 6,846,968 B1 | 1/2005 | Erwin et al. |
| 7,011,831 B2 | 3/2006 | Calhoun et al. |
| 2002/0088024 A1 | 7/2002 | Garger et al. |
| 2002/0137125 A1 | 9/2002 | Zhu |
| 2003/0190304 A1 * | 10/2003 | Thompson et al. ........ 424/78.18 |
| 2005/0048047 A1 | 3/2005 | Kakkis |
| 2005/0058634 A1 * | 3/2005 | Zhu ........................... 424/94.61 |
| 2005/0059097 A1 | 3/2005 | Daunert et al. |
| 2005/0180948 A1 | 8/2005 | Desjarlais et al. |
| 2005/0282225 A1 | 12/2005 | Daunert et al. |
| 2006/0084163 A1 | 4/2006 | Schaffer et al. |
| 2006/0204487 A1 | 9/2006 | Shaaltiel et al. |
| 2006/0228348 A1 * | 10/2006 | Stefano ...................... 424/94.61 |
| 2012/0230974 A1 | 9/2012 | Shaaltiel et al. |

FOREIGN PATENT DOCUMENTS

| EP | 0747066 | 12/1996 |
| GB | 2402677 | 12/2004 |
| JP | 2005-043317 | 2/2005 |
| KR | 20070065157 | 6/2007 |
| WO | WO 91/14697 | 10/1991 |
| WO | WO 93/18148 | 9/1993 |
| WO | WO 95/01994 | 1/1995 |
| WO | WO 95/06478 | 3/1995 |
| WO | WO 96/23869 | 8/1996 |
| WO | WO 97/10353 | 3/1997 |
| WO | WO 98/13469 | 4/1998 |
| WO | WO 01/25277 | 4/2001 |
| WO | WO 02/057435 | 7/2002 |
| WO | WO 03/035686 | 5/2003 |
| WO | WO 03/042244 | 5/2003 |
| WO | WO 03/090695 | 11/2003 |
| WO | WO 03/097791 | 11/2003 |
| WO | WO 2004/081053 | 9/2004 |
| WO | WO 2004/091475 | 10/2004 |
| WO | WO 2004/096978 | 11/2004 |
| WO | WO 2004/111198 | 12/2004 |
| WO | WO 2005/056760 | 6/2005 |
| WO | WO 2005/077093 | 8/2005 |
| WO | WO 2005/093422 | 10/2005 |
| WO | WO 2006/093524 | 9/2006 |
| WO | WO 2006/108052 | 10/2006 |
| WO | WO 2007/010533 | 1/2007 |
| WO | WO 2008/012540 | 1/2008 |
| WO | WO 2008/075957 | 6/2008 |
| WO | WO 2008/089403 | 7/2008 |
| WO | WO 2008/132743 | 11/2008 |
| WO | WO 2009/024977 | 2/2009 |
| WO | WO 2010/004568 | 1/2010 |
| WO | WO 2011/107992 | 9/2011 |
| WO | WO 2012/098537 | 7/2012 |

OTHER PUBLICATIONS

Yamaguchi et al. Biomacromolecules 2005, 6, 1921-1930.*
Communication Relating to the Results of the Partial International Search Dated Sep. 18, 2009 From the International Searching Authority Re.: Application No. PCT/IL2008/001143.
International Preliminary Report on Patentability Dated Mar. 4, 2010 From the International Bureau of WIPO Re.: Application No. PCT/IL2008/001143.
International Search Report and the Written Opinion Dated Nov. 23, 2009 From the International Searching Authority Re.: Application No. PCT/IL2008/001143.

(Continued)

*Primary Examiner* — Layla Bland

(57) ABSTRACT

Conjugates of a saccharide and a biomolecule, covalently linked therebetween via a non-hydrophobic linker and methods of preparing same are disclosed. Also disclosed are medical uses utilizing such conjugates. Glycosylation reagents for use in preparing these conjugates are also disclosed. Glycosylated proteins, characterized by improved performance, are also disclosed.

43 Claims, 29 Drawing Sheets
(18 of 29 Drawing Sheet(s) Filed in Color)

(56) References Cited

OTHER PUBLICATIONS

Benoff et al. "Use of Mannose Ligands in IVF Screens to Mimic Zona Pellucida-Induced Acrosome Reactions and Predict Fertilization Success", Molecular Human Reproduction, XP002554818, 3(10): 839-846, Oct. 1997. Abstract.
Fernandez-Megia et al. "Conjugation of Bioactive Ligands to PEG-Grafted Chitosan at the Distal End of PEG", Biomacromolecules, XP002554819, 8(3): 833-842, Mar. 2007.
Grosse et al. "Intracellular Rate-Limiting Steps of Gene Transfer Using Glycosylated Polylysines in Cystic Fibrosis Airway Epithelial Cells", Gene Therapy, XP002554817, 9(15): 1000-1007, Aug. 2002. p. 1005, col. 1, § 4.
Laville et al. "Photodynamic Efficiency of Diethylene-Linked Glycoconjugated Porphyrins in Human Retinoblastoma Cells", Journal of Medicinal Chemistry, XP002554822, 49(8): 2558-2567, Apr. 2006. Figs.1-3.
Li et al. "Bacteria Targeted by Human Natural Antibodies Using α-Gal Conjugated Receptor-Specific Glycopolymers", Bioorganic and Medicinal Chemistry, XP002554821, 7(8): 1549-1558, Aug. 1999. Figs. 1-5.
Lindhorst et al. "Trivalent α-D-Mannoside Clusters as Inhibitors of Type-1 Fimbriae-Mediated Adhesion of *Escherichia coli*: Structural Variation and Biotinylation", Journal of the chemical Society, Perkin Transactions 1, XP002554820, 8: 823-831, Apr. 21, 2001.
Rathnam et al. "Conjugation of A Fetuin Glycopeptide to Human Follicle-Stimulating Hormone and Its Subunits by Photoactivation", Biochimica et Biophysica Acta, XP002554815, 624(2): 436-442, 1980. Fig. 1.
Schottelius et al. "Detection and Quantitation of Cell-Surface Sugar Receptor(s) of Leishmania Donovani by Application of Neoglycoenzymes", Parasitology Research, XP008114350, 78(6): 529-533, 1992.
Takahashi et al. "A New Method for the Formation of the α-Glycose Bond of Sialyl Conjugates Based on Long-Range Participation", Tetrahedron Letters, XP004094811, 38(47): 8223-8226, Nov. 14, 1997. Fig.2, Compound 9.
Takahashi et al. "Design and Synthesis of a Water-Soluble Taxol Analogue: Taxol-Sialyl Conjugate", Bioorganic & Medicinal Chemistry Letters, XP004136633, 8(1-6): 113-116, Jan. 6, 1998. Fig.1, Compounds 1, 2.
Zambrano et al. "Receptor Binding Activity and In Vitro Biological Activity of the Human FSH Charge Isoforms as Disclosed by Heterologous and Homologous Assay Systems. Implications for the Structure-Function Relationship of the FSH Variants", Endocrine, XP002554816, 10(2): 113-121, 1999. p. 114, col. 1, § 2, Fig.l.
Communication Pursuant to Article 94(3) EPC Dated Oct. 7, 2010 From the European Patent Office Re. Application No. 08789815.1.
Response Dated Feb. 3, 2011 to Communication Pursuant to Article 94(3) EPC of Oct. 7, 2010 From the European Patent Office Re. Application No. 08789815.1.
Li et al. "Bacteria Targeted by Human Natural Antibodies Using α-Gal Conjugated Receptor-Specific Glycopolymers", Bioorganic and Medicinal Chemistry, XP002554821, 7(8): 1549-1558, Aug. 1999. Figs.1-5.
Takahashi et al. "A New Method for the Formation of the α-Glycose Bond of Sialyl Conjugates Based on Long-Range Participation", Tetrahedron Letters, XP004094811, 38(47): 8223-8226, Nov. 24, 1997. Fig.2, Compound 9.
Communication Relating to the Results to the Partial International Search Dated Jul. 4, 2011 From the International Searching Authority Re. Application No. PCT/IL2011/000211.
International Preliminary Report on Patentability Dated Sep. 13, 2012 From the International Bureau of WIPO Re. Application No. PCT/IL2011/000209.
International Preliminary Report on Patentability Dated Sep. 13, 2012 From the International Bureau of WIPO Re. Application No. PCT/IL2011/000210.
International Preliminary Report on Patentability Dated Sep. 13, 2012 From the International Bureau of WIPO Re. Application No. PCT/IL2011/000211.
International Preliminary Report on Patentability Dated May 31, 2012 From the International Bureau of WIPO Re. Application No. PCT/IL2010/000956.
International Search Report and the Written Opinion Dated Feb. 2, 2012 From the International Searching Authority Re. Application No. PCT/IL2011/000719.
International Search Report and the Written Opinion Dated Mar. 14, 2011 From the International Searching Authority Re. Application No. PCT/IL2010/000956.
International Search Report and the Written Opinion Dated Jun. 22, 2011 From the International Searching Authority Re. Application No. PCT/IL2011/000210.
International Search Report and the Written Opinion Dated Jun. 24, 2011 From the International Searching Authority Re. Application No. PCT/IL2011/000209.
International Search Report and the Written Opinion Dated Sep. 28, 2011 From the International Searching Authority Re. Application No. PCT/IL2011/000211.
Buckmann et al. "Functionalization of Poly(Ethylene Glycol) and Monomethoxy-Poly(Ethylene Glycol)", Die Makromolekulare Chemie, 182(5): 1379-1384, May 1981.
Buckmann et al. "Synthesis of Water Soluble Polymers With Covalently Bound General Ligands", Enzyme Engineering, 4: 395-397, 1978.
Bendele et al. "Short Communication: Renal Tubular Vacuolation in Animals Treated With Polyethylene-Glycol-Conjugated Proteins", Toxicological Sciences, 42: 152-157, 1998.
Chen et al. "Directed Evolution of A Lysosomal Enzyme With Enhanced Activity at Neutral pH by Mammalian Cell-Surface Display", Chemistry and Biology, 15: 1277-1286, 2008.
Cramer et al. "Transgenic Plants for Therapeutic Proteins: Linking Upstream and Downstream Strategies", Current Topics in Microbiology and Immunology, XP009038354, 240(3): 95-118, 1999.
Den Dulk-Ras et al. "Electroporation of *Agrobacterium tumefaciens*", Methods in Molecular Biology, 55: 63-72, 1995. Abstract.
Gao et al. "A Novel Alkaline ?-Galactosidase From Melon Fruit With a Substrate Preference for Raffinose", Plant Physiology, XP002128580, 119(3): 979-987, Mar. 1, 1999. Abstract, p. 980-981: "Alkaline ?-Galactosidase Purification".
Gleba et al. "Magnifection—A New Platform for Expressing Recombinant Vaccines in Plants", Vaccine, 23: 2042-2048, 2005.
Hoffmann "Fabry Disease: Recent Advances in Pathology, Diagnosis, Treatment and Monitoring", Orphanet Journal of Rare Diseases, 4(21): 1-9, Oct. 11, 2009.
Kapoor "How to Cross-Link Proteins", FGSC (Fungal Genetics Stock Center), University of Missouri, MO, USA, p. 1-6, Mar. 28, 2006. Retrieved From the Internet.
Neumann et al. "Protein Transport in Plant Cells: In and Out of the Golgi", Annals of Botany, 92: 167-180, 2003.
Pagny et al. "Signals and Mechanisms for Protein Retention in the Endoplasmic Reticulum", Journal of Experimental Botany, 50(331): 157-164, Feb. 1999.
Potrykus "Gene Transfer to Plants: Assessment of Public Approaches and Results", Annual Review of Plant Physiology & Plant Molecular Biology, 42: 205-225, 1991.
Rayon et al. "The Protein N-Glycosylation in Plants", Journal of Experimental Botany, 49(326): 1463-1472, Sep. 1998.
Shimamoto et al. "Fertile Transgenic Rice Plants Regenerated From Transformed Protoplasts", Nature, 338: 274-276, Mar. 16, 1989.
Sigma-Aldrich "Innovations in Peptide Synthesis and Conjugation: Tools for Drug Discovery", ChemFiles, 5(12): 1-24, 2005.
Tardi et al. "Liposomal Encapsulation of Topotecan Enhances Anticancer Efficacy in Murine and Human Xenograft Models", Cancer Research, 60: 3389-3393, 2000.
Thermo Fisher Scientific "Instructions BM(PEG)2 and BM(PEG)3", Thermo Fisher Scientific Inc., Pierce Biotechnology, Rockford, IL, USA, 3 P., 2007.
Thermo Fisher Scientific "Instructions BS(PEG)n. Homofunctional, Amine-Reactive Crosslinkers With Polyethylene Glycol (PEG) Spacer Arms", Thermo Fisher Scientific Inc., Pierce Biotechnology, Rockford, IL, USA, 3 P., 2008.

(56) References Cited

OTHER PUBLICATIONS

UniProt "Name-ERABP1; OrderedLocusNames=At4g02980; ORFNames=T4I9.14; *Arabidopsis thaliana* (Mouse-Ear Cress)", UniProtKB / Swiss-Prot, ID ABP1_ARATH, Accession No. P33487, Feb. 1, 1994.

Vamvakaki et al. "Fluorescence Detection of Enzymatic Activity Within a Liposome Based Nano-Biosensor", Biosensors and Bioelectronics 21: 384-388, 2005.

Vargas et al. "Endocytosis of Liposomes Containing Lyposomal Proteins Increases Intracellular Protein Degradation in growing L-132 Cells", European Journal of Biochemistry, 188:99-109, 1990.

Examination Report Dated Feb. 28, 2013 From the Australian Government, IP Australia Re. Application No. 2008290217.

Office Action Dated Mar. 11, 2013 From the Israel Patent Office Re. Application No. 204037 and Its Translation Into English.

Pierce "Crosslinking Reagents", The Pierce Technical Handbook, 48 P, 2006.

\* cited by examiner

SACCHARIDE-CONTAINING PROTEIN CONJUGATES AND USES THEREOF

RELATED APPLICATIONS

This Application is a National Phase of PCT Patent Application No. PCT/IL2008/001143 having International filing date of Aug. 20, 2008, which claims the benefit of U.S. Provisional Patent Application No. 60/935,587 filed on Aug. 20, 2007. The contents of the above Applications are all incorporated herein by reference.

FIELD AND BACKGROUND OF THE INVENTION

The present invention, in some embodiments thereof, relates to saccharide-containing active reagents (e.g., glycosylation agents), to conjugates thereof with biomolecules and to methods utilizing these conjugates in e.g., therapeutic applications. More particularly, but not exclusively, the present invention, in some embodiments thereof, relates to saccharide-containing active reagents (e.g., glycosylation agents), to protein conjugates made therefrom and to methods utilizing these protein conjugates in therapeutic applications.

The trafficking of many proteins, and especially lysosomal enzymes, to their target organs, cells and organelles is controlled and enabled by different carbohydrate-specific receptors, such as the mannose or mannose-6-phosphate (M6P) receptors.

In order for proteins to be recognized and transported by carbohydrate-specific receptors, the proteins should be glycosylated with oligosaccharide residues terminating with the appropriate carbohydrate moiety. This is especially important in therapeutic proteins which should be transported to their action site in order to exert their therapeutic benefits.

Of particular importance are the mannose-6-phosphate receptors. The biogenesis of lysosomes, which are key components of the degradative machinery of eukaryotic cells, requires the action of the mannose-6-phosphate receptors (MPRs). Two MPRs, the 300-kDa cation-independent MPR (CI-MPR) and the 46-kDa cation-dependent MPR (CD-MPR), participate in the intracellular delivery of 50 different lysosomal enzymes to the lysosome by diverting these soluble acid hydrolases from the secretory pathway and delivering them from the trans Golgi network to endosomal compartments. The CI-MPR has also been shown to function in the binding and internalization of ligands at the cell surface. The higher capacity of the CI-MPR as compared with the CD-MPR in sorting lysosomal enzymes to the lysosome is due in part to the ability of the CI-MPR at the cell surface to re-capture lysosomal enzymes that may have been secreted, resulting in their internalization and delivery to endosomal compartments.

In addition to lysosomal enzymes, the repertoire of extracellular M6P-containing ligands has expanded in recent years to include a diverse spectrum of proteins including the precursor form of transforming growth factor and renin, proliferin, granzymes A and B, CD26, and herpes simplex viral glycoprotein D. Several studies have implicated the interaction of these ligands with the CI-MPR at the cell surface as being essential to their activity and/or function, thus expanding the role of the CI-MPR from solely an intracellular protein carrier to a cell surface signaling molecule via its lectin activity.

Oligosaccharides containing M6P have been isolated from lysosomal enzyme mixtures from human skin fibroblasts, mouse lymphoma cells, murine macrophages, and from purified lysosomal enzymes including β-glucuronidase and β-galactosidase. The results of structural analyses indicated that α(1,2)-linked M6P residues are present as terminal or penultimate residues on either, or both, antennary arms of N-linked oligomannosides. In addition, some M6P residues contain N-acetylglucosamine in phosphodiester linkage. The binding properties of the oligomannosides obtained from acid hydrolases have been examined by affinity chromatography on immobilized CI-MPR and CD-MPR. The immobilized receptors bind oligomannosides containing two M6P residues with a greater affinity than those containing a single M6P residue.

As mentioned above, the glycosylation profile of a protein determines its bio-availability and trafficking behavior. The glycosylation profile of a specific protein is highly dependent on its biosynthetic pathway and its expressing platform. Thus, recombinant therapeutic proteins, expressed in various expressing platforms, including bacteria, fungi, plants, and mammalian cells, almost always differ dramatically in their glycosylation sites, glycosylation level and oligosaccharide profile from the original human protein. These differences dramatically diminish the bioavailability and uptake of the recombinant protein by the target cells, resulting in diminished therapeutic potency or necessitating higher doses.

For example, recombinant lysosomal enzymes obtained from different expression systems are often not sufficiently phosphorylated and the level of M6P in the oligosaccharides varies considerably from one expression system to another. The high uptake form of α-galactosidase A is bis-phosphorylated while only 20% of the α-galactosidase A expressed in CHO cells are phosphorylated and only 5% are bis-phosphorylated. Moreover, recombinant proteins expressed in plants, insect cells or yeasts do not have any M6P phosphorylation since these expression systems lack the M6P targeting pathway.

In view of the need to enable the targeting of recombinant therapeutic proteins, and especially of plant recombinant proteins, to carbohydrate-specific receptors, such as the M6P receptor, a few methodologies have been devised to conjugate M6P to proteins, as follows.

U.S. Pat. No. 7,001,994 teaches oxidizing protein glycosides to carbonyls (aldehydes) and reacting these carbonyls with phosphorylated mannopyranosyl oligosaccharides. The phosphorylated mannopyranosyl saccharides are derivatized with a carbonyl reactive substituent, such as hydrazine, which upon reaction with the aldehydes yields a covalent hydrazone bond. This methodology was also exemplified by Cheng et al. (Abstracts of Papers, 232nd ACS National Meeting, San Francisco, Calif., United States, Sep. 10-14, 2006) by attaching a synthetic oligosaccharide ligand bearing M6P residues in the optimal configuration for binding the CI-MPR. In this methodology, the protein undergoes oxidative conditions which are not selective and may cause oxidative damage to additional sites on the protein, including active sites. Such oxidative damage may also promote oxidative stress upon administration.

Beljaars et al. (*Liver* 2001, 21, 320-328) have synthesized M6P-modified albumin ($M6P_{28}$-HSA) in order to improve targeting of drugs to hepatic stellate cells. In this publication, it has been shown that the binding of M6P-HSA to the M6P/IGFII receptor is specific. Furthermore, $M6P_{28}$—HSA was extensively internalized by these cells. Using monensin, a specific inhibitor of the lysosomal pathway, proof was obtained that M6P-HSA is endocytosed via this route. Beljaars et al. have concluded that $M6P_{28}$—HSA is applicable as a stellate cell-selective carrier for antifibrotic drugs that act intracellularly. The M6P was connected to the albumin protein by phosphorylating p-nitrophenyl-α-D-mannopyranoside, and further reducing the nitro-group to the primary amine. The latter could be coupled to proteins by two methodologies: In the first methodology the p-aminophenyl-sugar was reacted with sodium nitrite under acidic conditions to form the diazonium salt of the derivatized sugar. This diazonium salt readily binds covalently to tyrosine or histidyl residues on the protein. In another optional methodology the p-aminophenyl-sugar is treated with thiophosgen to convert the primary amine to an isothiocyanate group, the latter readily reacts with primary amino groups on the protein, primarily lysine residues.

In a different methodology (see, U.S. patent application Ser. No. 10/024,197) a phosphorylated glucocerebrosidase has been prepared while utilizing isolated GlcNAc phosphotransferase and a phosphodiester α-GlcNAcase. According to this methodology, which mimics natural biosynthetic mechanisms, both enzymes used in the phosphorylation protocol should be produced and isolated, rendering this methodology cumbersome, cost-ineffective and laborious, necessitating the purification of the therapeutic protein from the additional enzymes used in its post-translational modification.

Lee et al. (*Glycoconjugate Journal* 2006, 23 (5/6), 317-327) have conjugated galactose-6-phosphate (Gal6P) to bovine serum albumin by using glycosides of Gal6P that can potentially generate a terminal aldehyde group, namely Gal6P with a glycerol attached to its anomeric carbon. ω-Aldehydro glycosides were then conjugated to BSA via reductive amination.

Hydrocarbon chains have been used as linkers to oligosaccharides in different biological studies. In WO 92/22662, oligosaccharides having attached thereto an 8-methoxycarbonyloctyl [—(CH$_2$)$_8$CO$_2$CH$_3$] group, and use thereof in a variety of biological applications are taught. This publication also teaches that a PEG chain can be used as the linker.

Distler et al. (*J. Biol. Chem.* 1991, 266, 21687) have also used an 8-methoxycarbonyloctyl alkyl linker to show the binding specificity of different phosphorylated mannose glycosides to MPR. A series of chemically synthesized oligomannosides that contain M6P residues were utilized as inhibitors of the binding of β-galactosidase to CI-MPR and CD-MPR in order to probe the specificity of each receptor.

Tomoda et al. (*Carbohydrate Research* 1991, 213, 37-46) have also studied the binding of bovine serum albumin (BSA) derivatized with penta-D-mannose-6-phosphate and have established that the best binding was obtained when the linkage mode between the terminal M6P sugar group and the penultimate sugar residue was α(1→2). Furthermore, they have shown that the length of the sugar chain also affects the binding to the M6P receptor, such that, for example, trisaccharides containing a terminal M6P group were more potent inhibitors than disaccharides.

JP 04210221 describes long chain alkyl D-glucoside-6-phosphates as surfactants for dishwashing and shampoos.

Cowden et al. (U.S. Pat. No. 6,294,521) describe the preparation of sugar phosphates as anti-inflammatory agents. D-mannoside-6-phosphate derivatives wherein the anomeric carbon is derivatized with a long chain hydrocarbon (C$_8$-C$_{16}$) are used in treating inflammatory diseases, particularly cell-mediated inflammatory diseases.

Similar glucose-6-phosphate derivatives have been described by Jones et al. (*Journal of the Chemical Society, Chemical Communications* 1994, 11, 1311-12). Dodecyl β-D-glucopyranoside-6-phosphate was used as a novel surfactant possessing a long-chain hydrocarbon tail and a hydrophilic head, consisting of a phosphoryl group covalently linked to a (homochiral) glucose moiety. This compound has been successfully used in miscellar electrokinetic capillary chromatography.

Short PEG chains (n=3) attached at one end to the anomeric carbon of a monosaccharide in a β-conformation and to a fatty acid at the other end are used as detergents in various pharmaceutical and cosmetic applications (see, for example, JP 2766141, JP 2854203, JP 06080686, WO 2006/098415). These publications suggest that such detergents (for example, saccharide-(OCH$_2$CH$_2$)$_3$—NH—CO—CH(C$_{16}$H$_{33}$)$_2$) can be used in the preparation of drug delivery systems, mainly liposomes, in combination with other lipids, such as cholesterol and glycerophospholipids.

Similar detergents, which were further used as anchored cryo-protectors, have been prepared by Wilhelm et al. (*Liebigs Annalen* 1995, 9, 1673-9), using long-chain alcohols (C$_{16}$) with 0-4 ethoxy spacers. Engel et al. (*Journal of Pharmaceutical Sciences* 2003, 92(11), 2229-2235) have used the same detergents in the creation of liposomes and have evaluated the interaction of mannose and glucose derivatives of these detergents with Concanavalin A lectin. Engel et al. (*Pharmaceutical Research* 2003, 20 (1), 51-57) have also improved the uptake of such mannosyl-based liposomes by macrophages, by enhancing the affinity towards mannose receptor. The researchers have suggested that such mannosides with sufficiently long spacer arms are of potential use in receptor-mediated targeting of liposomes made with such detergents.

Millqvist-Fureby et al. have described (*Biotechnology and Bioengineering* 1998, 59(6), 747-753) the synthesis of ethoxylated glycosides (tetraethylene glycol β-D-glucoside, tetraethylene glycol β-D-xyloside, and methoxy triethyleneglycol β-D-glucoside). These were in turn used as raw materials for the preparation of the above discussed detergents, bearing an additional fatty acid, such as ω-O-oleoyl tetraethylene glycol β-D-glucoside.

These glycoside-PEG-fatty acid detergents were widely investigated for their physical properties (Czichocki et al. *Journal of Chromatography, A* 2002, 943(2), 241-250; Zimmermann et al. Spectroscopy of Biological Molecules: New Directions, European Conference on the Spectroscopy of Biological Molecules, 8th, Enschede, Netherlands, Aug. 29-Sep. 2, 1999 (1999), 353-354) as well as in various applications, such as biofilm inhibitory and removal agents (JP 2006347941) and for anticaries dentifrices (WO 2006/035821).

PEGylated glycosides, in which the glycosides are conjugated to a small number of ethylene glycol groups, are commercially available although not wide-spread. These glycoside-PEG derivatives are composed of short-chain PEGs (n≤4) and are mainly used to create the surfactants described above by their further conjugation to a hydrophobic moiety, such as a fatty acid.

WO 2005/093422 describes the use of bio-functionalized quantum dots comprising a saccharide derivatized at the anomeric carbon in a β-conformation with a PEG chain (n=6) derivatized at the other end with an alkyl thiol group. These bio-functionalized quantum dots can be used in biological and medical research, imaging and/or therapy applications.

JP 3001381 discloses the use of monosaccharides linked to a PEG chain or an alkyl chain, and further linked to a polysaccharide, such as chitosan, a pullulan, a dextran, mannoglucan, heparin or hyaluronic acid. These moieties were used for delivering drugs following their physical incorporation in the matrices of these polysaccharides, similarly to liposomes.

Andersson et al. (*Glycoconjugate Journal* 1993, 10(3), 197-201) have prepared glycosides with a linker of a short PEG chain (n=2 or 4) attached to the anomeric carbon (β-conformation). These glycosides were conjugated to proteins through a terminal activated ester. The target application of such glycoside-protein conjugates is as antigens in diagnostic tests or as immunogens. While conjugation with monosaccharides is described, these studies were mainly practiced with oligosaccharides. The PEG linker in all the practiced conjugates was connected to the glycoside via an equatorial bond (β conformation). As noted above, the PEG chains used in this work were relatively short (n=2 or 4).

Biskup et al. (*ChemBioChem* 2005, 6(6), 1007-1015) have used glycoside with short PEG spacers (n=4) for immobilization of the glycoside onto solid surfaces, followed by interacting the immobilized glycosides with lectins. It appears that the PEG spacers in the studied conjugates were attached to the glycoside anomeric carbon in the β conformation.

Zalipsky et al. (*Chemical Communications (Cambridge)* 1999, 7, 653-654) have presented a practical approach for preparing galactose-PEG-distearoylphosphatidic acid (DSPA) that retains full lectin binding. Their methodology involved glycosylation of monobenzyl ether-PEG, suitable protection of the sugar hydroxy groups, and debenzylation, followed by enzymatic transphosphatidylation with phosphatidylcholine and final deprotection.

WO 2006/093524 describes compositions comprising antigen-carbohydrate conjugates and methods of immune modulation utilizing these reagents. Thus, ovalbumin, a model antigen, was reacted with the N-hydroxy-succinimide (NHS) group of a bi-functional short hydrocarbon linker to introduce maleimide functional groups. The latter were then reacted with thiol-terminated short PEG chains (n=2-3) attached to saccharides. These saccharides comprise monosaccharides, but mainly high-mannose oligosaccharide. These conjugates were shown to enhance antigen uptake and presentation to T cells, when compared to unmodified ovalbumin. This, in turn, led to improved antigen-specific T cell activation. The bond conformation between the short thiol-terminated PEG chains and the anomeric carbon was both α and β.

SUMMARY OF THE INVENTION

The prior art teaches conjugates of saccharides and proteins in which either a terminal saccharide in an oligosaccharide chain or a saccharide having attached thereto an alkyl chain were utilized. Some studies teach saccharides having attached thereto a PEG chain, whereby the PEG chain serves as a linker to attach mainly agents such as fatty acids but in some cases proteins. Nonetheless, in these studies, the PEG chain that was utilized was relatively short (mostly up to 4 and no more than 6 ethylene glycol units) and furthermore, the PEG was attached to the anomeric carbon via an equatorial bond (β conformation).

While conceiving the present invention, it was envisioned that proteins conjugated to monosaccharides via a medium-to-long hydrophobic linker chain (e.g., a PEG-containing linker having more than 6 alkylene glycol units) would exhibit an improved performance.

It was further envisioned that such conjugates would exhibit an improved performance if the bond conformation between the saccharide moiety and the linker would mimic the conformation between the terminal and penultimate saccharides of naturally occurring protein glycosides. Thus, for example, it was envisioned that conjugates in which the saccharide moiety is M6P or sialic acid, having an ether bond in an α conformation between the anomeric carbon of the saccharide and the linker, would exhibit an improved performance.

According to an aspect of some embodiments of the present invention there is provided a conjugate comprising a biomolecule and a saccharide moiety being covalently linked thereto via a non-hydrophobic linker.

According to some embodiments of the invention, the linker is a non-saccharide moiety.

According to some embodiments of the invention, the linker is attached to an anomeric carbon of the saccharide moiety.

According to some embodiments of the invention, the linker is attached to the anomeric carbon via a bond having an α configuration.

According to an aspect of some embodiments of the present invention there is provided a conjugate comprising a biomolecule and a saccharide moiety being covalently linked thereto via a non-hydrophobic linker, wherein the linker is attached to an anomeric carbon of the saccharide moiety.

According to an aspect of some embodiments of the present invention there is provided a conjugate comprising a biomolecule and a saccharide moiety being covalently linked thereto via a non-hydrophobic linker, wherein the linker is attached to an anomeric carbon of the saccharide moiety via a bond having α configuration.

According to some embodiments of the invention, the linker comprises a poly(alkylene glycol) chain of at least 18 atoms in length.

According to an aspect of some embodiments of the present invention there is provided a conjugate comprising a biomolecule and a saccharide moiety being covalently linked thereto via a poly(alkylene glycol) linker of at least 18 atoms in length.

According to an aspect of some embodiments of the present invention there is provided a conjugate comprising a biomolecule and a saccharide moiety being covalently linked thereto via a poly(alkylene glycol) linker of at least 18 atoms in length, wherein the linker is attached to an anomeric carbon of the saccharide moiety via a bond having α configuration.

According to some embodiments of the invention, the poly(alkylene glycol) comprises poly(ethylene glycol) (PEG).

According to some embodiments of the invention, the poly(alkylene glycol) is from 24 to 36 atoms in length.

According to some embodiments of the invention, the poly(ethylene glycol) comprises from 8 to 12 ethylene glycol units.

According to some embodiments of the invention, the linker comprises at least two chemical moieties which are covalently linked to one another.

According to some embodiments of the invention, the linker comprises at least two poly(alkylene glycol) moieties which are covalently linked to one another.

According to some embodiments of the invention, the at least two chemical moieties are the same or different.

According to some embodiments of the invention, the at least two chemical moieties form a linear linker.

According to some embodiments of the invention, the at least two chemical moieties form a branched linker.

According to some embodiments of the invention, the saccharide moiety is a monosaccharide.

According to some embodiments of the invention, the monosaccharide is a sialic acid.

According to some embodiments of the invention, the conjugate has the formula:

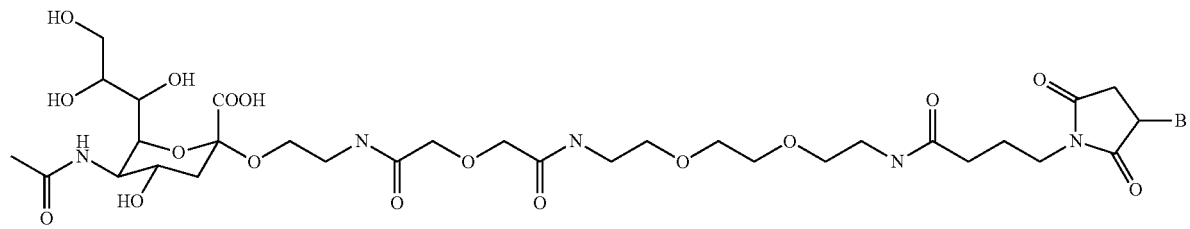

wherein B is the biomolecule.

According to some embodiments of the invention, the biomolecule is attached via a thiol group in the biomolecule.

According to some embodiments of the invention, the biomolecule is a protein and the thiol forms a part of a cysteine residue in the protein.

According to some embodiments of the invention, the biomolecule is a protein and the thiol forms a part of a thiolated lysine residue in the protein.

According to some embodiments of the invention, the conjugate has the formula:

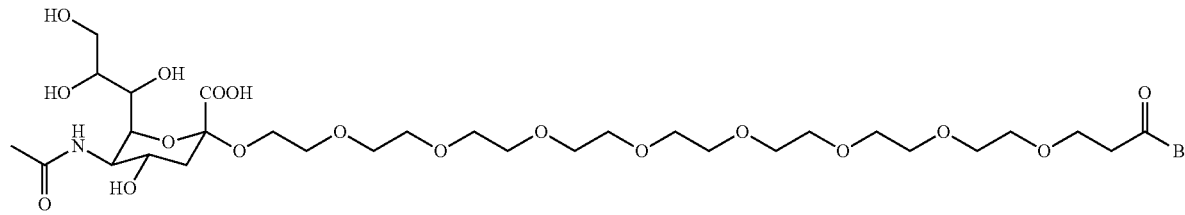

wherein B is the biomolecule.

According to some embodiments of the invention, the biomolecule is attached via an amine group in the biomolecule.

According to some embodiments of the invention, the biomolecule is a protein and the amine forms a part of a lysine residue of the protein.

According to some embodiments of the invention, the monosaccharide is a hexose.

According to some embodiments of the invention, the hexose is a D-hexose.

According to some embodiments of the invention, the linker is attached to the anomeric carbon via a bond having α configuration.

According to some embodiments of the invention, the monosaccharide is selected from the group consisting of a mannose and a M6P.

According to some embodiments of the invention, the conjugate has the formula:

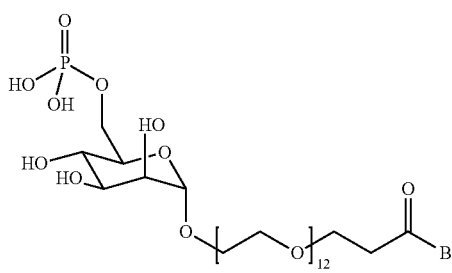

wherein B is the biomolecule.

According to some embodiments of the invention, the conjugate has the formula:

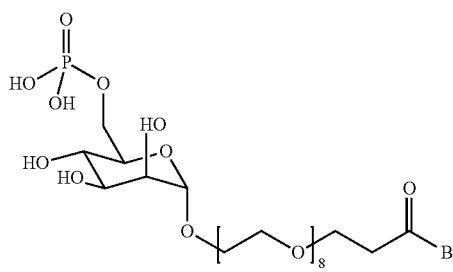

wherein B is the biomolecule.

According to some embodiments of the invention, the conjugate has the formula:
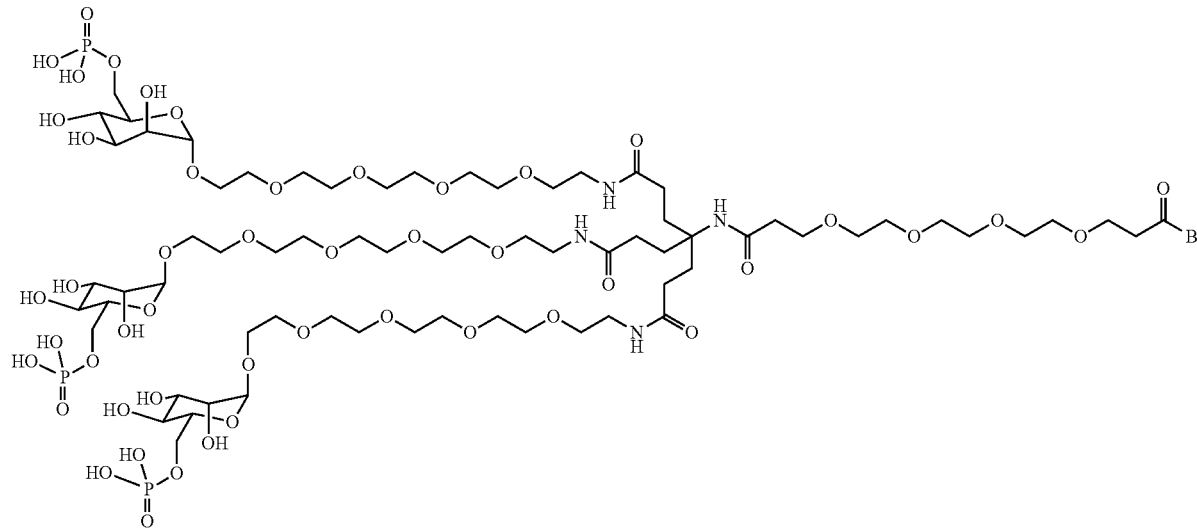
wherein B is the biomolecule.
According to some embodiments of the invention, the conjugate has the formula:
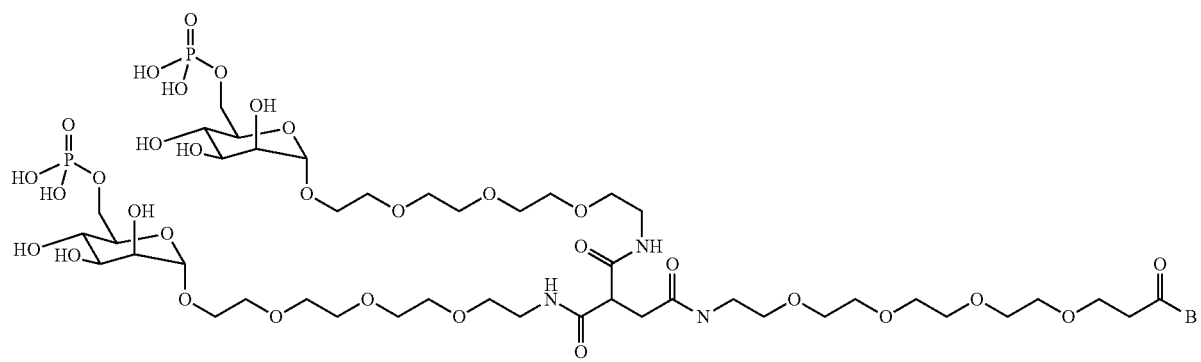
wherein B is the biomolecule.
According to some embodiments of the invention, the biomolecule is attached to the linker via an amine group in the biomolecule.

According to some embodiments of the invention, the biomolecule is a protein and the amine forms a part of a lysine residue of the protein.
According to some embodiments of the invention, the conjugate has the formula:
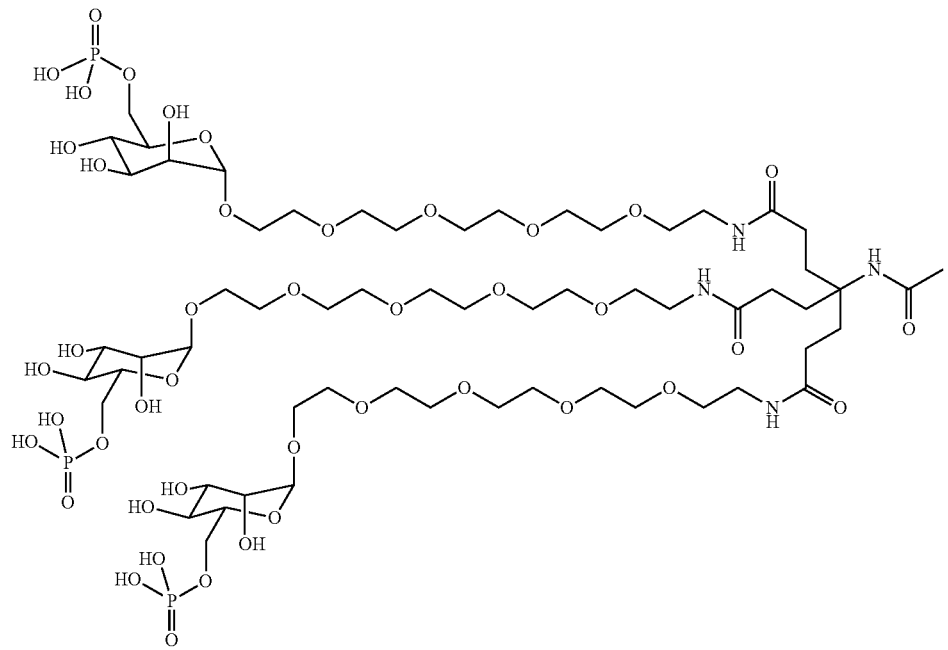
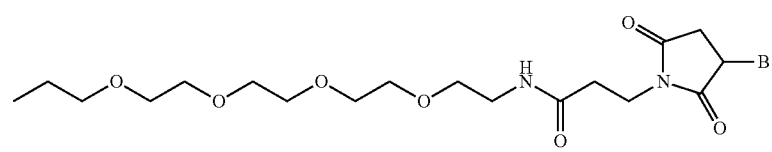
wherein B is the biomolecule.
According to some embodiments of the invention, the conjugate has the formula:
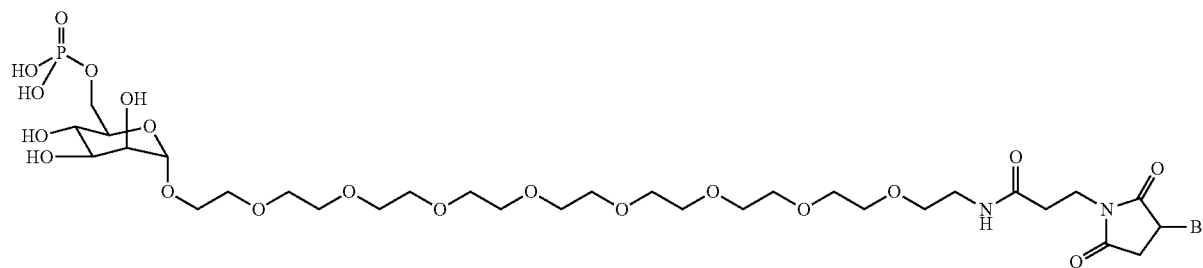
wherein B is the biomolecule.

According to some embodiments of the invention, the conjugate has the formula:

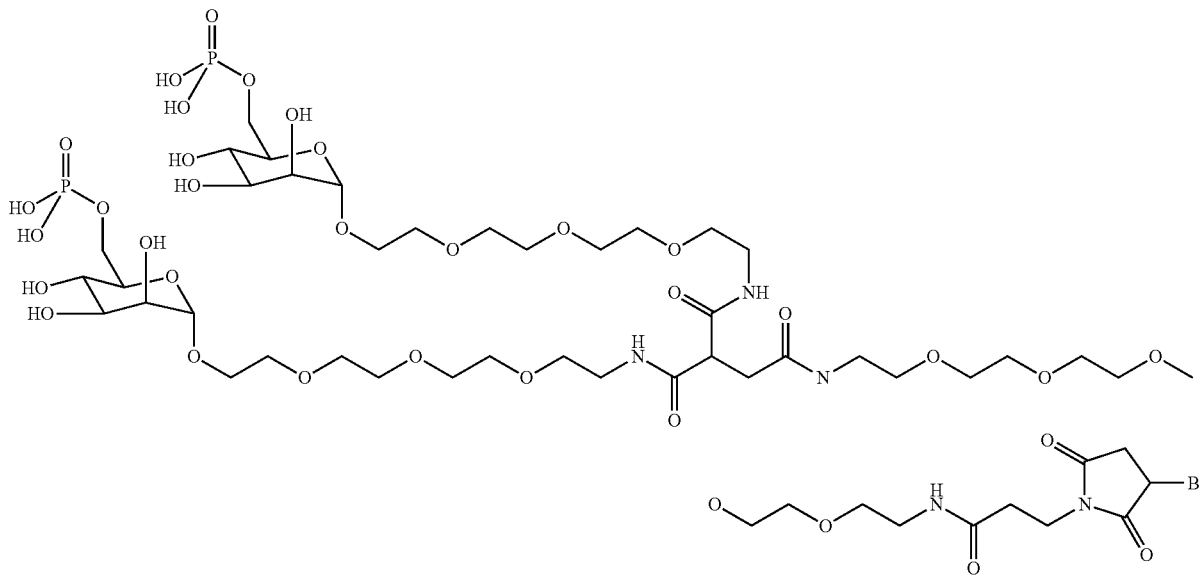

wherein B is the biomolecule.

According to some embodiments of the invention, the biomolecule is attached via a thiol group in the biomolecule.

According to some embodiments of the invention, the biomolecule is a protein and the thiol forms a part of a cysteine residue in the protein.

According to some embodiments of the invention, the biomolecule is a protein and the thiol forms a part of a thiolated lysine residue in the protein.

According to some embodiments of the invention, the biomolecule is selected from the group consisting of a protein, a peptide, an oligonucleotide, an antisense, a polynucleotide, a hormone, a steroid, an antibody, an antigen, a toxin, a growth factor, an agonist, an antagonist, a co-factor, a cytokine residue, an enzyme, an immunoglobulin, an inhibitor, a ligand, a prostaglandin, a vaccine and a vitamin.

According to some embodiments of the invention, the biomolecule is a protein.

According to some embodiments of the invention, the protein is a recombinant protein produced by a host cell.

According to some embodiments of the invention, the protein is plant cell produced recombinant protein.

According to some embodiments of the invention, the biomolecule is selected from the group consisting of a lysosomal protective protein, L-iduronidase, iduronate-2-sulfatase, heparan-N-sulfatase, α-N-acetylglucosaminidase, acetyl-CoA:α-glucosaminide acetyltransferase, N-acetylglucosamine-6-sulfatase, galactose-6-sulfatase, β-galactosidase, N-acetylgalactosamine-4-sulfatase, β-glucuronidase, hyaluronoglucosaminidase, aspartylglucosaminidase, acid lipase, cystine transporter, Lamp-2, α-galactosidase A, acid ceramidase, α-L-fucosidase, glucocerebrosidase, galactocerebrosidase, α-glucosidase, β-galactosidase, β-hexosaminidase A, β-hexosaminidase B, ganglioside GM2 activator protein, α-D-mannosidase, β-D-mannosidase, arylsulfatase A, saposin B, neuraminidase, phosphotransferase, palmitoyl protein thioesterase, tripeptidyl peptidase I, acid sphingomyelinase, cathepsin K, α-galactosidase B, sialic acid transporter, tartrate-resistant acid phosphatase, asparaginase, ceroid lipofuscinosis neuronal protein 5, CPVL, cathepsin B, dipeptidyl-peptidase I, cathepsin D, cathepsin H, cathepsin L, cathepsin S, cathepsin Z, deoxyribonuclease II, dipeptidyl-peptidase II, N-acetylgalactosamine-6-sulfatase, γ-glutamyl hydrolase, heparanase, legumain, 1-O-acylceramide synthase, myeloperoxidase, α-N-acetylgalactosaminidase, NPC2 protein, plasma glutamate carboxypeptidase, Pro-X carboxypeptidase, proactivator polypeptide, N-sulfoglucosamine sulfohydrolase, sialic acid 9-O-acetylesterase, tripeptidyl-peptidase I, lactotransferrin, pancreatic ribonuclease, hornerin, cation-dependent mannose-6-phosphate receptor, ribonuclease K6, intercellular adhesion molecule 1, CREG1 protein, laminin A, hemoglobin ζ chain, cerebellin 4, desmoplakin, fatty acid-binding protein, sulfatase-modifying factor, leukocyte elastase, procollagen-lysine-2-oxoglutarate-5-dioxygenase 1, ferritin light chain, acid sphingomyelinase-like phosphodiesterase 3A, hemoglobin β chain, ribonuclease T2, cat eye syndrome critical region 1, leucine-rich $α_2$-glycoprotein, antithrombin-III, serum amyloid P-component, plasma serine protease inhibitor, haptoglobin-related protein, complement C1q subcomponent A chain, complement C1q subcomponent B chain, complement C1q subcomponent C chain, cholinesterase, angiotensinogen, prostaglandin-$H_2$ D-isomerase, plasma protease C1 inhibitor, mammalian ependymin-related protein, $α_1$B-glycoprotein, plasma kallikrein, hemopexin, AMBP protein, $α_1$-antitrypsin, pigment epithelium-derived factor, $α_2$-macroglobulin, kallistatin, Fc fragment of IgG-binding protein, corticosteroid-binding globulin, zinc-$α_2$-glycoprotein, afamin, serotransferrin, ceruloplasmin, biotimidase, ficolin-3, serum albumin, $α_1$-acid glycoprotein 1, $α_1$-acid glycoprotein 2, CD5 antigen-like, complement C2 precursor, complement C3 precursor, inter-α-trypsin inhibitor heavy chain H4, inter-α-trypsin inhibitor heavy chain 2, inter-α-trypsin inhibitor heavy chain 1, ficolin-2, complement factor B, dopamine β-hydroxylase, fibrinogen β chain, $α_1$-antichymotrypsin, extracellular matrix protein 1, kininogen-1, lumican, complement component 4B, cation-independent mannose-6-phosphate receptor, adipocyte-derived leucine aminopeptidase, fetuin-B, N-acetylmuramoyl-L-alanine amidase, histidine-rich glycoprotein, vitronectin, $\alpha_2$-HS-glycoprotein, clusterin, C4b-binding protein α chain, mannan-binding lectin serine protease 1, and transthyretin.

According to some embodiments of the invention, the protein is a green fluorescent protein.

According to some embodiments of the invention, the biomolecule is a lysosomal protein.

According to some embodiments of the invention, the lysosomal protein is a glucocerebrosidase.

According to some embodiments of the invention, the lysosomal protein is an α-galactosidase.

According to some embodiments of the invention, the monosaccharide is M6P.

According to some embodiments of the invention, the monosaccharide is a sialic acid.

According to some embodiments of the invention, the sialic acid is N-acetylneuraminic acid.

According to some embodiments of the invention, the biomolecule is a follicle-stimulating hormone (FSH).

According to some embodiments of the invention, the linker is attached to the biomolecule via a covalent bond formed between a reactive group in the linker and a functional group on the biomolecule.

According to some embodiments of the invention, the reactive group is a carboxylate and the functional group is an amine.

According to some embodiments of the invention, the biomolecule is a protein and the amine forms a part of a lysine residue of the protein.

According to some embodiments of the invention, the reactive group is an amine and the functional group is a carboxylate.

According to some embodiments of the invention, the biomolecule is a protein and the carboxylate forms a part of a glutamate residue and/or an aspartate residue in the protein.

According to some embodiments of the invention, the reactive group is a maleimide and the functional group is a thiol.

According to some embodiments of the invention, the biomolecule is a protein and the thiol forms a part of a cysteine residue in the protein.

According to some embodiments of the invention, the biomolecule is a protein and the thiol forms a part of a thiolated lysine residue in the protein.

According to some embodiments of the invention, an uptake of the conjugate into cells is at least 10% higher than an uptake of the biomolecule into the cells.

According to an aspect of some embodiments of the present invention there is provided a conjugate having the formula:

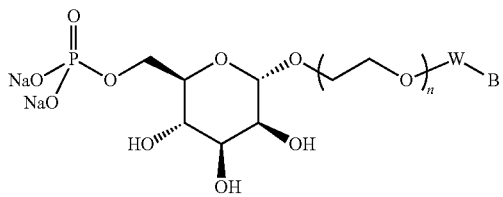

wherein:
n=8;
W is selected from the group consisting of —CH$_2$CH$_2$C(=O)— and —CH$_2$CH$_2$—NHCOCH$_2$CH$_2$-maleimide; and
B is an α-galactosidase.

According to an aspect of some embodiments of the present invention there is provided a conjugate having the formula:

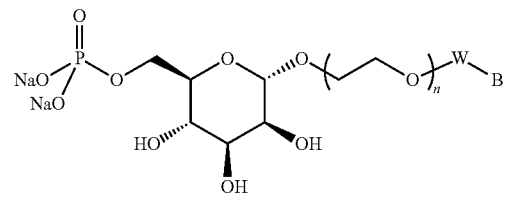

wherein:
n=8;
W is selected from the group consisting of —CH$_2$CH$_2$C(=O)— and —CH$_2$CH$_2$—NHCOCH$_2$CH$_2$-maleimide; and
B is a glucocerebrosidase.

According to an aspect of some embodiments of the present invention there is provided a conjugate having the formula:

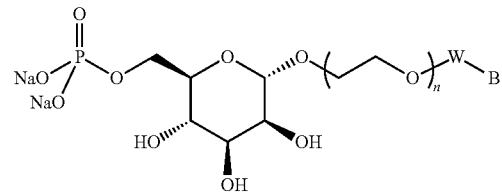

wherein:
n=8;
W is selected from the group consisting of —CH$_2$CH$_2$C(=O)— and —CH$_2$CH$_2$—NHCOCH$_2$CH$_2$-maleimide; and
B is a green fluorescent protein.

According to an aspect of some embodiments of the present invention there is provided a process of preparing a conjugate described herein, the process comprising reacting a glycosylation reagent, which comprises the saccharide moiety having attached thereto a non-hydrophobic linker having a reactive group, with the biomolecule.

According to some embodiments of the invention, the reactive group is selected from the group consisting of an amine, a maleimide and a carboxylate.

According to some embodiments of the invention, the reactive group is a carboxylate, and the carboxylate is reacted with an amine-containing moiety on the biomolecule.

According to some embodiments of the invention, the biomolecule is a protein and the amine forms a part of a lysine residue of the protein.

According to some embodiments of the invention, the reactive group is an amine, and the amine is reacted with a carboxylate on the biomolecule.

According to some embodiments of the invention, the biomolecule is a protein and the carboxylate forms a part of a glutamate and/or an aspartate residue in the protein.

According to some embodiments of the invention, the reactive group is a maleimide, and the maleimide is reacted with a thiol on the biomolecule.

According to some embodiments of the invention, the biomolecule is a protein and the thiol forms a part of a cysteine residue in the protein.

According to some embodiments of the invention, the biomolecule is a protein and the thiol forms a part of a thiolated lysine residue in the protein.

According to some embodiments of the invention, the glycosylation reagent is selected from the group consisting of:
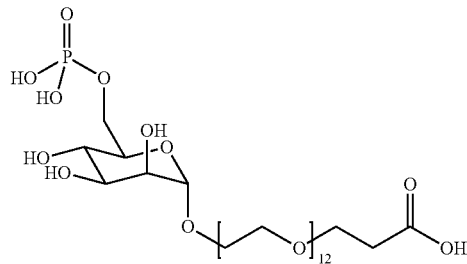
a)
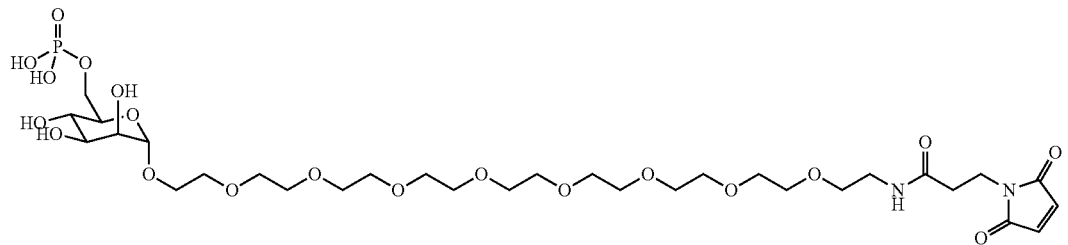
b)
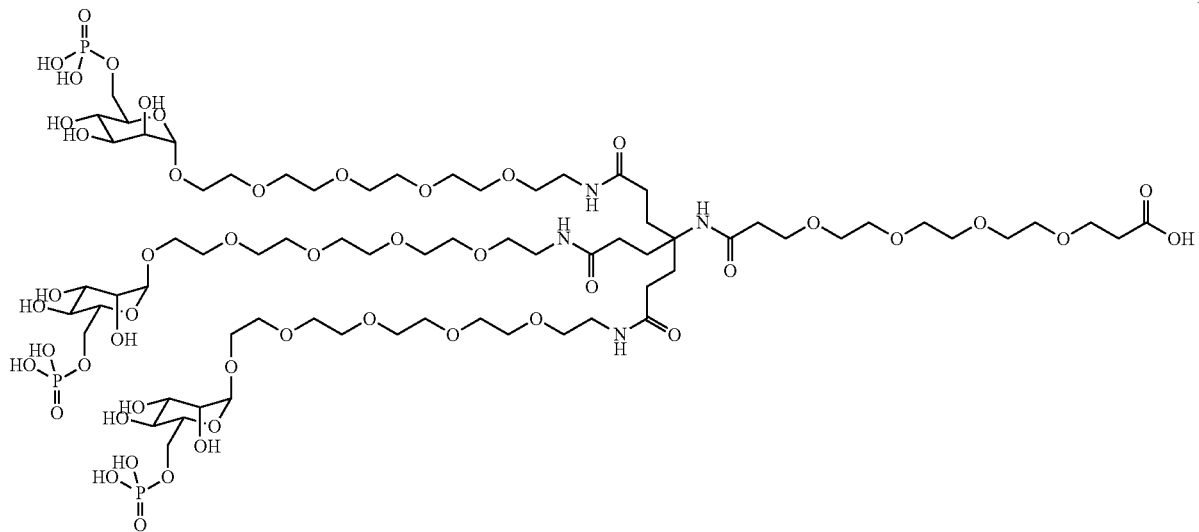
c)
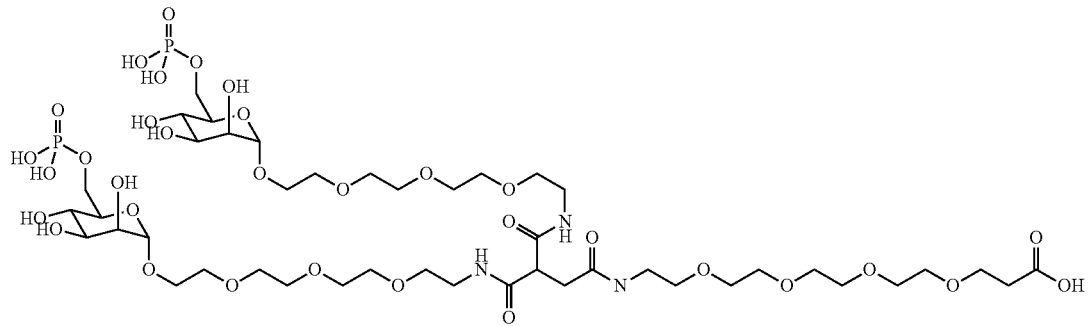
d)

-continued
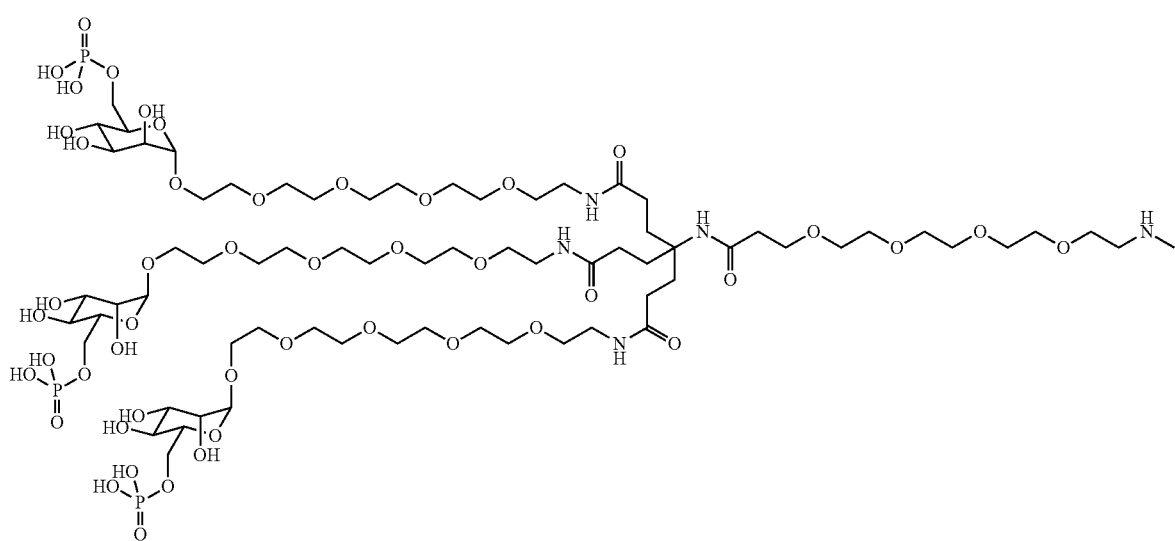
e)
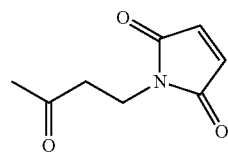
f)
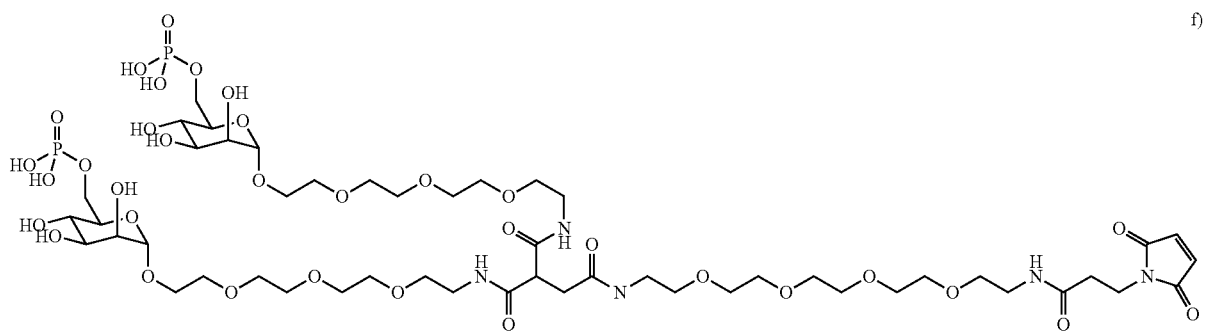
g)
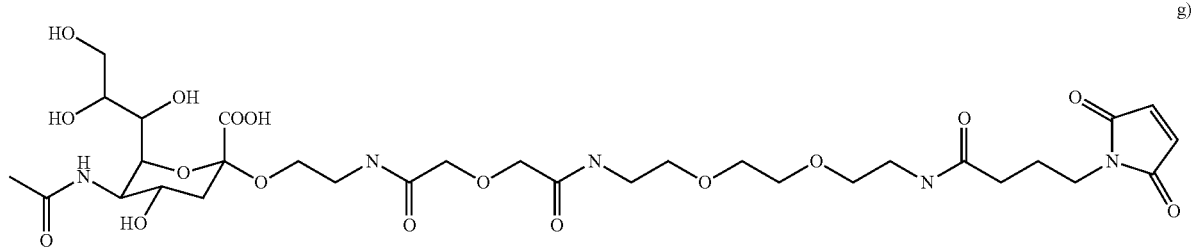
h)
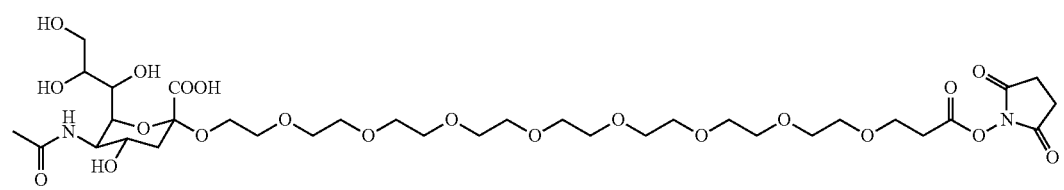

According to some embodiments of the invention, the glycosylation reagent has the formula:

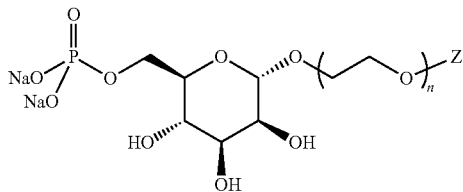

wherein:
n=8; and
Z is selected from the group consisting of —CH$_2$CH$_2$CO$_2$H and —CH$_2$CH$_2$—NHCOCH$_2$CH$_2$-maleimide.

According to some embodiments of the invention, the biomolecule is an α-galactosidase.

According to some embodiments of the invention, the biomolecule is a glucocerebrosidase.

According to some embodiments of the invention, the biomolecule is a green fluorescent protein.

According to some embodiments of the invention, the glycosylating agent and the biomolecule are reacted using a stoichiometric ratio of the glycosylation reagent to the biomolecule, the ratio being selected so as to control the average number of saccharide moieties conjugated to the biomolecule.

According to an aspect of some embodiments of the present invention there is provided a pharmaceutical composition comprising the conjugate described herein and a pharmaceutically acceptable carrier.

According to an aspect of some embodiments of the present invention there is provided a use of a conjugate described herein as a fluorescent labeling agent.

According to an aspect of some embodiments of the present invention there is provided a use of a conjugate described herein, in the manufacture of a medicament.

According to some embodiments of the invention, the protein is a lysosomal protein and the medicament is for treating a metabolic disease.

According to some embodiments of the invention, the disease is a lysosomal storage disease.

According to some embodiments of the invention, the disease is selected from the group consisting of mucopolysaccharidosis types I, II, IIIA, IIIB, IIIC, IIID, IVA, IVB, VI, VII and IX, aspartylglucosaminuria, cholesterol ester storage disease, cystinosis, Danon disease, Fabry disease, Farber disease, fucosidosis, galactosialidosis, Gaucher disease, globoid cell leucodystrophy, GM1-gangliosidosis, Tay Sachs disease, Sandhoff disease, GM2-gangliosidosis, α-mannosidosis, β-mannosidosis, metachromatic leucodystrophy, mucolipidosis type I, mucolipidosis type II, mucolipidosis type IIIC, multiple sulfatase deficiency, CLN1 Batten disease, CLN2 Batten disease, Niemann-Pick disease types A, B and C, pycnodysostosis, Schindler disease and sialic acid storage disease.

According to some embodiments of the invention, the medicament is for treating a protein-related disease.

According to some embodiments of the invention, the protein-related disease is associated with at least one protein selected from the group consisting of follicle-stimulating hormone, a lysosomal protective protein, L-iduronidase, iduronate-2-sulfatase, heparan-N-sulfatase, α-N-acetylglucosaminidase, acetylCoA:α-glucosaminide acetyltransferase, N-acetylglucosamine-6-sulfatase, galactose-6-sulfatase, β-galactosidase, N-acetylgalactosamine-4-sulfatase, β-glucuronidase, hyaluronoglucosaminidase, aspartylglucosaminidase, acid lipase, cystine transporter, Lamp-2, α-galactosidase A, acid ceramidase, α-L-fucosidase, glucocerebrosidase, galactocerebrosidase, α-glucosidase, β-galactosidase, β-hexosaminidase A, β-hexosaminidase B, ganglioside GM2 activator protein, α-D-mannosidase, β-D-mannosidase, arylsulfatase A, saposin B, neuraminidase, phosphotransferase, palmitoyl protein thioesterase, tripeptidyl peptidase I, acid sphingomyelinase, cathepsin K, α-galactosidase B, sialic acid transporter, tartrate-resistant acid phosphatase, asparaginase, ceroid lipofuscinosis neuronal protein 5, CPVL, cathepsin B, dipeptidyl-peptidase I, cathepsin D, cathepsin H, cathepsin L, cathepsin S, cathepsin Z, deoxyribonuclease II, dipeptidyl-peptidase II, N-acetylgalactosamine-6-sulfatase, γ-glutamyl hydrolase, heparanase, legumain, 1-O-acylceramide synthase, myeloperoxidase, α-N-acetylgalactosaminidase, NPC2 protein, plasma glutamate carboxypeptidase, Pro-X carboxypeptidase, proactivator polypeptide, N-sulfoglucosamine sulfohydrolase, sialic acid 9-O-acetylesterase, tripeptidyl-peptidase I, lactotransferrin, pancreatic ribonuclease, hornerin, cation-dependent mannose-6-phosphate receptor, ribonuclease K6, intercellular adhesion molecule 1, CREG1 protein, laminin A, hemoglobin ζ chain, cerebellin 4, desmoplakin, fatty acid-binding protein, sulfatase-modifying factor, leukocyte elastase, procollagen-lysine-2-oxoglutarate-5-dioxygenase 1, ferritin light chain, acid sphingomyelinase-like phosphodiesterase 3A, hemoglobin β chain, ribonuclease T2, cat eye syndrome critical region 1, leucine-rich α$_2$-glycoprotein, antithrombin-III, serum amyloid P-component, plasma serine protease inhibitor, haptoglobin-related protein, complement C1q subcomponent A chain, complement C1q subcomponent B chain, complement C1q subcomponent C chain, cholinesterase, angiotensinogen, prostaglandin-H$_2$ D-isomerase, plasma protease C1 inhibitor, mammalian ependymin-related protein, α$_1$B-glycoprotein, plasma kallikrein, hemopexin, AMBP protein, α$_1$-antitrypsin, pigment epithelium-derived factor, α$_2$-macroglobulin, kallistatin, Fc fragment of IgG-binding protein, corticosteroid-binding globulin, zinc-α$_2$-glycoprotein, afamin, serotransferrin, ceruplasmin, biotimidase, ficolin-3, serum albumin, α$_1$-acid glycoprotein 1, α$_1$-acid glycoprotein 2, CD5 antigen-like, complement C2 precursor, complement C3 precursor, inter-α-trypsin inhibitor heavy chain H4, inter-α-trypsin inhibitor heavy chain 2, inter-α-trypsin inhibitor heavy chain 1, ficolin-2, complement factor B, dopamine β-hydroxylase, fibrinogen β chain, α$_1$-antichymotrypsin, extracellular matrix protein 1, kininogen-1, lumican, complement component 4B, cation-independent mannose-6-phosphate receptor, adipocyte-derived leucine aminopeptidase, fetuin-B, N-acetylmuramoyl-L-alanine amidase, histidine-rich glycoprotein, vitronectin, α$_2$-HS-glycoprotein, clusterin, C4b-binding protein α chain, mannan-binding lectin serine protease 1, and transthyretin.

According to some embodiments of the invention, the protein-related disease is associated with a deficiency of the at least one protein.

According to some embodiments of the invention, the conjugate localizes the biomolecule in a tissue.

According to some embodiments of the invention, an activity of the biomolecule in the conjugate is at least the same as an activity of a non-modified form of the biomolecule.

According to some embodiments of the invention, the medicament is used in enzyme replacement therapy, hormone replacement therapy and/or as a vaccine.

According to an aspect of some embodiments of the present invention there is provided a use of a conjugate having the formula:

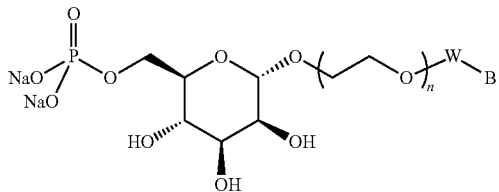

wherein:
n=8;
W is selected from the group consisting of —CH$_2$CH$_2$C(=O)— and —CH$_2$CH$_2$—NHCOCH$_2$CH$_2$-maleimide-; and
B is an α-galactosidase,
in the manufacture of a medicament for treating Fabry disease.

According to an aspect of some embodiments of the present invention there is provided a use of a conjugate having the formula:

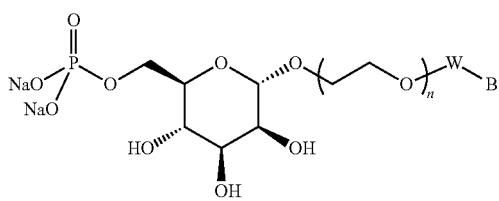

wherein:
n=8;
W is selected from the group consisting of —CH$_2$CH$_2$C(=O)— and —CH$_2$CH$_2$—NHCOCH$_2$CH$_2$-maleimide-; and
B is a glucocerebrosidase,
in the manufacture of a medicament for treating Gaucher's disease.

According to an aspect of some embodiments of the present invention there is provided a compound comprising a saccharide moiety and a non-hydrophobic linker being attached thereto.

According to some embodiments of the invention, the linker is a non-saccharide moiety.

According to some embodiments of the invention, the linker is attached to an anomeric carbon of the saccharide moiety.

According to some embodiments of the invention, the linker is attached to the anomeric carbon via a bond having an α configuration.

According to an aspect of some embodiments of the present invention there is provided a compound comprising a saccharide moiety and a non-hydrophobic linker being attached thereto, wherein the linker is attached to an anomeric carbon of the saccharide moiety.

According to an aspect of some embodiments of the present invention there is provided a compound comprising a saccharide moiety and a non-hydrophobic linker being attached thereto, wherein the linker is attached to an anomeric carbon of the saccharide moiety via a bond having α configuration.

According to some embodiments of the invention, the linker comprises a poly(alkylene glycol) chain of at least 18 atoms in length.

According to an aspect of some embodiments of the present invention there is provided a compound comprising a saccharide moiety and a poly(alkylene glycol) linker being attached thereto, the linker being of at least 18 atoms in length.

According to an aspect of some embodiments of the present invention there is provided a compound comprising a saccharide moiety and a poly(alkylene glycol) linker being attached thereto, the linker being at least 18 atoms in length, wherein the linker is attached to an anomeric carbon of the saccharide moiety via a bond having a configuration.

According to some embodiments of the invention, the poly(alkylene glycol) comprises poly(ethylene glycol) (PEG).

According to some embodiments of the invention, the poly(alkylene glycol) is from 24 to 36 atoms in length.

According to some embodiments of the invention, the poly(ethylene glycol) comprises from 8 to 12 ethylene glycol units.

According to some embodiments of the invention, the linker comprises at least two chemical moieties which are covalently linked to one another.

According to some embodiments of the invention, the linker comprises at least two poly(alkylene glycol) moieties which are covalently linked to one another.

According to some embodiments of the invention, the at least two chemical moieties are the same or different.

According to some embodiments of the invention, the at least two chemical moieties form a linear linker.

According to some embodiments of the invention, the at least two chemical moieties form a branched linker.

According to some embodiments of the invention, the saccharide moiety is a monosaccharide.

According to some embodiments of the invention, the saccharide moiety is a hexose.

According to some embodiments of the invention, the monosaccharide is selected from the group consisting of a mannose and a M6P.

According to some embodiments of the invention, the linker comprises a reactive group.

According to some embodiments of the invention, the linker terminates by the reactive group.

According to some embodiments of the invention, the reactive group is in a protected form thereof.

According to some embodiments of the invention, the reactive group is selected from the group consisting of an amine, a maleimide and a carboxylate.

According to an aspect of some embodiments of the present invention there is provided a compound having the formula:

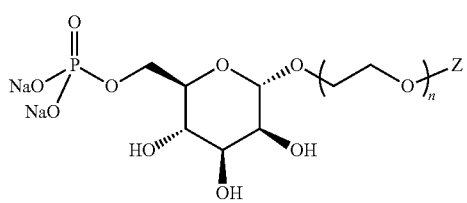

wherein:
n=8; and
Z is selected from the group consisting of —CH$_2$CH$_2$CO$_2$H and —CH$_2$CH$_2$—NHCOCH$_2$CH$_2$-maleimide.

According to an aspect of some embodiments of the present invention there is provided a compound selected from the group consisting of:
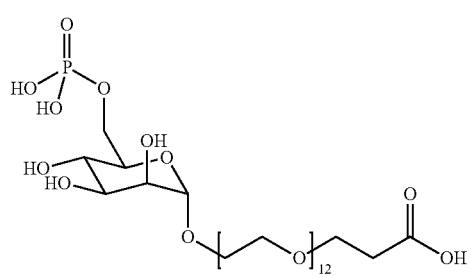
a)
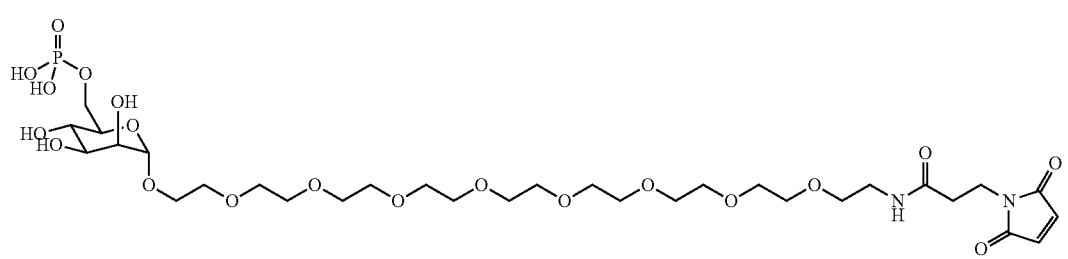
b)
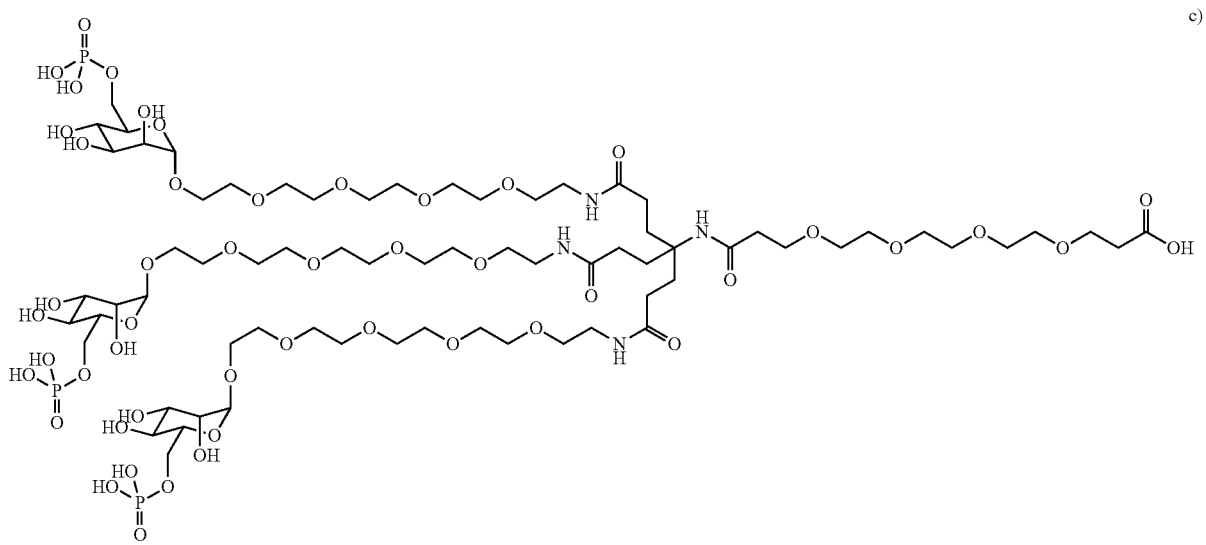
c)
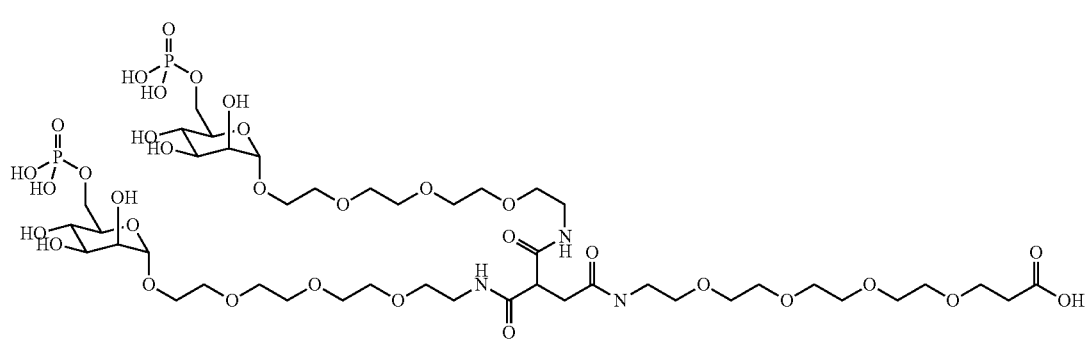
d)

-continued
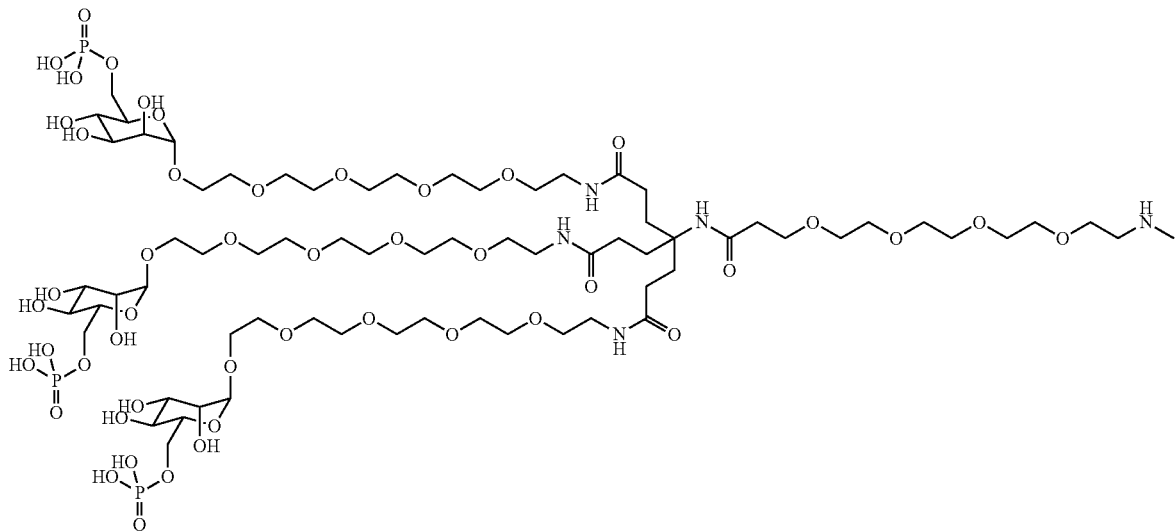
e)
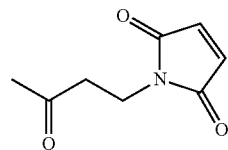
f)
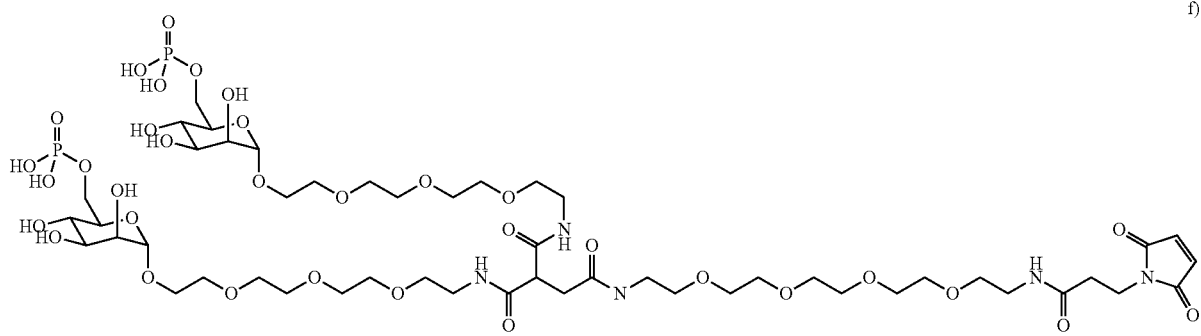
g)
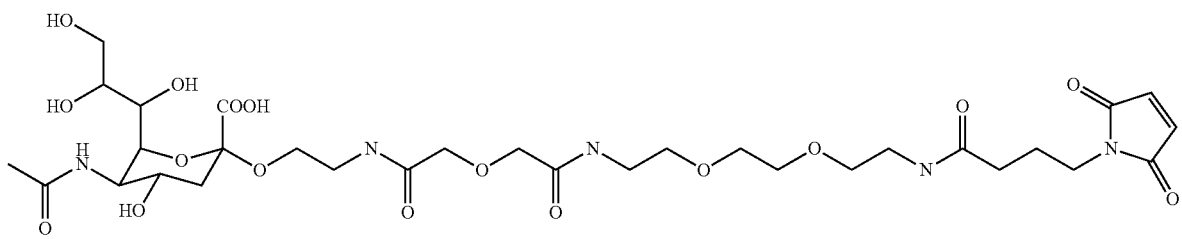
h)
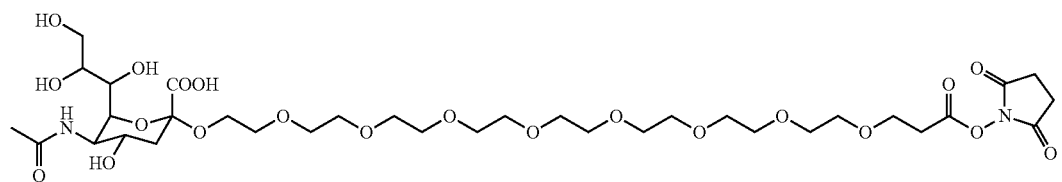

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a," "an," and "the" include plural references unless the context clearly dictates otherwise. For example, the term "a compound" or "at least one compound" may include a plurality of compounds, including mixtures thereof.

As used herein the term "about" refers to ±10%.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images and drawings. With specific reference now to the images and drawings in detail, it is stressed that the particulars shown are by way of example and for purposes of illustrative discussion of embodiments of the invention. In this regard, the description taken with the images makes apparent to those skilled in the art how embodiments of the invention may be practiced.

In the drawings:

Figure 1A:
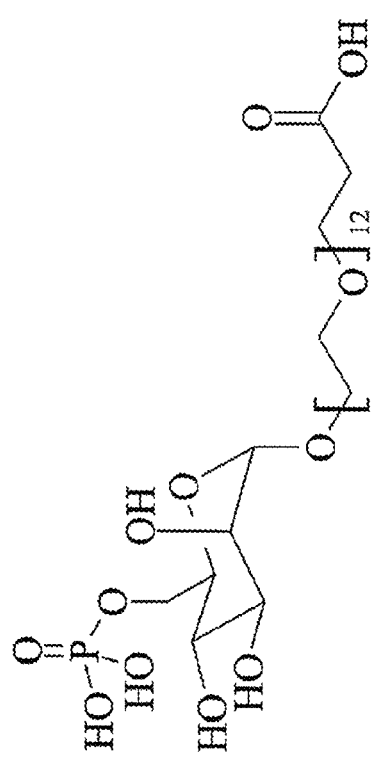
Figure 1B:
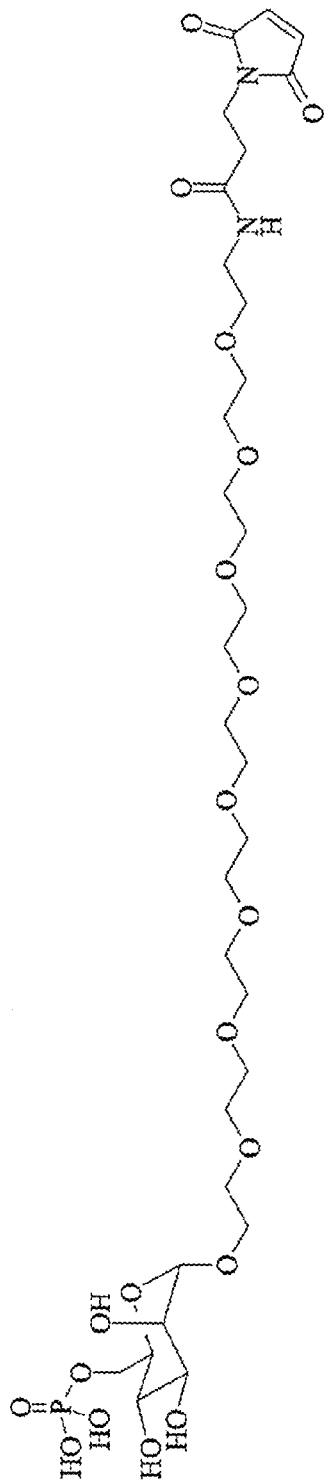
Figures 2A, 2B:
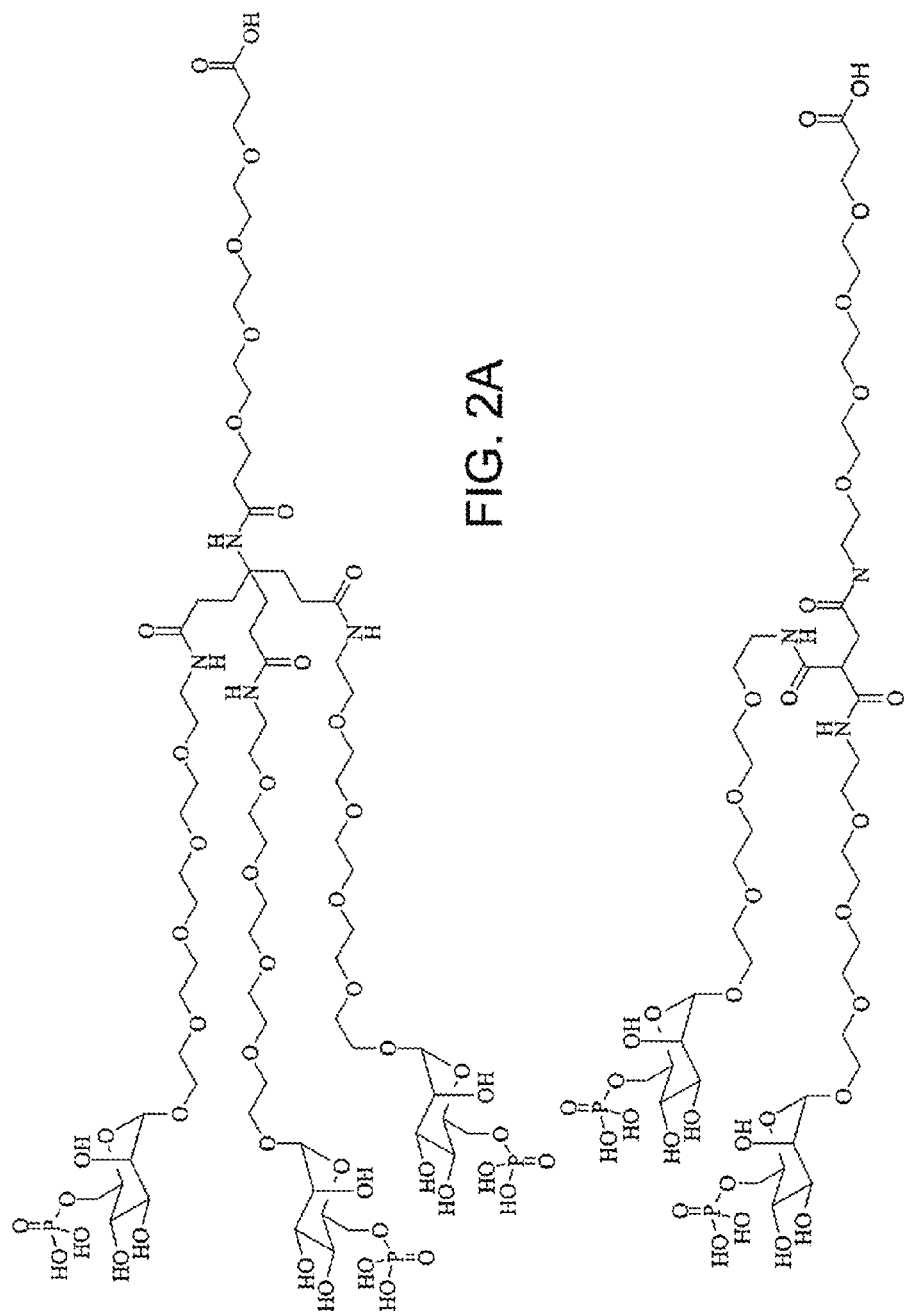
Figure 2C:
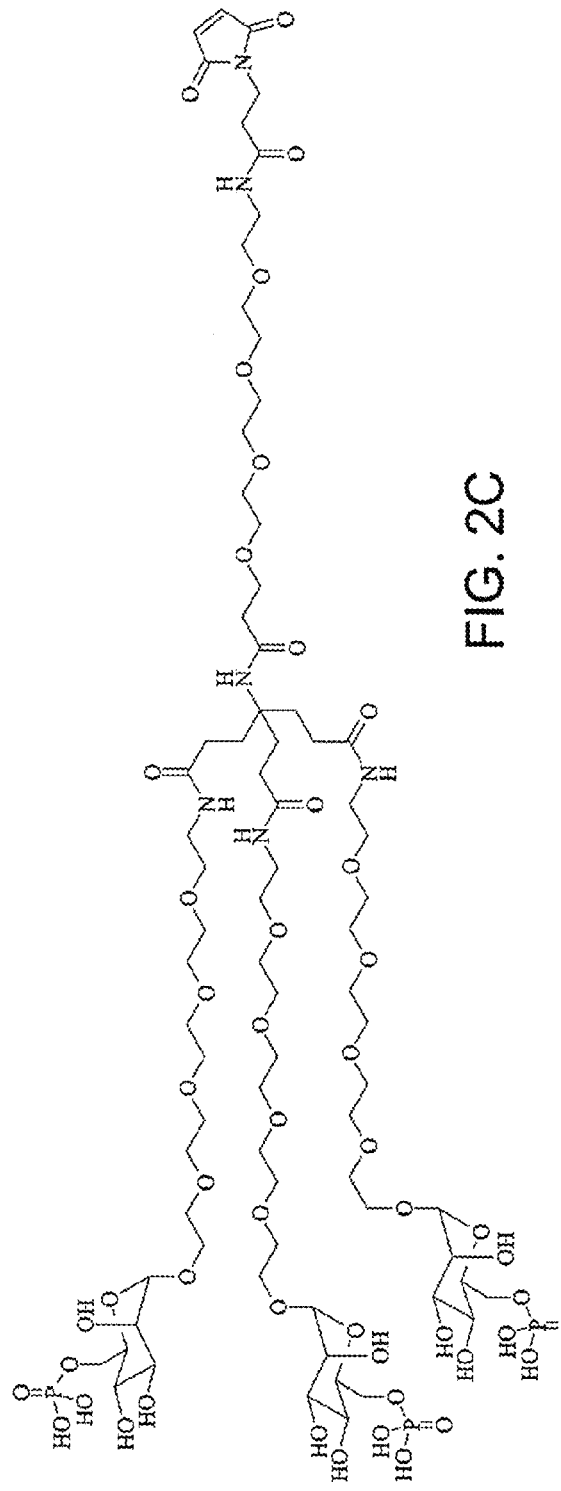
Figure 2D:
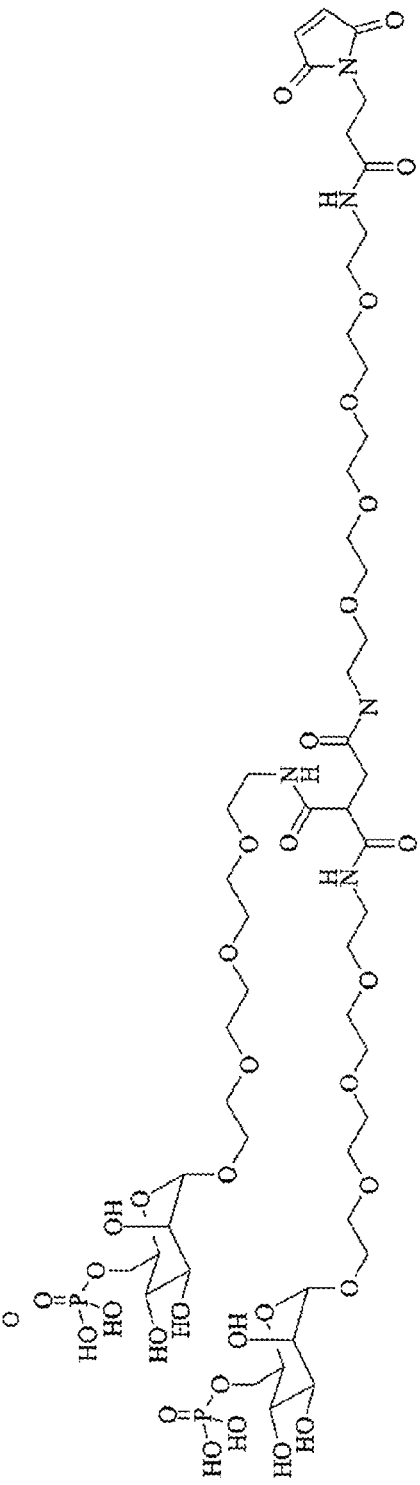
Figure 3A:
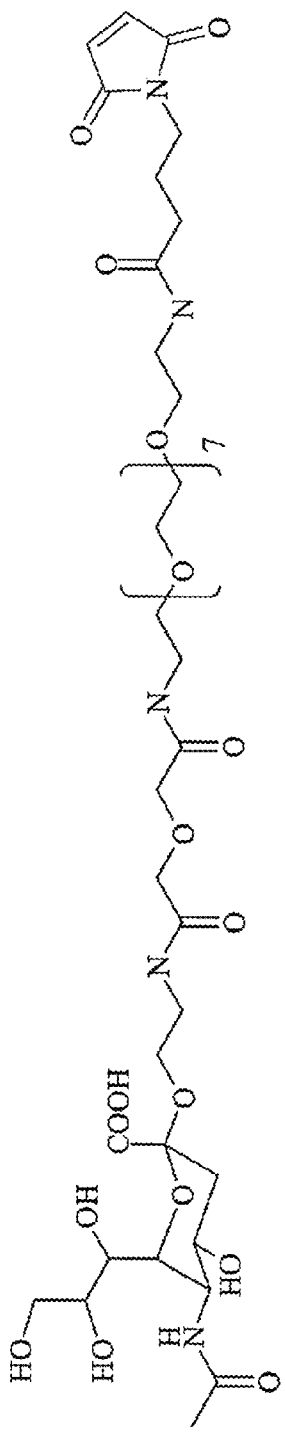
Figure 3B:
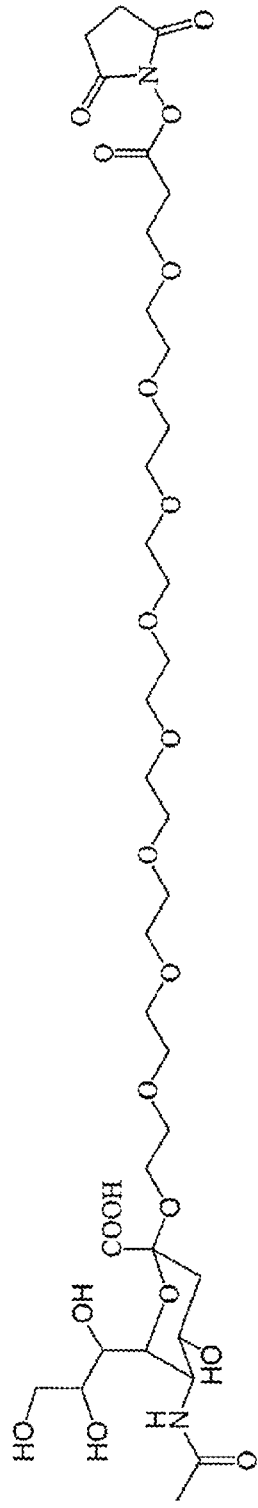
Figure 4:
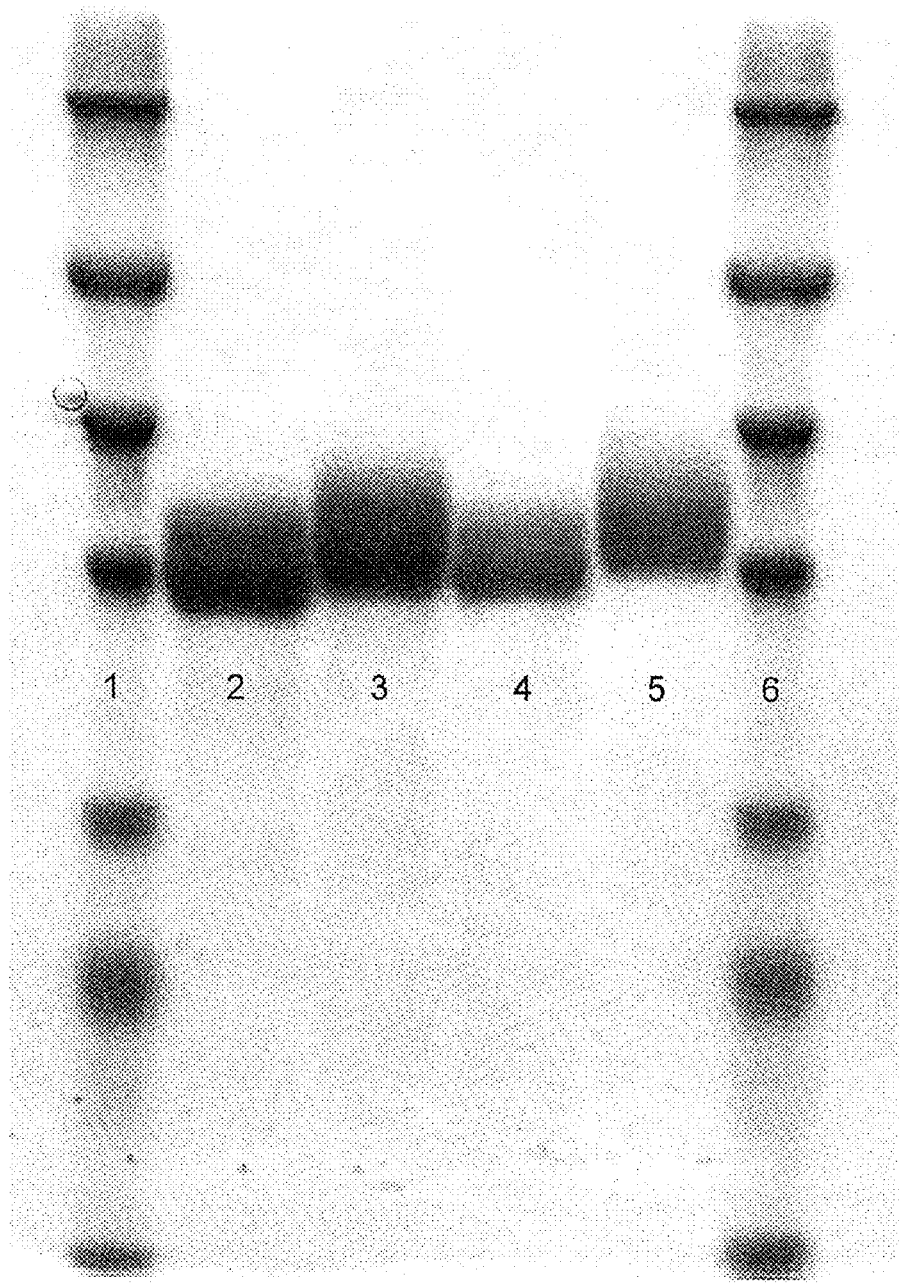
Figure 5:
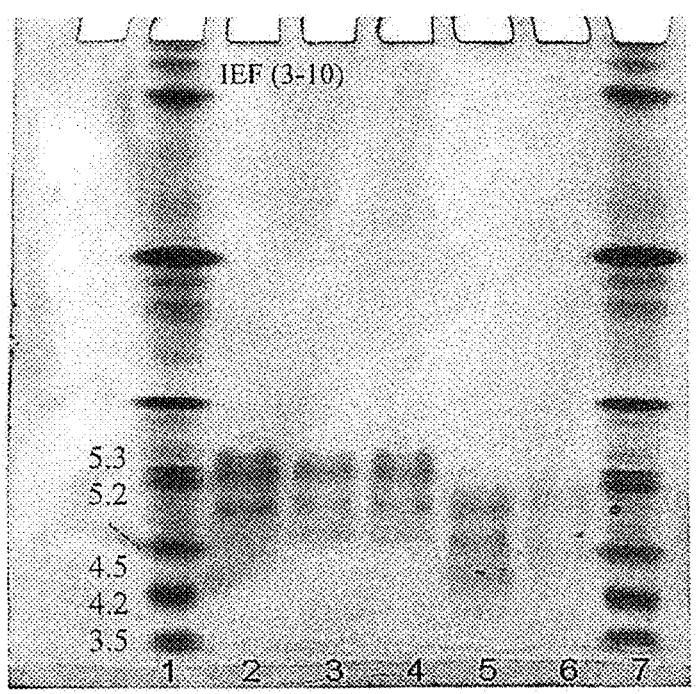
Figure 6:
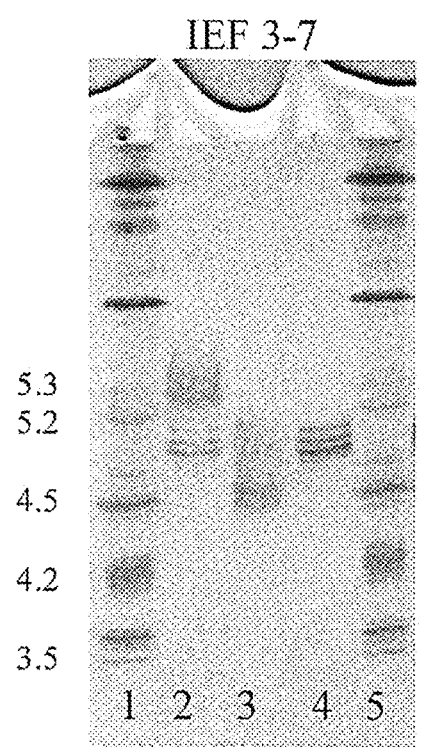
Figure 7:
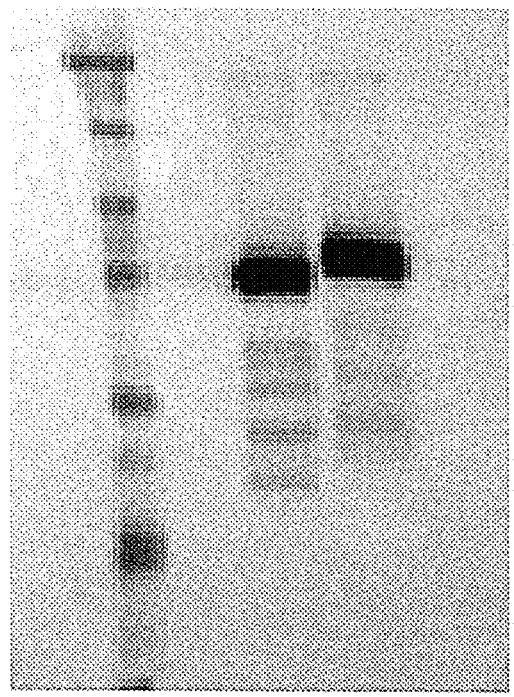
Figure 9:
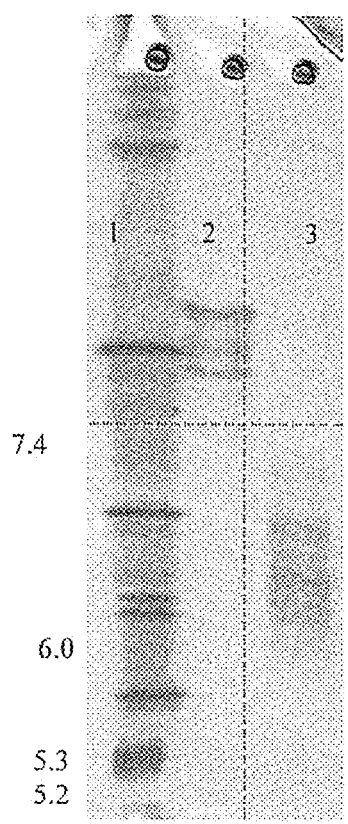
Figure 10:
Figure 11A:
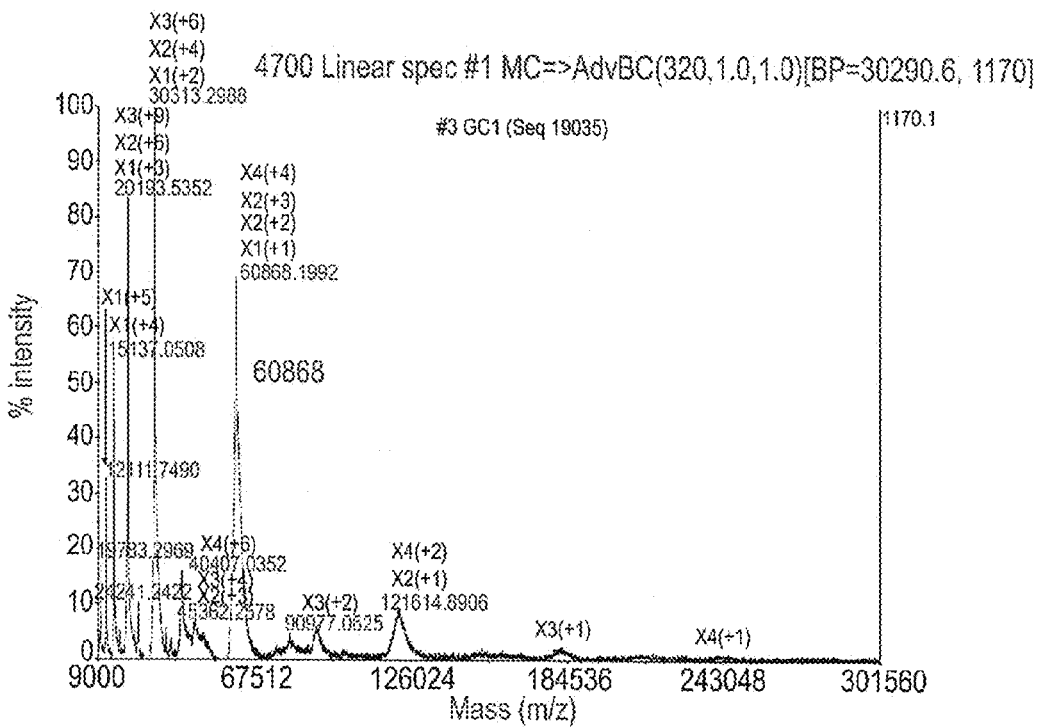
Figure 11B:
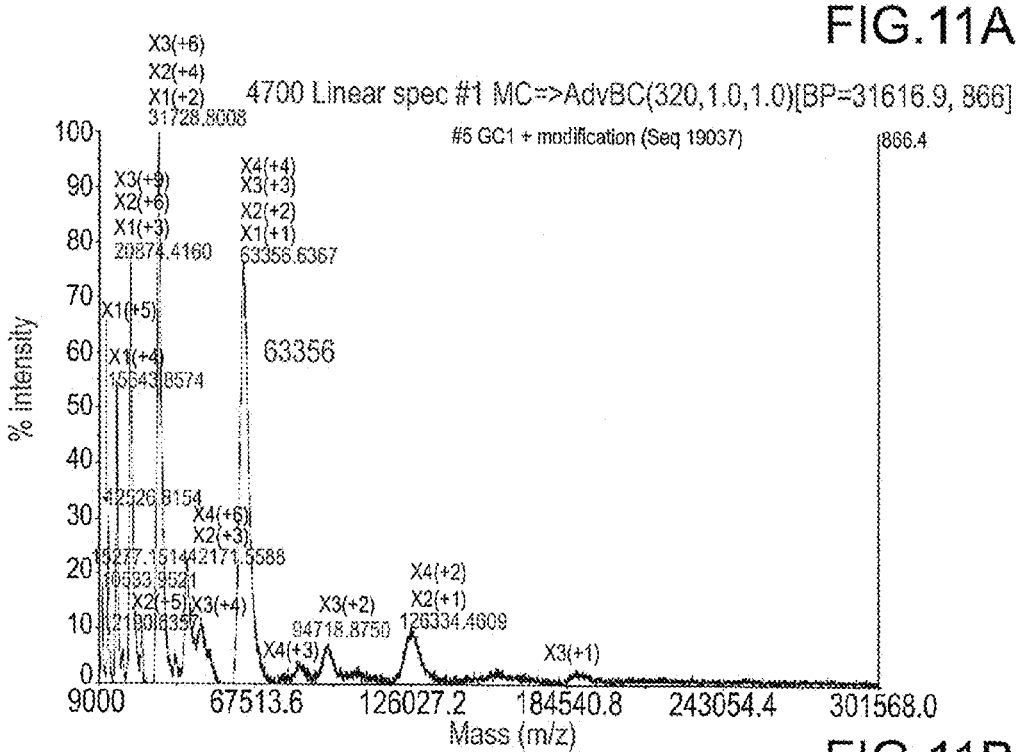
Figure 12A:
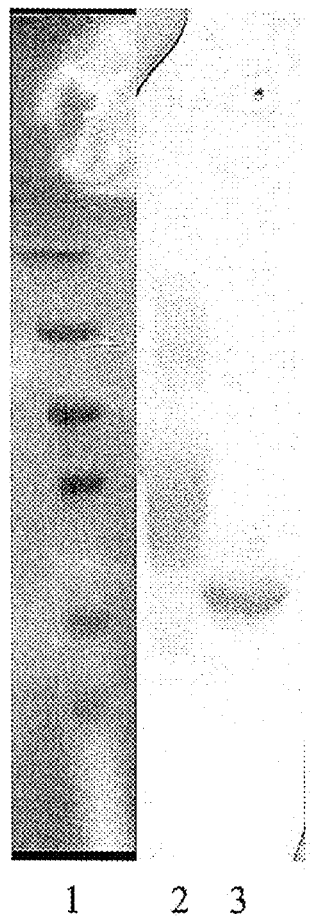
Figure 12B:
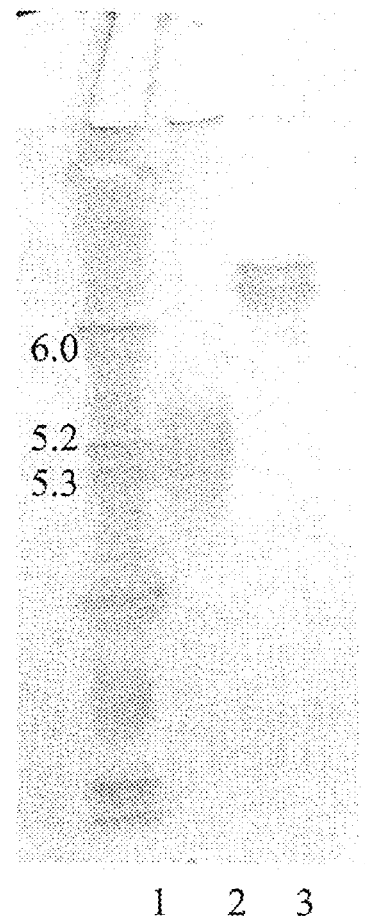
Figure 13A:
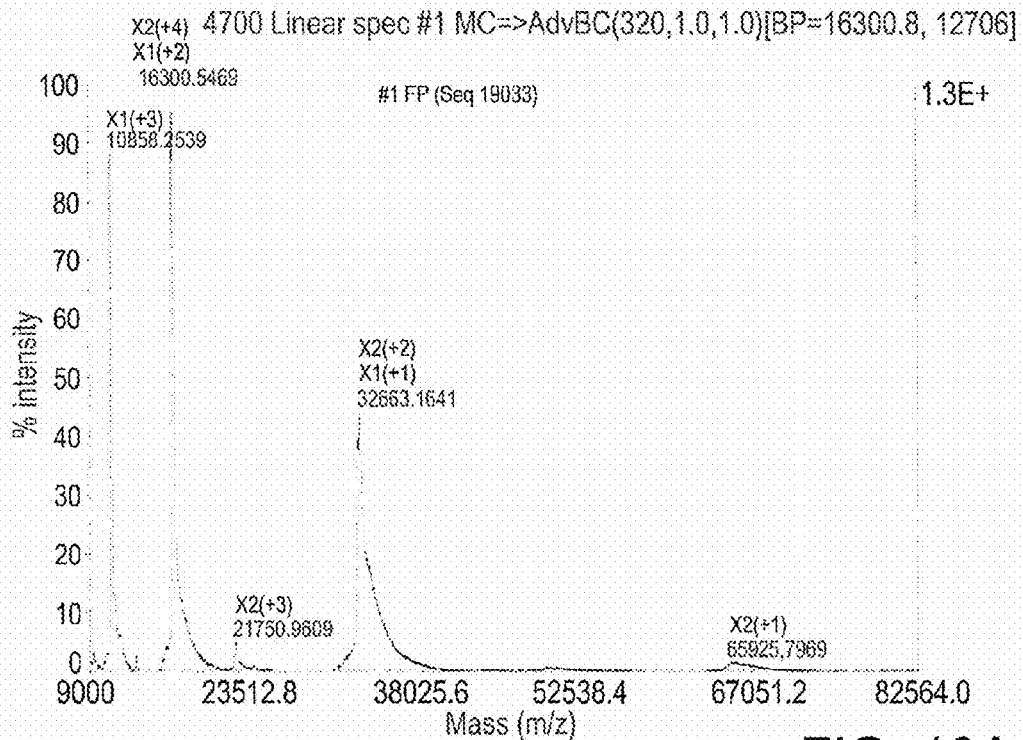
Figure 13B:
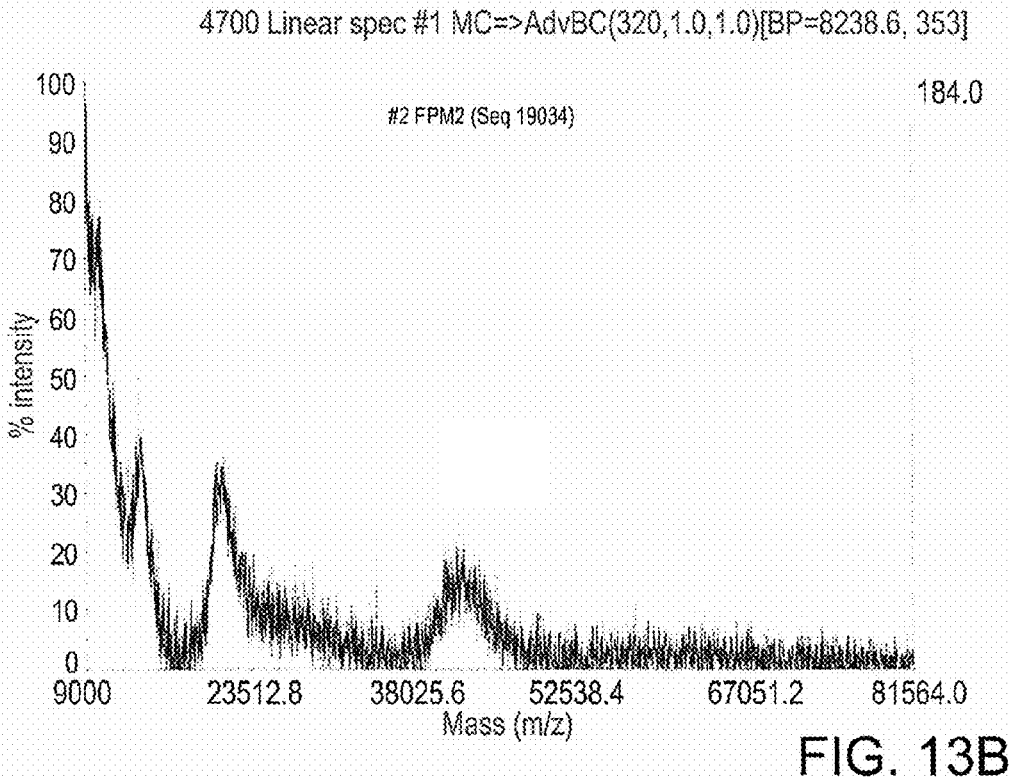
Figure 14A:
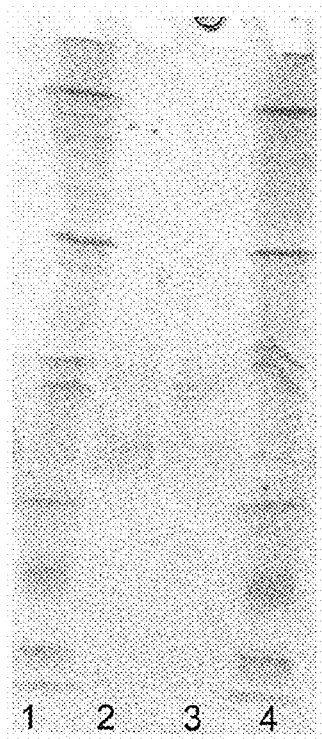
Figure 14B:
Figure 15A:
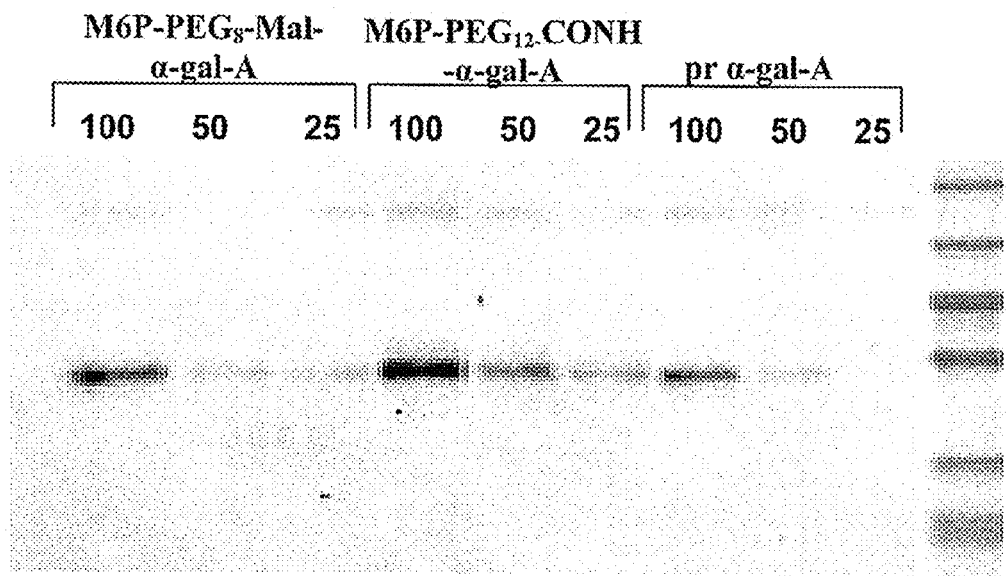
Figure 15B:
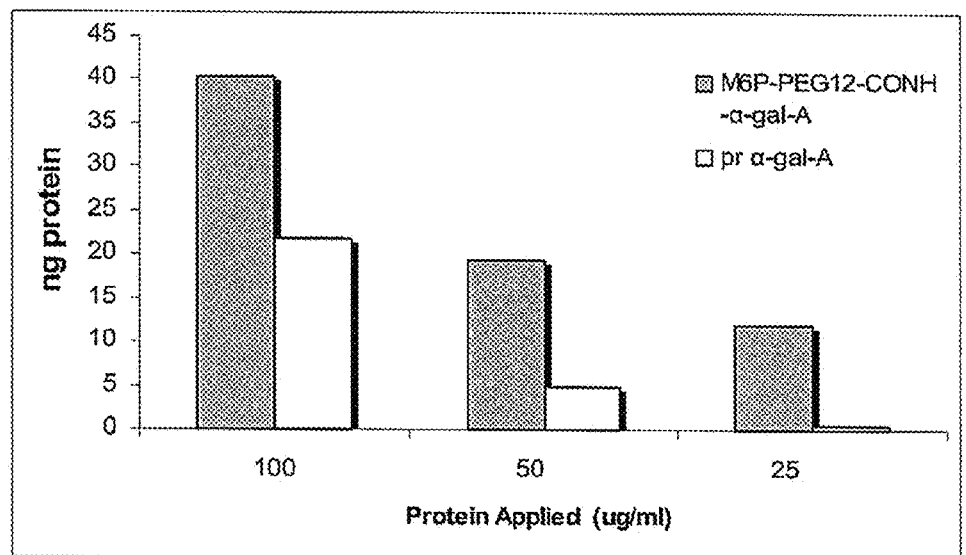
Figure 16A:
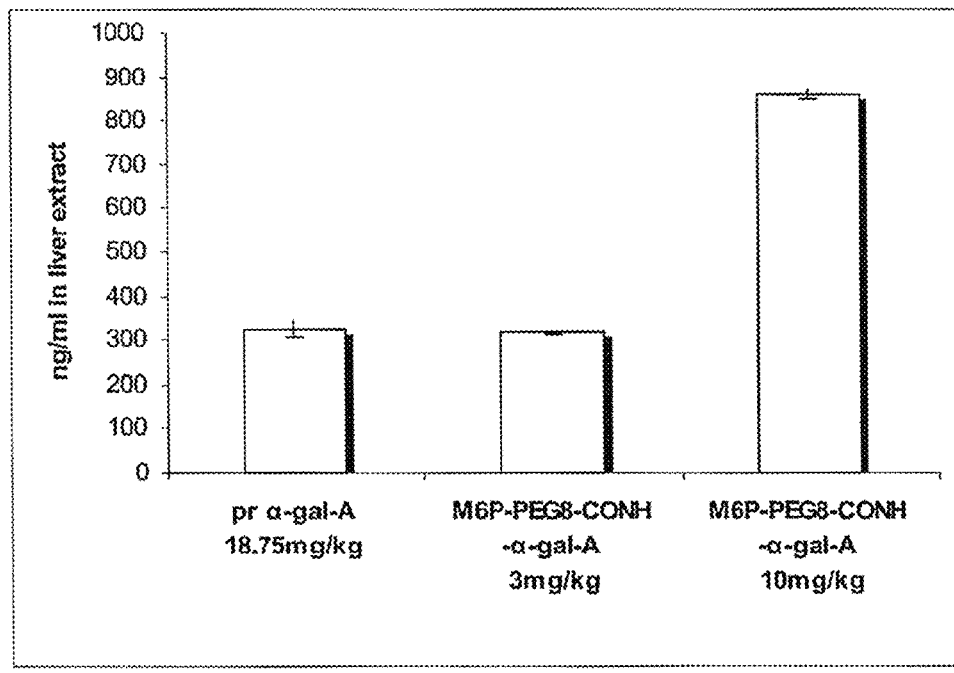
Figure 16B:
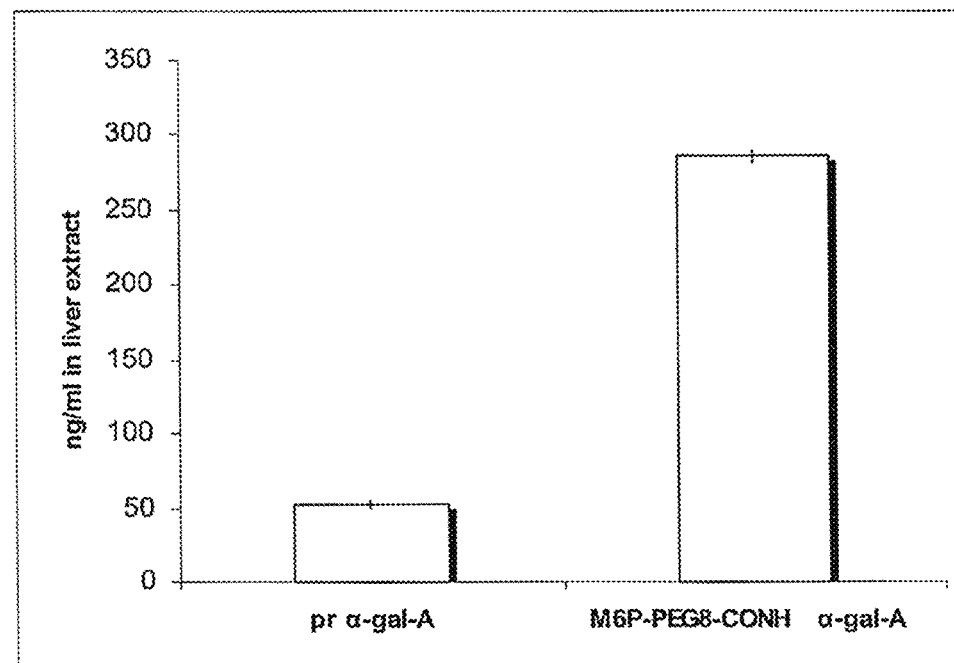
Figure 17:
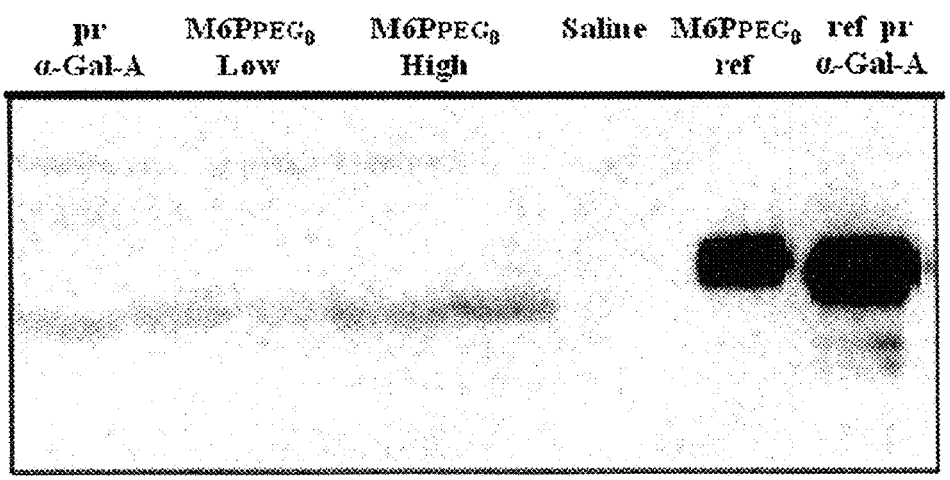
Figure 18A:
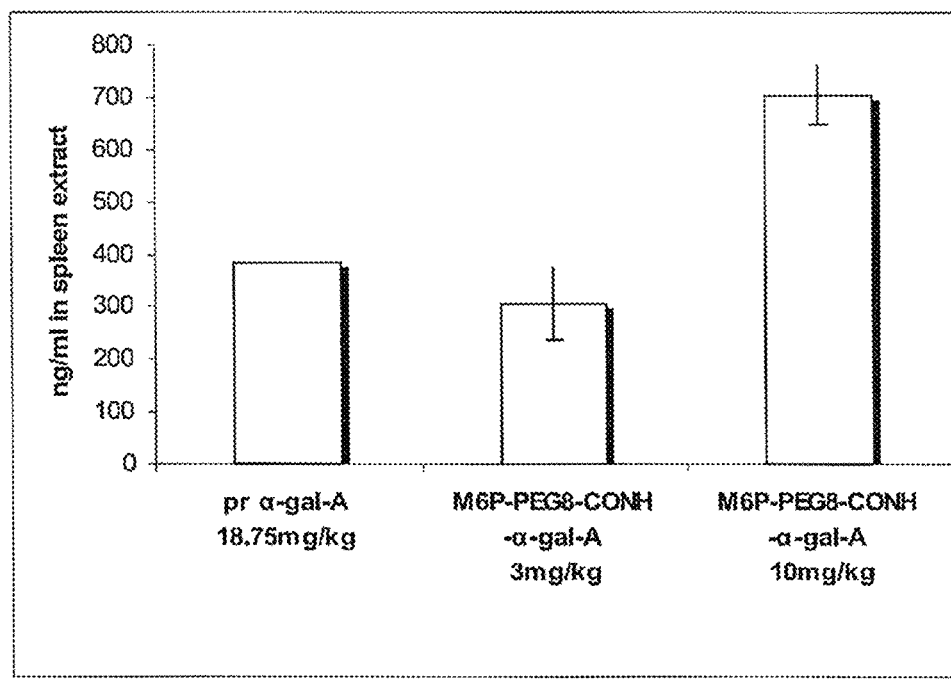
Figure 18B:
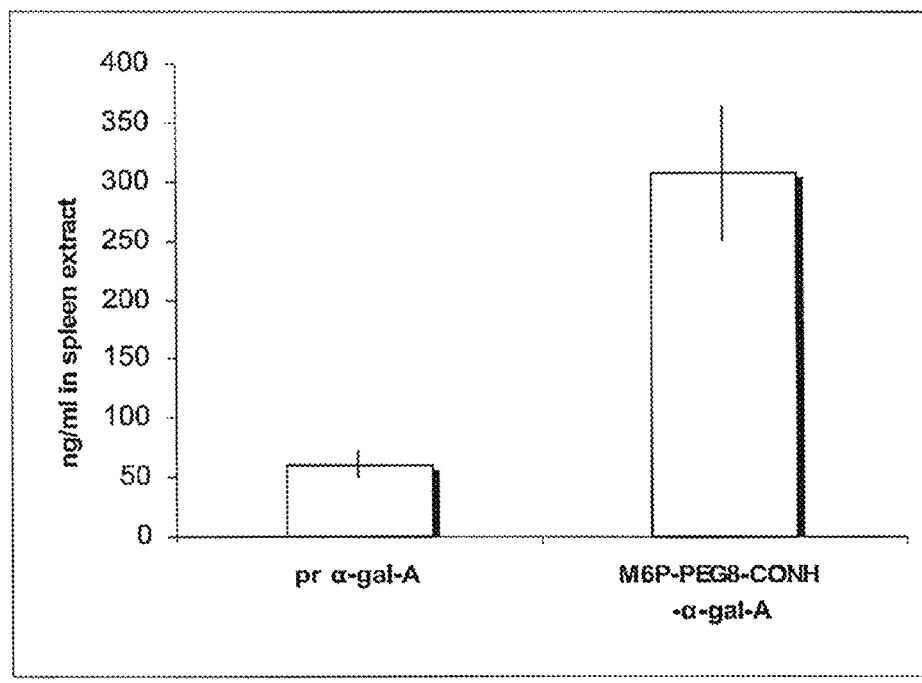
Figure 19A:
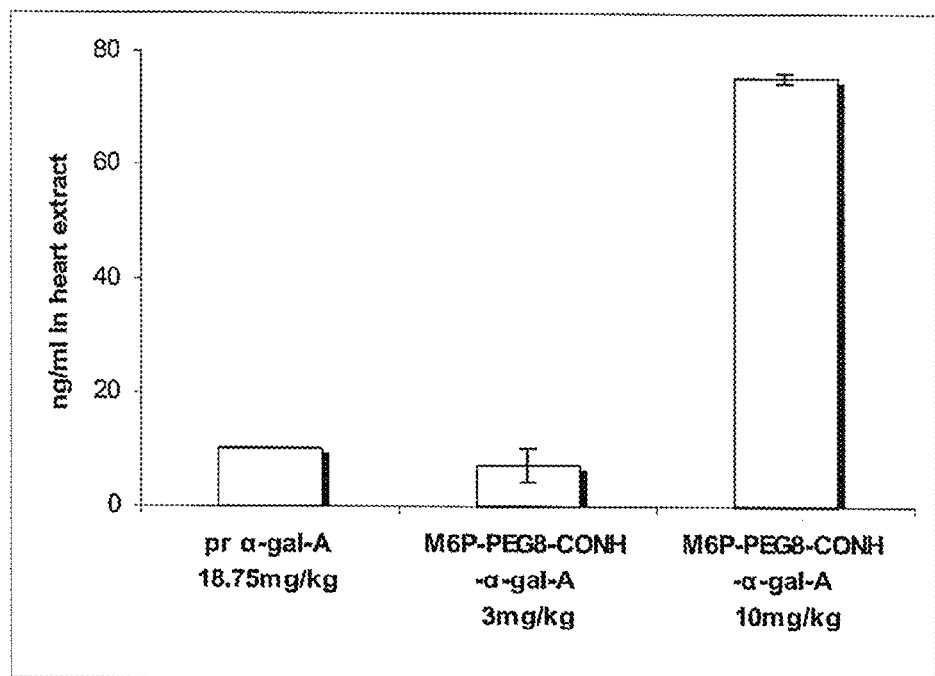
Figure 19B:
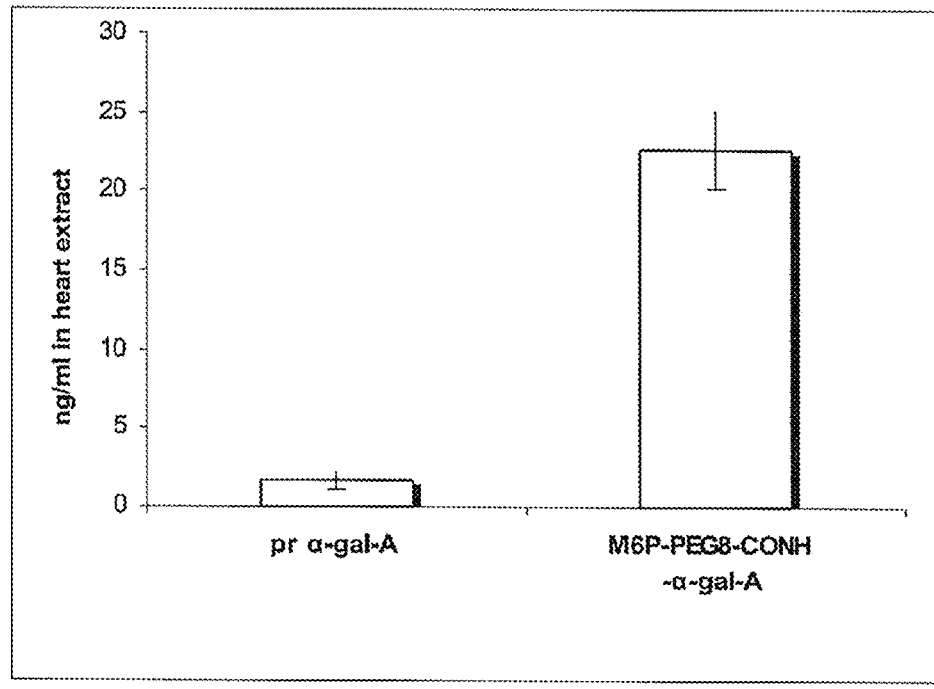
Figure 20A:
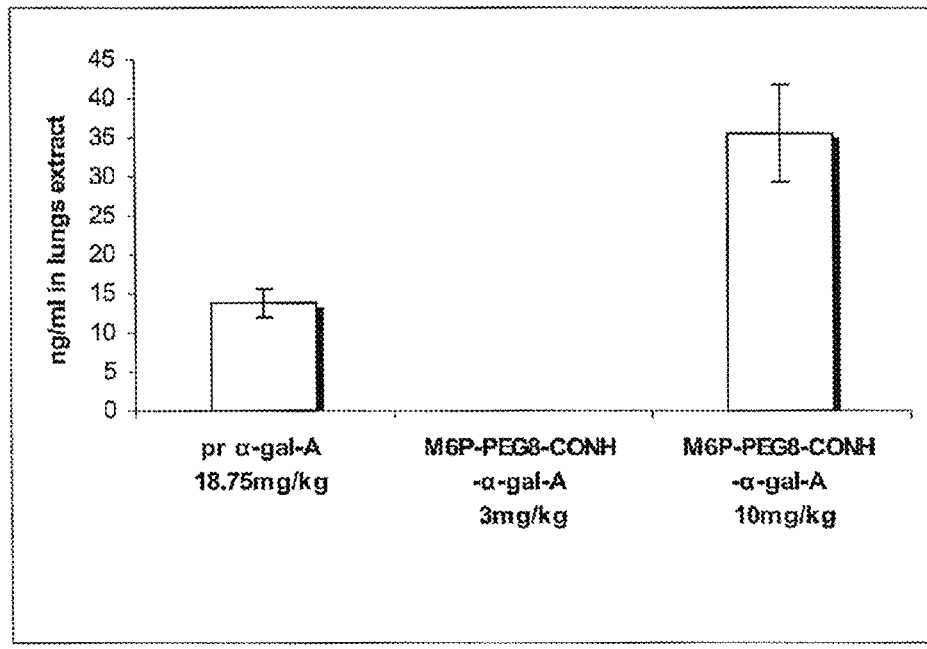
Figure 20B:
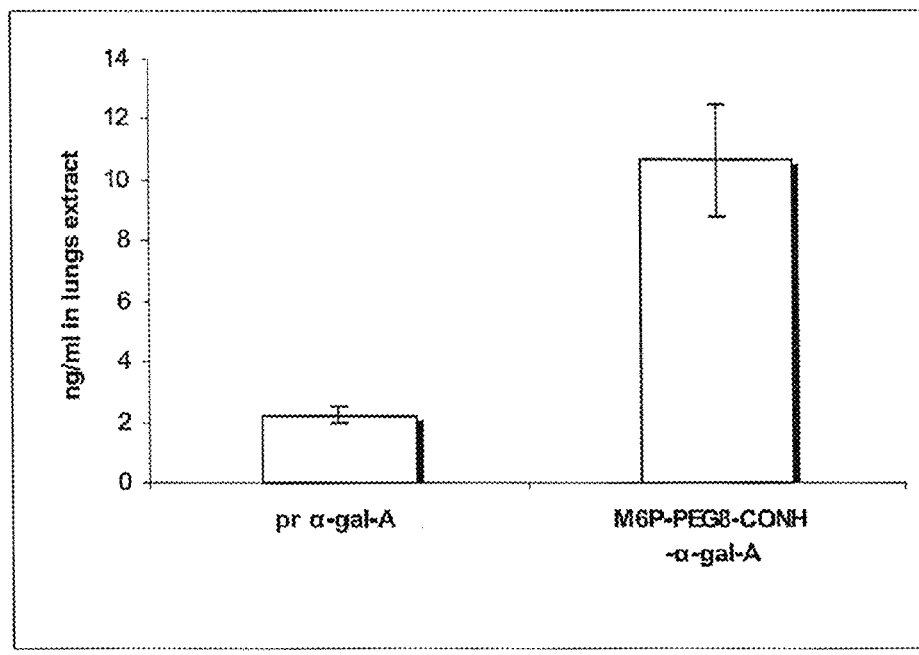
Figure 21A:
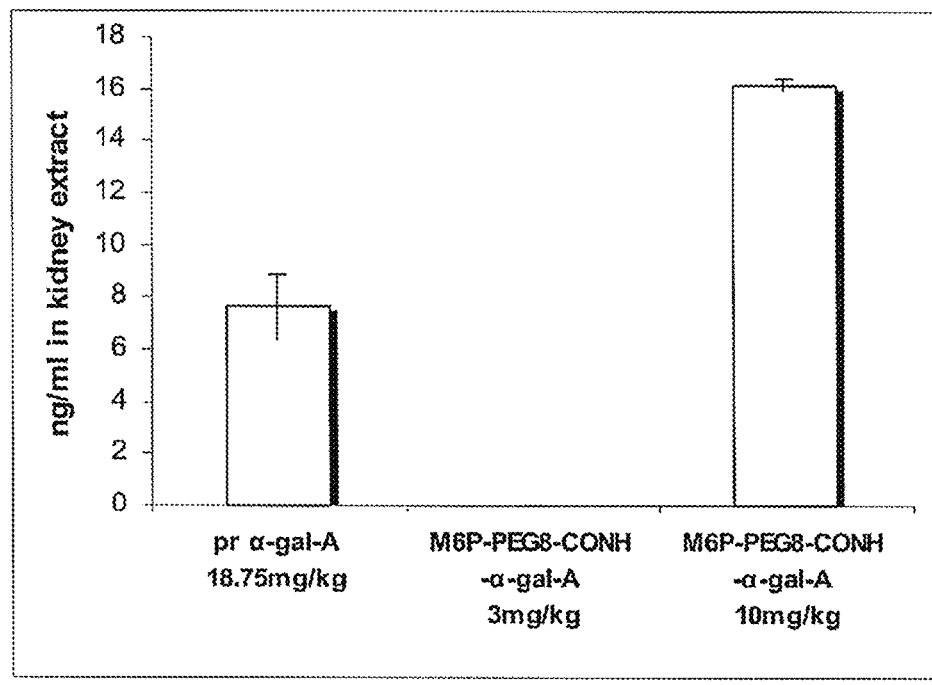
Figure 21B:
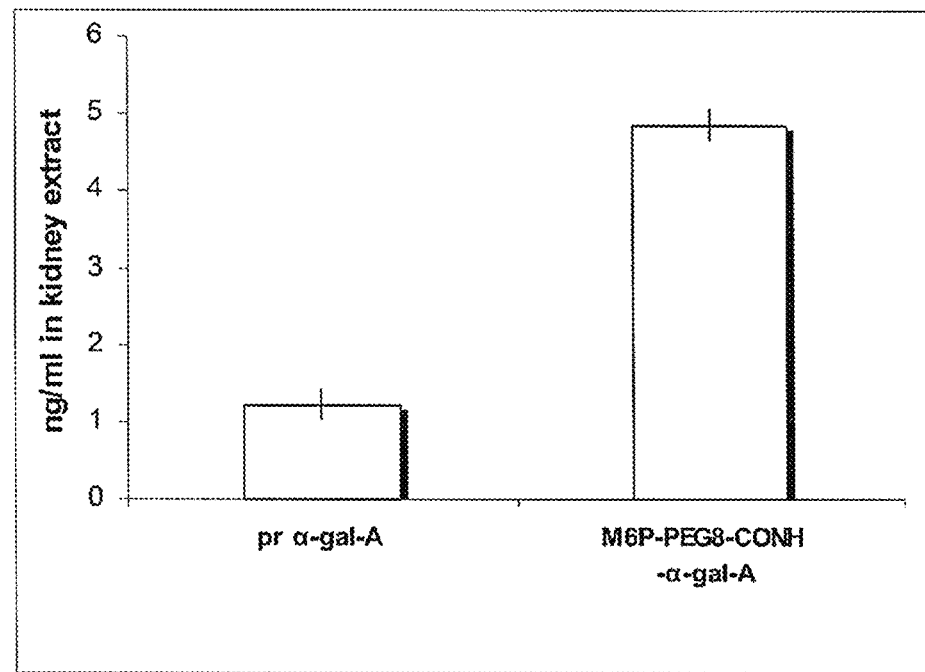
Figure 22A:
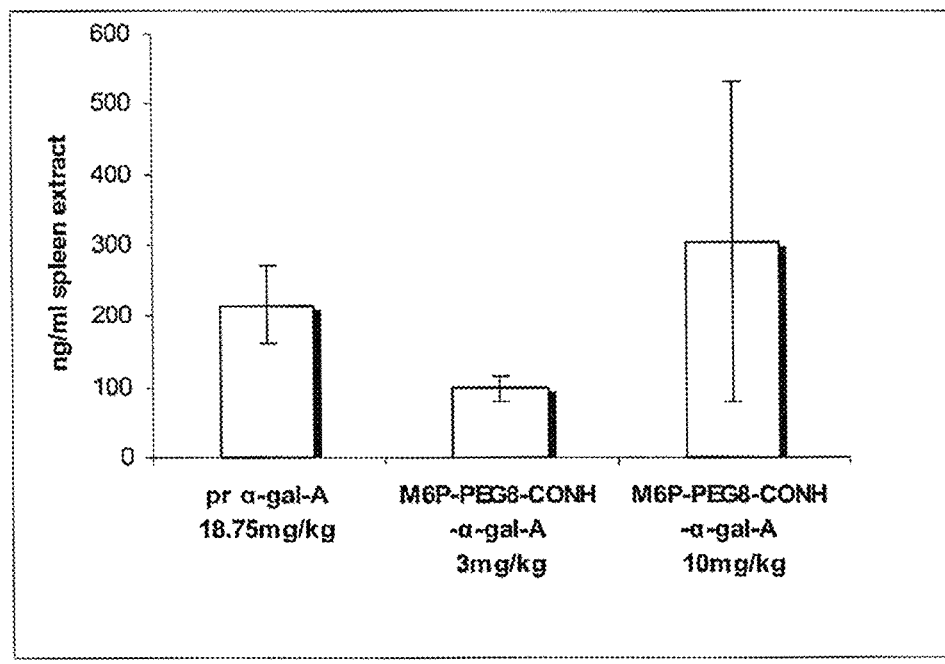
Figure 22B:
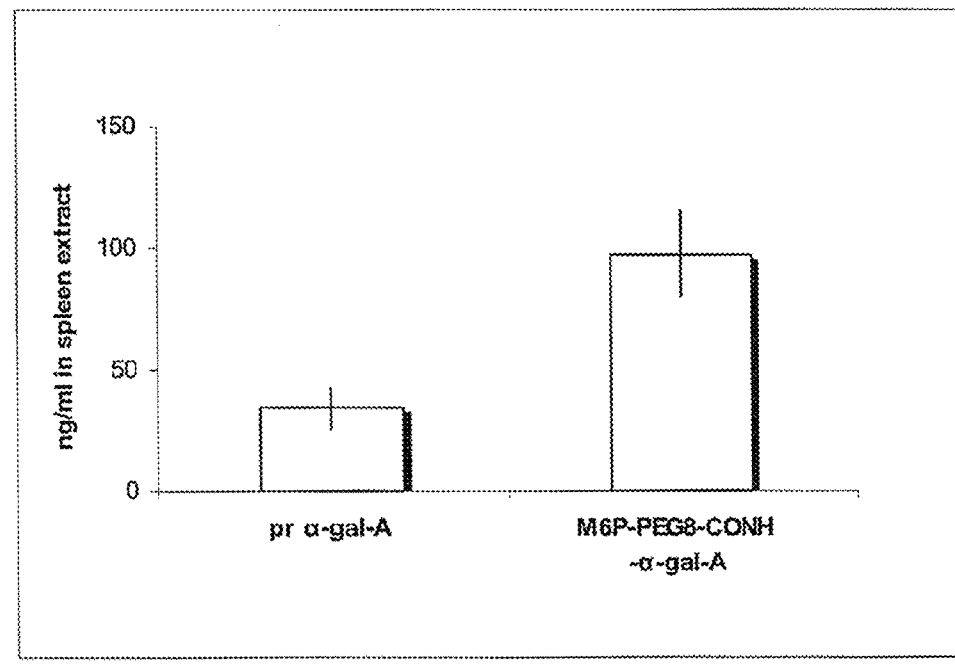
Figure 23:
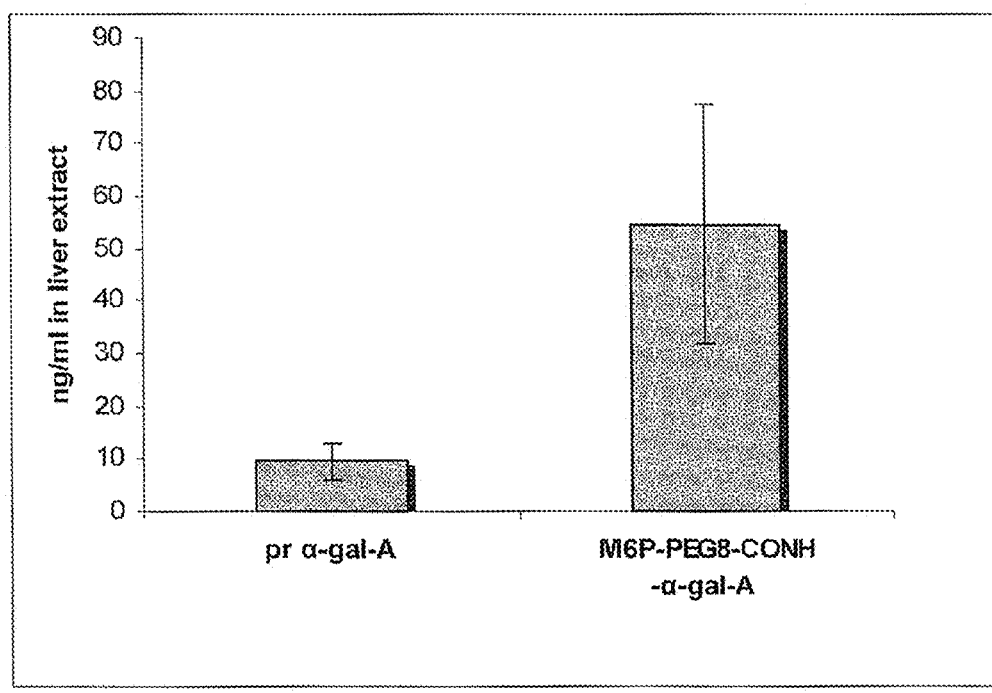
Figure 24:
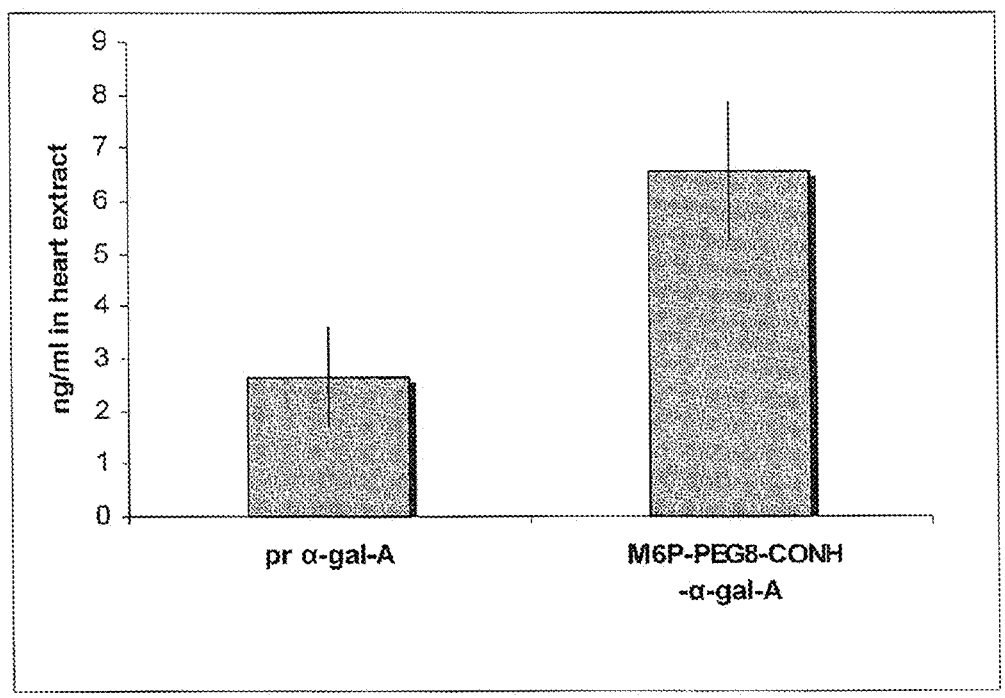
Figure 25:
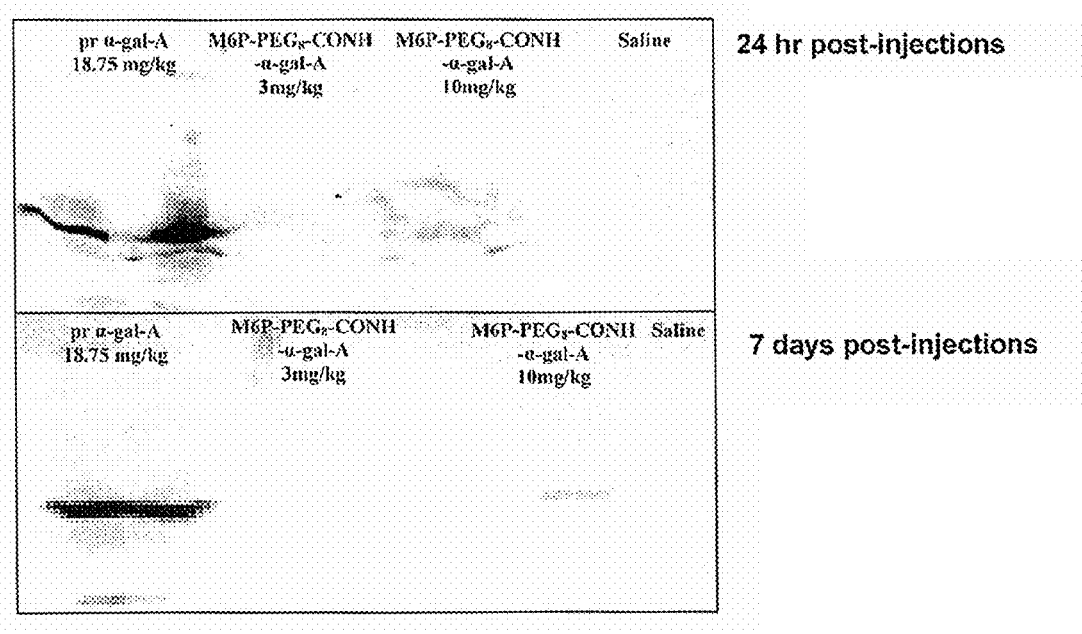
Figure 26A:
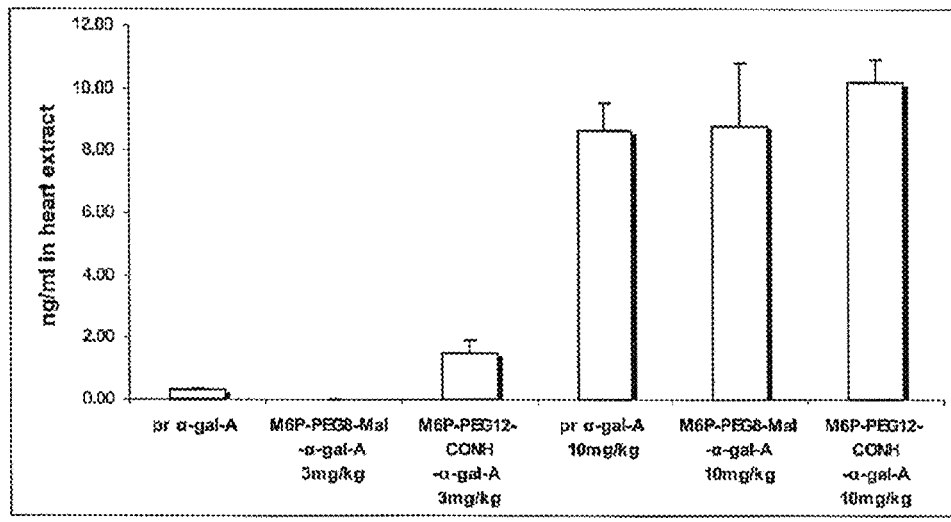
Figure 26B:
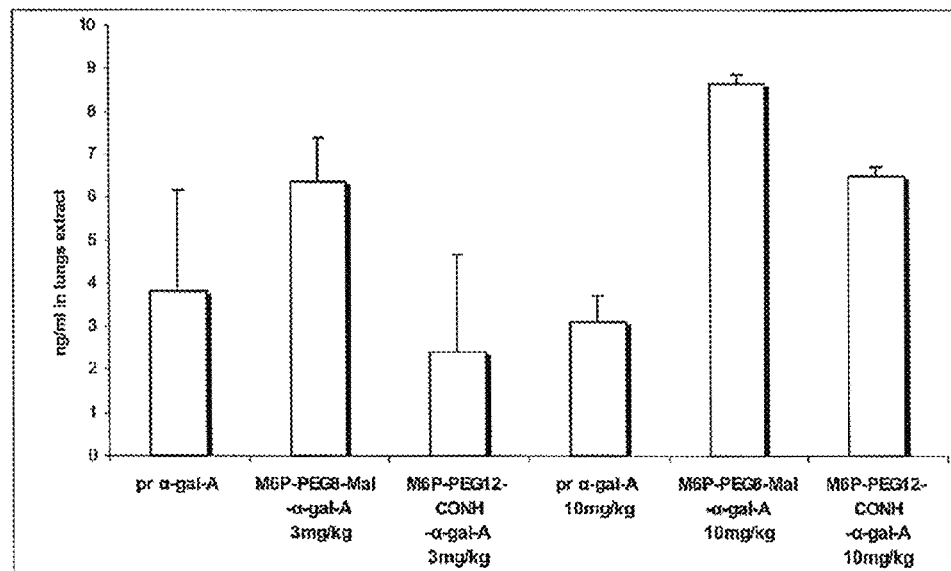
Figure 27A:
Figure 27B:
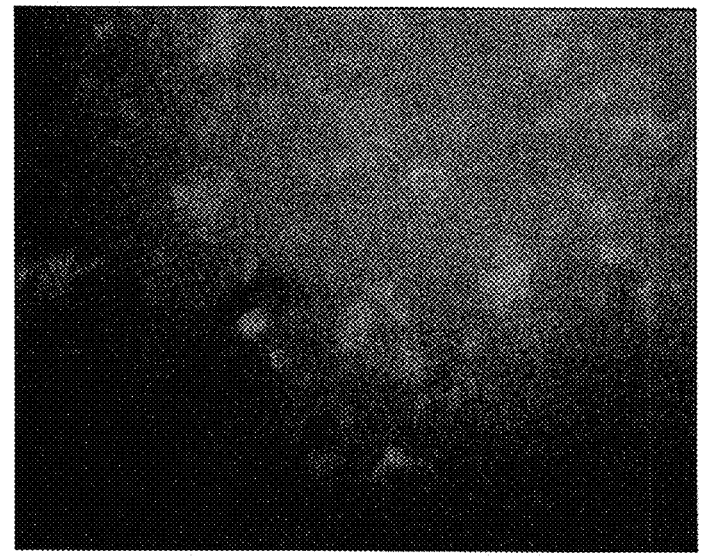
Figure 28:
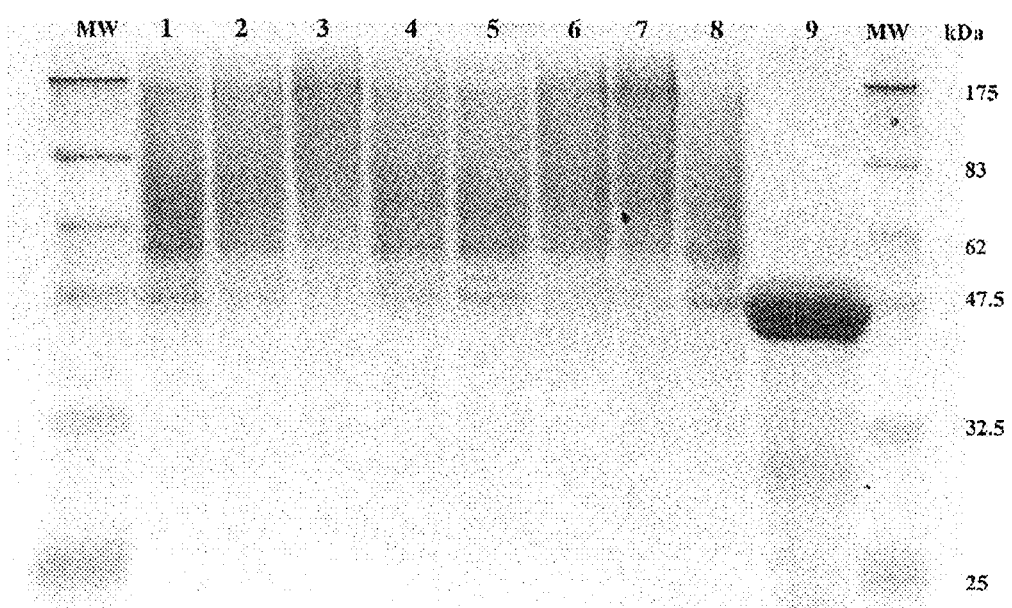

FIGS. 1A-B are depictions of exemplary linear glycosylation reagents comprising M6P and either a carboxylic acid reactive group (FIG. 1A) or a maleimide reactive group (FIG. 1B);

FIGS. 2A-D are depictions of exemplary branched glycosylation reagents comprising 3 M6P units (FIGS. 2A and 2C) or 2 M6P units (FIGS. 2B and 2D);

FIGS. 3A-B are depictions of exemplary linear glycosylation reagents comprising sialic acid and either a maleimide reactive group (FIG. 3A) or a carboxylic acid reactive group activated with N-hydroxysuccinimide (FIG. 3B);

FIG. 4 is a photograph of an SDS-PAGE gel showing molecular weight standards (lanes 1 and 6), plant recombinant α-galactosidase-A (lanes 2 and 4), plant recombinant α-galactosidase-A conjugated with M6P-PEG$_8$-CO$_2$H (lane 3) and plant recombinant α-galactosidase-A conjugated with 750 Da mPEG-CO$_2$H;

FIG. 5 is a photograph of an isoelectric focusing (IEF) gel showing IEF pI standards (lanes 1 and 7), plant recombinant α-galactosidase-A (lanes 2 and 4), plant recombinant α-galactosidase-A with dimethyl sulfoxide (lane 3), plant recombinant α-galactosidase-A conjugated with M6P-PEG$_8$-CO$_2$H (lane 5) and plant recombinant α-galactosidase-A conjugated with 750 Da mPEG-CO$_2$H (lane 6);

FIG. 6 is a photograph of an IEF gel showing IEF pI standards (lanes 1 and 5), plant recombinant α-galactosidase-A (lane 2), plant recombinant α-galactosidase-A conjugated with M6P-PEG$_8$-CO$_2$H (lane 3) and plant recombinant α-galactosidase-A exposed to conjugation reaction conditions in the absence of M6P-PEG$_8$-CO$_2$H (lane 4);

FIG. 7 is a photograph of an SDS-PAGE gel showing molecular weight standards (left lanes 1), plant recombinant α-galactosidase-A (middle lane), and plant recombinant α-galactosidase-A conjugated with M6P-PEG$_8$-CO$_2$H (right lane);

FIGS. 8A-B are MALDI-TOF (Matrix-Assisted Laser Desorption/Ionization-Time Of Flight) mass spectra for plant recombinant α-galactosidase-A (FIG. 8A) and plant recombinant α-galactosidase-A conjugated with M6P-PEG$_8$-CO$_2$H (FIG. 8B) showing a 5.1 kDa increase in the mass of plant recombinant α-galactosidase-A upon conjugation with M6P-PEG$_8$-CO$_2$H;

FIG. 9 is a photograph of an isoelectric focusing (IEF) gel showing IEF pI standards (lane 1), plant recombinant glucocerebrosidase (GCD) (lane 2), and plant recombinant GCD conjugated with M6P-PEG$_8$-CO$_2$H (lane 3);

FIG. 10 is a photograph of an SDS-PAGE gel showing plant recombinant GCD (lane 1), molecular weight standards (lane 2) and plant recombinant GCD conjugated with M6P-PEG$_8$-CO$_2$H (lane 3);

FIGS. 11A-B are MALDI-TOF (Matrix-Assisted Laser Desorption/Ionization-Time Of Flight) mass spectra for plant recombinant GCD (FIG. 8A) and plant recombinant GCD conjugated with M6P-PEG$_8$-CO$_2$H (FIG. 8B) showing a 2,488 Da increase in the mass of plant recombinant GCD upon conjugation with M6P-PEG$_8$-CO$_2$H;

FIGS. 12A-B are photographs of an SDS-PAGE gel (FIG. 12A) and an isoelectric focusing (IEF) gel (FIG. 12B) showing molecular weight standards (FIG. 12A) or IEF pI standards (FIG. 12B) (lanes 1), GFP (green fluorescent protein) conjugated with M6P-PEG$_8$-CO$_2$H (lanes 2) and GFP (lanes 3);

FIGS. 13A-B are MALDI-TOF (Matrix-Assisted Laser Desorption/Ionization-Time Of Flight) mass spectra for GFP (FIG. 8A) and GFP conjugated with M6P-PEG$_8$-CO$_2$H (FIG. 8B) showing an increase in the mass of GFP upon conjugation with M6P-PEG$_8$-CO$_2$H;

FIGS. 14A-B are photographs of an isoelectric focusing (IEF) gel (FIG. 14A) and an SDS-PAGE gel (FIG. 14B) showing IEF pI standards (FIG. 14A, lanes 1 and 4) or molecular weight standards (FIG. 14B, lane 1), plant recombinant α-galactosidase A (lanes 2) and plant recombinant α-galactosidase A thiolated with Traut's reagent and conjugated with M6P-PEG$_8$-maleimide (lanes 3);

FIGS. 15A-B are a photograph of a Western blot (FIG. 15A) and a bar graph (FIG. 15B) showing uptake of plant recombinant α-galactosidase-A, plant recombinant α-galactosidase-A conjugated with M6P-PEG$_8$-maleimide (FIG. 15A only), and plant recombinant α-galactosidase-A conjugated with M6P-PEG$_{12}$-CO$_2$H in Fabry fibroblasts;

FIGS. 16A-B are bar graphs presenting plant recombinant α-galactosidase-A activity in liver tissue samples of mice 24 hours after injection of 18.75 mg/kg plant recombinant α-galactosidase-A, or 3 mg/kg or 10 mg/kg M6P-PEG$_8$-CONH-α-galactosidase-A as absolute concentrations (ng α-galactosidase-A per ml extract) (FIG. 16A) or as concentrations normalized relative to 3 mg/kg of injected α-galactosidase-A (FIG. 16B), wherein each bar represents mean results from tissues of 4 mice;

FIG. 17 is a photograph of a Western blot of α-galactosidase-A in mouse liver tissue samples collected 24 hours after injection of 18.75 mg/kg plant recombinant α-galactosidase-A, or 3 mg/kg (low) or 10 mg/kg (high) M6P-PEG$_8$-CONH-α-galactosidase-A, as well as of 25 ng of reference plant recombinant α-galactosidase-A or MP6-PEG-α-galactosidase-A (M6PPEG$_8$ ref) in saline;

FIGS. 18A-B are bar graphs presenting plant recombinant α-galactosidase-A activity in spleen tissue samples of mice 24 hours after injection of 18.75 mg/kg plant recombinant α-galactosidase-A, or 3 mg/kg or 10 mg/kg M6P-PEG$_8$-CONH-α-galactosidase-A as absolute concentrations (ng α-galactosidase-A per ml extract) (FIG. 18A) or as concentrations normalized relative to 3 mg/kg of injected α-galactosidase-A (FIG. 18B), wherein each bar represents mean results from tissues of 4 mice;

FIGS. 19A-B are bar graphs presenting α-galactosidase-A activity in heart tissue samples of mice 24 hours after injection of 18.75 mg/kg plant recombinant α-galactosidase-A, or 3 mg/kg or 10 mg/kg M6P-PEG$_8$-CONH-α-galactosidase-A as absolute concentrations (ng α-galactosidase-A per ml extract) (FIG. 19A) or as concentrations normalized relative to 3 mg/kg of injected α-galactosidase-A (FIG. 19B), wherein each bar represents mean results from tissues of 4 mice;

FIGS. 20A-B are bar graphs presenting α-galactosidase-A activity in liver tissue samples of mice 24 hours after injection of 18.75 mg/kg plant recombinant α-galactosidase-A, or 3 mg/kg or 10 mg/kg M6P-PEG$_8$-CONHα-galactosidase-A as absolute concentrations (ng α-galactosidase-A per ml extract) (FIG. 20A) or as concentrations normalized relative to 3 mg/kg of injected α-galactosidase-A (FIG. 20B), wherein each bar represents mean results from tissues of 4 mice;

FIGS. 21A-B are bar graphs presenting α-galactosidase-A activity in kidney tissue samples of mice 24 hours after injection of 18.75 mg/kg plant recombinant α-galactosidase-A, or 3 mg/kg or 10 mg/kg M6P-PEG$_8$-CONH-α-galactosidase-A as absolute concentrations (ng α-galactosidase-A per ml extract) (FIG. 21A) or as concentrations normalized relative to 3 mg/kg of injected α-galactosidase-A (FIG. 21B), wherein each bar represents mean results from tissues of 4 mice;

FIGS. 22A-B are bar graphs presenting α-galactosidase-A activity in spleen tissue samples of mice 7 days after injection of 18.75 mg/kg plant recombinant α-galactosidase-A, or 3 mg/kg M6P-PEG$_8$-CONH-α-galactosidase-A as absolute concentrations (ng α-galactosidase-A per ml extract) (FIG. 22A) or as concentrations normalized relative to 3 mg/kg of injected α-galactosidase-A (FIG. 22B), wherein each bar represents mean results from tissues of 4 mice;

FIG. 23 is a bar graph presenting α-galactosidase-A activity in liver tissue samples of mice 7 days after injection of 18.75 mg/kg plant recombinant α-galactosidase-A, or 3 mg/kg M6P-PEG$_8$-CONH-α-galactosidase-A as concentrations normalized relative to 3 mg/kg of injected α-galactosidase-A;

FIG. 24 is a bar graph presenting α-galactosidase-A activity in heart tissue samples of mice 7 days after injection of 18.75 mg/kg plant recombinant α-galactosidase-A, or 3 mg/kg M6P-PEG$_8$-CONH-α-galactosidase-A as concentrations normalized relative to 3 mg/kg of injected α-galactosidase-A;

FIG. 25 shows photographs of Western blots of α-galactosidase-A in plasma samples 24 hours and 7 days after injection of 18.75 mg/kg plant recombinant α-galactosidase-A, 3 mg/kg or 10 mg/kg M6P-PEG$_8$-CONH-α-galactosidase-A, or saline;

FIGS. 26A-B are bar graphs presenting α-galactosidase-A activity in heart (FIG. 26A) and lung (FIG. 26B) tissue samples of mice 24 hours days after injection of 3 mg/kg or 10 mg/kg of plant recombinant α-galactosidase-A, M6P-PEG$_{12}$-CONH-α-galactosidase-A or M6P-PEG$_8$-maleimide-α-galactosidase-A as concentrations normalized relative to 3 mg/kg of injected α-galactosidase-A;

FIGS. 27A-B are fluorescent microscopy photographs showing uptake of 1 μM GFP (FIG. 27A) or M6P-PEG-CONH-GFP (FIG. 27B) into Fabry fibroblasts after 24 hours of incubation; and FIG. 28 is a photograph of an SDS-PAGE gel showing molecular weight standards (MW), and plant recombinant α-galactosidase conjugated with 100 molar equivalents of 5 kDa mPEG-COOH and either 100 (lanes 1, 4, 5 and 8), 130 (lanes 2 and 6) or 200 (lanes 3 and 7) equivalents of each of ECD and sulfo-N-hydroxysuccinimide.

DESCRIPTION OF SPECIFIC EMBODIMENTS
OF THE INVENTION

The present invention generally relates to glycosylation reagents which can be used in the preparation of modified biomolecules with improved performance and to modified biomolecules formed thereby. The modified biomolecules of the present embodiments are conjugates composed of the biomolecule and a saccharide moiety, being covalently linked therebetween via a linker, preferably being a non-hydrophobic, non-saccharide linker. The modification of the biomolecule (e.g., a protein) is aimed at increasing the serum half-life of a biomolecule, or facilitating the interaction of the resulting conjugate with carbohydrate-specific receptors and thus enables the recognition and further trafficking of the modified biomolecule to target tissues, cells or organelles and/or its uptake across cellular membranes via interaction with the specific membranal receptor.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have designed and successfully prepared and practiced a glycosylation reagent for forming a conjugate that comprises a biomolecule (e.g., a protein), a saccharide moiety and a linker linking the biomolecule and the saccharide moiety.

As used herein, the phrase "glycosylation reagent" describes a compound that is capable of coupling (conjugating) a saccharide moiety to another compound, herein a biomolecule. This phrase is also referred to herein interchangeably as a saccharide derivatization agent. When the saccharide moiety is a mannose-6-phosphate (M6P), the phrase M6Pylation reagent is used interchangeably to described the glycosylation reagent.

The glycosylation reagents presented herein are based on a saccharide moiety linked to a non-hydrophobic linker.

As used herein, the phrase "non-hydrophobic" describes a compound or moiety that is substantially water-soluble. A detailed description of the linker moiety is provided hereinafter.

These reagents, referred to herein also as "compounds", can be collectively represented by the following general Formula:

X-A-Z wherein:

X is a saccharide moiety, such as, for example, a monosaccharide;

A is a non-hydrophobic linker, such as, for example, a poly(alkylene glycol) chain at least 18 atoms in length; and Z is a reactive group that forms a part of the linker.

As used herein, the phrase "reactive group" describes a chemical group that is capable of undergoing a chemical reaction that typically leads to a bond formation. The bond, according to the present embodiments, is preferably a covalent bond. Chemical reactions that lead to a bond formation include, for example, nucleophilic and electrophilic substitutions, nucleophilic and electrophilic addition reactions, alkylations, addition-elimination reactions, cycloaddition reactions, rearrangement reactions and any other known organic reactions that involve a functional group, as well as combinations thereof.

The reactive group is selected suitable for undergoing a chemical reaction that leads to a bond formation with a complementary functionality in the biomolecule.

The reactive group may optionally comprise a non-reactive portion (e.g., an alkyl) which may serve, for example, to attach a reactive portion of the reactive group to the A moiety.

The linker, as described herein, is represented by -A-Z in the above formula.

As used herein, the term "saccharide moiety" describes a moiety, as defined herein, that contains one or more saccharide units.

As used herein the term "moiety" describes a major portion of a first molecule which is covalently linked to another molecule and which retains its main structural features and/or activity. Thus, a "moiety" refers to a part of a molecule formed by conjugating the aforementioned first molecule to one or more other molecules, and represents that portion of the first molecule that is present in the conjugation product. For example, a carboxylic acid moiety is the R—C(=O)— portion of a R—C(=O)OH carboxylic acid molecule formed upon conjugating the latter to an amine group in a second molecule, to thereby obtain an amide. In another example, an alkyl moiety is the portion of an alkyl halide molecule formed upon a nucleophilic reaction between the alkyl halide and an electrophilic molecule.

Accordingly, a "saccharide moiety" is that portion of a saccharide molecule formed upon conjugating a second molecule thereto.

In exemplary embodiments of the invention, the saccharide moiety contains one saccharide unit and the saccharide unit is a monosaccharide.

The term "monosaccharide", as used herein and is well known in the art, refers to a simple form of a sugar that consists of a single saccharide unit which cannot be further decomposed to smaller saccharide building blocks or moieties. Common examples of monosaccharides include glucose (dextrose), fructose, galactose, mannose, and ribose. Monosaccharides can be classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms.

The above monosaccharides encompass both D- and L-monosaccharides.

In one embodiment, the monosaccharide is a hexose or a hexose derivative. In some embodiments, the hexose is a D-hexose.

In an alternative embodiment, the hexose is a L-hexose.

Alternatively, the monosaccharide can be a monosaccharide derivative, in which the saccharide unit comprises one or more substituents other than hydroxyls. Such derivatives can be, but are not limited to, ethers, esters, amides, acids, phosphates and amines. Amine derivatives include, for example, glucosamine, galactosamine, fructosamine and mannosamine. Amide derivatives include, for example, N-acetylated amine derivatives of saccharides (e.g., N-acetylglucosamine, N-acetylgalactosamine).

Exemplary monosaccharide derivatives include mannose-6-phosphate (M6P), a phosphate derivative, and N-acetylneuraminic acid (a sialic acid), an acid and amide derivative.

Monosaccharides of particular interest include mannose and M6P, interacting specifically with mannose receptors and CI-MPR (cation-independent mannose phosphate receptor) and/or CD-MPR (cation-dependent mannose phosphate receptor), respectively. These monosaccharides are found in natural glycosides on the surface of a variety of lysosomal enzymes, enabling their trafficking to lysosomes, where they exert their specific hydrolytic activity. Other monosaccharides of particular interest are sialic acids, such as N-acetylneuraminic acid.

As used herein, the phrase "sialic acid" describes an N- or O-derivative of neuraminic acid (in which either the N atom or the O atom of the neuraminic acid are derivatized). N-acetylneuraminic acid is an exemplary sialic acid.

As used herein, the term "M6P" describes the naturally-occurring D-mannose-6-phosphate, as well as the non-naturally occurring L-mannose-6-phosphate, although the first is preferred.

In some embodiments, the linker is attached to the saccharide moiety at the anomeric carbon (e.g., C-1 in mannose and M6P, C-2 in sialic acid) of the saccharide moiety through an ether bond. The anomeric carbon of monosaccharides is typically in the form of acyclic hemiketal or hemiacetal. Thus, an ether bond to an anomeric carbon describes an alkyl group (e.g., being a part of the linker) bound to an oxygen atom which is bound to the anomeric carbon, thereby forming an acetal or ketal.

In some embodiments, the linker is attached to the anomeric carbon via an α configuration, which is an axial conformation in typical D-hexoses (including D-mannose and M6P).

In many naturally-occurring glycosylated proteins (e.g., M6P-protein conjugates), the terminal saccharide is linked to the penultimate saccharide via an α configuration. Conjugation of saccharide moieties corresponding to such terminal saccharides to a linker of a glycosylation reagent via the natural α configuration enables higher affinity and recognition between the conjugate formed from the glycosylation reagent and the target receptors.

In an exemplary embodiment, the linker is attached via an α configuration to D-mannose, M6P or sialic acid (e.g., N-acetylneuraminic acid). Exemplary glycosylating reagents comprising an M6P saccharide moiety attached to a linker via an α configuration are depicted in FIGS. 1A-B and 2A-D, as well as in Scheme 1 hereinbelow. Exemplary glycosylating reagents comprising a N-neuraminic acid saccharide moiety attached to a linker via an α configuration are depicted in FIGS. 3A-B.

The linker in the compounds described herein is aimed at linking the saccharide moiety to a target biomolecule and hence is preferably selected so as to mimic the structure and chemical characteristics of natural glycosylation groups, composed of oligosaccharide chains.

The linker is characterized as having a non-hydrophobic nature due to the poor functionality exhibited by hydrophobic linkers. Thus, for example, hydrocarbon chains are not suitable since they are of hydrophobic nature and are prone to hydrophobic folding, diminishing the exposure of the saccharides to the relevant receptors and even preventing interaction between the biomolecule and such receptors.

Optionally, the non-hydrophobic linker is amphiphilic. As used herein, the term "amphiphilic" describes a compound or moiety that is substantially soluble in both water and a water-immiscible solvent. Amphiphilic linkers can thus avoid folding in both an aqueous and non-aqueous (e.g., lipid) surroundings, thereby maintaining maximal exposure of the saccharide moiety of the formed conjugate to the relevant receptors.

In some embodiments, the linker is a non-saccharide linker.

A saccharide linker attached to the saccharide moiety would result in a disaccharide, trisaccharide or oligosaccharide moiety. Such groups would closely mimic natural glycosylation groups, as discussed hereinabove, but would be sensitive to enzymes which hydrolyze natural glycosylation groups. A non-saccharide linker is less prone to hydrolysis, and hence, a glycosylation reagent with a non-saccharide linker provides a longer lasting glycosylated biomolecule in a biological environment.

In some embodiments, the linker comprises a poly(alkylene glycol) chain.

The phrase "poly(alkylene glycol)", as used herein, encompasses a family of polyether polymers which share the following general formula: $-O-[(CH_2)_m-O-]n-$, wherein m represents the number of methylene groups present in each alkylene glycol unit, and n represents the number of repeating units, and therefore represents the size or length of the polymer. For example, when m=2, the polymer is referred to as a polyethylene glycol, and when m=3, the polymer is referred to as a polypropylene glycol.

In some embodiments, m is an integer greater than 1 (e.g., m=2, 3, 4, etc.).

Optionally, m varies among the units of the poly(alkylene glycol) chain. For example, a poly(alkylene glycol) chain may comprise both ethylene glycol (m=2) and propylene glycol (m=3) units linked together.

The phrase "poly(alkylene glycol)" also encompasses analogs thereof, in which the oxygen atom is replaced by another heteroatom such as, for example, S, —NH— and the like. This term further encompasses derivatives of the above, in which one or more of the methylene groups composing the polymer are substituted. Exemplary substituents on the methylene groups include, but are not limited to, alkyl, cycloalkyl, alkoxy, hydroxy, thiol, amine, halo, oxo, carbonyl, carboxylate, carbamate, and the like.

Thus, the phrase "alkylene glycol unit", as used herein, encompasses a $-(CH_2)m-O-$ group or an analog thereof, as described hereinabove, which forms the backbone chain of the poly(alkylene glycol), wherein the $(CH_2)m$ (or analog thereof) is bound to a heteroatom belonging to another alkylene glycol unit or to a saccharide moiety (in cases of a terminal unit), and the O (or heteroatom analog thereof) is bound to the $(CH_2)m$ (or analog thereof) of another alkylene glycol unit, to a reactive group (also referred to herein as "Z"), or to another group at the end of another poly(alkylene glycol) chain.

It is to be noted that a heteroatom linking an alkylene glycol unit to the reactive group Z may optionally be considered as being shared by the alkylene glycol and Z (i.e., belonging to both groups).

An alkylene glycol unit may be branched, such that it is linked to 3 or more neighboring alkylene glycol units, wherein each of the 3 or more neighboring alkylene glycol units are part of a poly(alkylene glycol) chain. Such a branched alkylene glycol unit is linked via the heteroatom thereof to one neighboring alkylene glycol unit, and heteroatoms of the remaining neighboring alkylene glycol units are each linked to a carbon atom of the branched alkylene glycol unit. In addition, a heteroatom (e.g., nitrogen) may bind more than one carbon atom of an alkylene glycol unit of which it is part, thereby forming a branched alkylene glycol unit (e.g., $[-CH_2)m]_2N-$ and the like).

In exemplary embodiments, at least 50% of alkylene glycol units are identical, e.g., they comprise the same heteroatoms and the same m values as one another. Optionally, at least 70%, optionally at least 90%, and optionally 100% of the alkylene glycol units are identical. In exemplary embodiments, the heteroatoms bound to the identical alkylene glycol units are oxygen atoms. In further exemplary embodiments, m is 2 for the identical units.

The length of the linker chain is preferably selected so as to conform to the length of the natural glycosyl chains of proteins. Thus, short-chained linkers, such as, for example, poly (ethylene glycol) including up to 4 ethylene glycol units (which form a chain of up to 12 atoms in length), are not suitable for enhancing the interaction between a biomolecule to carbohydrate-specific receptors, such as the CI-MPR.

Thus, in some embodiments, the linker is a poly(alkylene glycol) that comprises a chain of at least 18 atoms in length. Accordingly, in an exemplary embodiment, the linker comprises at least 6 ethylene glycol units. Thus, the poly(alkylene glycol) can comprise 6, 7, 8, 9, 10, 11, 12, 13, 14, 15, 16, 17, 18, 19, 20 and so on, units, as defined hereinabove.

Preferably, the poly(alkylene glycol) comprises a chain of 18 to 170 atoms. In some embodiments, the poly(alkylene glycol) comprises a chain of 18 to 100 atoms. In some embodiments, the poly(alkylene glycol) comprises a chain of 18 to 60 atoms. In some embodiments, the poly(alkylene glycol) comprises a chain of 18 to 36 atoms. In some embodiments, the poly(alkylene glycol) comprises a chain of 24 to 36 atoms.

The length of a poly(alkylene glycol) chain, in atoms, is equal to n(m+1), as these variables are defined hereinabove (if m varies among the units in the poly(alkylene glycol), the value n(m+1) is based on the average value of m).

In one embodiment, the linker is a single, straight chain linker, preferably being polyethylene glycol (PEG).

As used herein, the term "poly(ethylene glycol)" describes a poly(alkylene glycol) as defined hereinabove, wherein at least 50%, at least 70%, at least 90%, and preferably 100%, of the alkylene glycol units are —$CH_2CH_2$—O—. Similarly, the phrase "ethylene glycol units" is defined herein as units of —$CH_2CH_2$O—.

The linker may also include branched chains, also known as multi-antennary. In such branched linkers, each branched chain is linked to a saccharide moiety, and the variable X in the above formula represents all saccharide moieties bound to the linker. Bi-, tri- or multi-antennary linkers may be used to enhance the binding to specific receptors.

Glysosylation reagents having a branched linker can therefore be represented by the general formula:

(X)$_n$-A-Z wherein X and Z are as described herein, A is a branched linker as defined herein and n corresponds to the number of branched chains of the branched linker.

It is to be understood that the length, in atoms, of a poly(alkylene glycol) or a linker, refers to the number of atoms forming a linear chain between the saccharide moiety and the reactive group (e.g., refers to the variable A in the formula hereinabove). Thus, a branched linker which links a plurality of saccharide moieties to a reactive group will be characterized by a plurality of lengths, one length for each saccharide moiety, whereby the length of each linker is as defined herein (e.g., at least 18 atoms in length).

A branched linker allows the attachment of a plurality of saccharide moieties via a single site on a biomolecule. Exemplary glycosylating reagents comprising a branched linker are depicted in FIGS. 2A-D. The use of a branched linker is especially beneficial in case the biomolecule exhibits a limited number of potential anchoring positions or in case the attachment of a small number of linkers per biomolecule is desired. A branched linker glycosylation reagent may also be used to mimic the structure of natural branched oligosaccharide moieties (e.g., in glycosylated proteins) which comprise two or more terminal saccharides (e.g., M6P) per oligosaccharide moiety. Such branched oligosaccharide moieties may be characterized by a higher affinity to a receptor of the terminal saccharide.

In an optional embodiment, the linker comprises at least two chemical moieties which are covalently linked to one another. For example, the linker may comprise two or more poly(alkylene glycol) moieties which have been covalently linked to one another so as to form a longer linear poly(alkylene glycol) moiety from shorter poly(alkylene glycol) moieties and/or so as to form a branched poly(alkylene glycol) moiety from linear poly(alkylene glycol) moieties.

The chemical moieties linked to one another may be the same or different from one another.

The chemical nature of the linkage between such moieties depends on the reactive group(s) present within the poly(alkylene glycol) moieties, and can be, for example, an ester, an amide, an amine, an ether, a thioether, a disulfide, a sulfonate, a sulfonyl, a sulfinyl, a phosphate, a phosphonate, a phosphinyl, a carbamate, a thiocarbamate, a urea, a thiourea, a thiocarboxylate, a hydrazine, azo, a guanidino group, a guanyl and the like, all being linking groups linking the two poly(alkylene glycol) moieties.

An elongated linker may be prepared from two linker moieties (e.g., poly(alkylene glycol) moieties, as defined herein), wherein one linker moiety comprises a first reactive group (as defined herein) and a second reactive group, and the other linker moiety comprises a third reactive group, wherein the second and third reactive groups on the moieties can be reacted with each other so as to form a linkage, as described hereinabove. For example, the second and third reactive groups may be a carboxylate and an amine, such that they react to form an amide linkage.

The elongated linker thus formed comprises the first reactive group (the Z moiety referred to herein).

Similarly, an elongated linker may be prepared from more than two linker moieties, using the two moieties described hereinabove in combination with one or more moieties having two reactive groups.

Optionally, the elongated linker is prepared with an attached saccharide moiety. In such a case, the aforementioned linker moiety comprising the third reactive group is attached to a saccharide moiety.

Alternatively, the elongated linker is prepared without an attached saccharide moiety. The saccharide moiety is then attached to the elongated linker in order to obtain the glycosylating reagent. In such cases, the linker moiety which is aimed at being attached to the saccharide moiety (e.g., the aforementioned linker moiety comprising the third reactive group) can be protected in order to avoid a reaction of this portion of the polymer.

A branched linker may be prepared as described hereinabove for an elongated linker, except that at least one linker moiety has additional reactive groups capable of forming linkages.

For example, a moiety comprising a first reactive group and/or a moiety attached to a saccharide (or capable of being attached to a saccharide moiety) may further comprise two or more additional reactive groups, rather than one. Thus, for example, a linker moiety comprising a first reactive group and two or more carboxylate groups may be attached to an amine group of each of two or more linker moieties attached to a saccharide moiety, thereby forming an elongated linker with a first reactive group and a plurality of amide linkage, which is attached to a plurality of saccharide moieties.

Alternatively, one or more branching moieties may comprise three or more reactive groups. For example, a linker moiety comprising a first reactive group and a second reactive group is attached to a branching moiety by reacting the second branching moiety with a reactive group on the branching moiety so as to form a linkage. The remaining reactive groups of the branching moiety are each reacted with a third reactive group on a linker moiety attached to a saccharide moiety (or capable of being attached to a saccharide moiety).

Optionally, the branching moiety comprise a single reactive group (e.g., amine) capable of linking to the second reactive group (e.g., carboxylate) of a moiety comprising a first and second reactive group, and a plurality of reactive groups (e.g., carboxylates) capable of linking to a third reactive group (e.g., amine) of a linker moiety attached to a saccharide (or capable of being attached to a saccharide moiety). This facilitates the preparation of a branched glycosylating reagent comprising a single reactive group (i.e., the first reactive group described herein) and a plurality of saccharide moieties.

The linker comprises a reactive group that forms a part thereof, also referred to herein as "Z". The linker preferably terminates by the reactive group. A linker is considered terminated by the reactive group when the reactive group is located at the portion of the linker that is farthest from the saccharide moiety.

The reactive group is preferably selected to as to enable its conjugation to biomolecules. Exemplary reactive groups include, but are not limited to, carboxylate (e.g., —$CO_2H$), thiol (—SH), amine (—$NH_2$), halo, azide (—$N_3$), isocyanate (—NCO), isothiocyanate (—N=C=S), hydroxy (—OH), carbonyl (e.g., aldehyde), maleimide, sulfate, phosphate, sulfonyl (e.g. mesyl, tosyl), etc. as well as activated groups, such as N-hydroxy succinimide (NHS) (e.g. NHS esters), sulfo-N-hydroxysuccinimide, anhydride, acyl halide (—C(=O)-halogen) etc.

The reactive groups of the linker may be in a protected form thereof.

As used herein, the phrase "protected form" describes a derivative of a chemical group (e.g., a reactive group) which is less reactive than the chemical group, wherein the derivative can be readily reacted so as to revert to the original chemical group.

A reactive group may be protected by attaching thereto a protecting group. Many adequate protecting groups will be known to one of skill in the art. The latter should be removed prior to conjugation to the target biomolecule. A suitable protecting group is selected such that it can be readily removed without affecting other linkages or functionalities in the molecule (e.g., the conjugate or glycosylation reagent as described herein).

For example, hydroxy groups may be protected in the form of a carboxylate by attaching thereto a carbonyl group (e.g., acetyl), in the form of an ether (e.g., methoxymethyl ether, p-methoxybenzyl ether, methylthiomethyl ether) or by attaching a silyl group (e.g., trialkylsilyl).

Amine groups may be protected, for example, in the form of an amide (e.g., by attaching a carbobenzyloxy group, t-butoxycarbonyl group, or 9-fluorenylmethyloxycarbonyl group).

Carboxylic acid groups, for example, may be protected in the form of esters (e.g., methyl, benzyl, t-butyl esters).

Carbonyl groups, for example, may be protected in the form of acetals (e.g., for protecting aldehydes) or ketals (e.g., for protecting ketones).

Alternatively, the reactive group may be in an activated form thereof.

As used herein, the phrase "activated form" describes a derivative of a chemical group (e.g., a reactive group) which is more reactive than the chemical group, and which is thus readily capable of undergoing a chemical reaction that leads to a bond formation. The activated form may comprise a particularly suitable leaving group, thereby facilitating substitution reactions. For example, a —C(=O)—NHS group (N-hydroxysuccinimide ester, or —C(=O)—O-succinimide) is a well-known activated form of —C(=O)OH, as NHS (N-hydroxysuccinimide) can be reacted with a —C(=O)OH to form —C(=O)—NHS, which readily reacts to form products characteristic of reactions involving —C(=O)OH groups, such as amides and esters.

The reactive group can be attached to the linker via different groups, atoms or bonds. These may include an ether bond [e.g., —O-alkyl-], an ester bond [e.g., —O—C(=O)-alkyl-], a carbamate [e.g., O—C(=O)—NH-alkyl-], etc. Thus, a variety of terminal groups can be employed.

The following are non-limiting examples of the different groups that may constitute the non-saccharide end of the linker chain: Z=—$CH_2CO_2H$, —$CH_2CH_2CO_2H$, —$CH_2CH_2SH$, —$CH_2CH_2NH_2$, —$CH_2CH_2N_3$, —$CH_2CH_2NCO$, —$CH_2$—COO—NHS, —$CH_2CH_2$—COO—NHS, —CO—$CH_2$—COO—NHS, —$CH_2CH_2$—NHCOCH$_2$CH$_2$-maleimide, etc.

The number of methylene groups in each of the above reactive groups is merely exemplary, and may be varied.

The reactive group may also comprise the heteroatom at the end of a poly(alkylene glycol) chain (e.g., —OH).

In exemplary embodiments of the present invention, the reactive group is selected from the group consisting of an amine, a maleimide and a carboxylate, including protected forms and activated forms thereof, as these terms are defined herein. In exemplary embodiments, the carboxylate is a C-carboxy group such as a carboxylic acid, as these terms are defined herein.

As used herein, the terms "amine" and "amino" refer to either a —NR'R" group, wherein R' and R" are selected from the group consisting of hydrogen, alkyl, cycloalkyl, heteroalicyclic (bonded through a ring carbon), aryl and heteroaryl (bonded through a ring carbon). R' and R" are bound via a carbon atom thereof. Optionally, R' and R" are selected from the group consisting of hydrogen and alkyl comprising 1 to 4 carbon atoms. Optionally, R' and R" are hydrogen.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofurane, tetrahydropyrane, morpholino and the like.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

An "ether" refers to both an alkoxy and an aryloxy group, wherein the group is linked to an alkyl, alkenyl, alkymyl, cycloalkyl, aryl, heteroaryl or heteroalicyclic group.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "thioether" refers to both a thioalkoxy and a thioaryloxy group, wherein the group is linked to an alkyl, alkenyl, alkymyl, cycloalkyl, aryl, heteroaryl or heteroalicyclic group.

A "disulfide" group refers to both a —S-thioalkoxy and a —S-thioaryloxy group.

A "carbonyl" group refers to a —C(=O)—R' group, where R' is defined as hereinabove.

An "aldehyde" group refers to a carbonyl group, where R' is hydrogen.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "carboxylate" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An "ester" refers to a C-carboxy group wherein R' is not hydrogen.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

A "urea" group refers to an —N(R)—C(=O)—NR"R'" group, where each of R' and R" is as defined herein, and R'" is defined as R' and R" are defined herein.

A "guanidino" group refers to an —N(R')C(=N—R")—NR'"R"" group, where each of R', R" and R'" is as defined herein, and R"" is defined as R' and R" are defined herein.

A "guanyl" group refers to an R'R"NC(=N—R'")— group, where each of R', R" and R'" is as defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"— group, with each of R' and R" as defined hereinabove.

A "hydrazine" group refers to a —N(R')—NR"R'" group.

An "azo" group refers to a —N=NR' group.

As used herein, the term "maleimide" refers to a cyclic —[NC(=O)—C(R')=C(R")—C(=O)]— moiety, which is linked via the N atom, and wherein R' and R" are as defined hereinabove. The above definitions describe groups as monovalent radicals, i.e., they attach to a single moiety. However, as used herein, many of the groups are intended to encompass groups that attach to a plurality of moieties ("linking groups"), thereby linking the moieties together. Specifically, alkyl, cycloalkyl, aryl and heteroaryl, as defined herein, may attach to more than one moiety. In addition, each group defined above as comprising any of R', R", R'" and R"", may alternatively be defined as a linking group wherein at least one R', R", R' or R"", as these terms are defined herein, is a moiety attached to the linking group, rather than a component of the linking group (e.g., the amine group —NR'R" may be defined as a group linking a first moiety, an R' moiety, and an R" moiety).

In an optional embodiment the glycosylation reagent has the formula depicted in Scheme 1.

Scheme 1

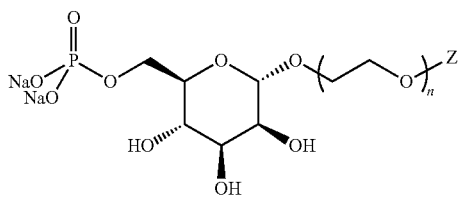

wherein:

n>6; and

Z is selected from the group consisting of —CH$_2$CO$_2$H, —CH$_2$CH$_2$CO$_2$H, —CH$_2$CH$_2$SH, —CH$_2$CH$_2$NH$_2$, —CH$_2$CH$_2$N$_3$, —CH$_2$CH$_2$NCO, —CH$_2$—COO—NHS, —CH$_2$CH$_2$—COO—NHS, —CO—CH$_2$—COO—NHS, and —CH$_2$CH$_2$—NHCOCH$_2$CH$_2$-maleimide (wherein —CH$_2$CH$_2$—NHCOCH$_2$CH$_2$— is bound to the nitrogen atom of maleimide).

Although the above formula depicts the phosphate group as a sodium salt, all formulas herein which describe a phosphate group in any form are to be understood as encompassing the acid form (—P(=O)(OH)$_2$) as well as all salts thereof, including salts comprising one or two cations, and salts including cations other than sodium, unless stated otherwise.

According to an exemplary embodiment of the present invention, n=8 and Z is —CH$_2$CH$_2$CO$_2$H. This compound is also referred to herein as M6P-PEG$_8$-CO$_2$H or M6P-PEG$_8$-COOH.

According to another exemplary embodiment of the present invention, n=8 and Z is —CH$_2$CH$_2$—NHCOCH$_2$CH$_2$-maleimide (see FIG. 1B). This compound is also referred to herein as M6P-PEG$_8$-maleimide Another exemplary glycosylation reagent according to scheme 1, wherein n=12 and Z is —CH$_2$CH$_2$CO$_2$H, is depicted in FIG. 1A. This compound is also referred to herein as M6P-PEG$_{12}$-CO$_2$H or M6P-PEG$_{12}$-COOH.

According to further exemplary embodiments of the present invention, the glycosylating reagent has the formula depicted in FIG. 2A, 2B, 2C, 2D, 3A or 3B.

The reagents of the invention can be synthesized in various ways, employing general synthetic methodologies. Exemplary methods are presented hereinbelow but other techniques, methodologies or reagents can be employed or envisioned by those skilled in the art.

In general, a glycosylation reagent according to the present embodiments can be prepared by treating a saccharide with a HO-A-Z derivative, wherein A and Z are defined as hereinabove. Groups other than the —OH group (e.g., the Z reactive group) can be pre-protected in order to avoid their reaction with the mono-saccharide. In cases where the chemical reactivity of the non-hydroxyl groups (Z) is not expected to lead to an undesired reaction with the saccharide under the reaction conditions of the hydroxyl conjugation to the monosaccharide, prior protection may be unnecessary. In cases where a reactive group is protected, it should be de-protected prior to its use for conjugation to the target biomolecule. If a group other than a reactive group is protected, the group may be de-protected before or after conjugation to the target biomolecule.

The linker can be attached to the saccharide moiety via various synthetic methodologies.

According to one exemplary methodology, penta-acetylated saccharide is mixed with a mono-protected linker (e.g., wherein Z comprises a carboxylic acid protected as an ester) in the presence of boron trifluoride etherate to give an adduct of the linker and the acetylated monosaccharide. Deprotection with aqueous sodium hydroxide gives a glycosylating reagent X-A-Z, wherein Z comprises a carboxylic acid group. This carboxylic acid group can be further used for conjugation to proteins as described below.

Alternatively, as exemplified in Example 1, the penta-acetylated saccharide is reacted with mono-protected linker in the presence of ZnCl$_2$, under elevated temperature conditions (100-110° C.) and vacuum. The product solution is washed with water, the organic solvent is evaporated under reduced pressure and the crude product is purified by crystallization or chromatography of Silica-Gel. The acetyl protecting groups are easily removed by sodium methoxide in methanol.

The use of a penta-acetylated saccharide, as described hereinabove, refers to a saccharide, typically a hexose, having 4 free hydroxyl groups other than the hydroxyl group which is intended to react with the linker (e.g., the free hydroxyl attached to the anomeric carbon). The number of protecting groups (e.g., acetyls) which should be attached to the saccharide according to the procedures described herein will depend on the saccharide being used (e.g., M6P comprises 3 free hydroxyl groups other than the hydroxyl group which is intended to react with the linker).

It is to be noted that in the aforementioned example, acetylation of the hydroxyl attached to the anomeric carbon does not prevent its reaction with the linker.

The carboxylate reactive group of linkers such as in the procedure described above can also be activated by various methods, to enable easy coupling to proteins or other biomolecules. This carboxylic group can be converted to activated carboxamides by the use of N,N,N',N"-tetramethyl(succinimido)uronium tetrafluoroborate (TSTU). This activated carboxamide can be easily used for conjugation to proteins at mild alkaline pH.

A carboxylate reactive group may also be activated by preparing an NHS ester, for example, by activating the corresponding carboxylic acid by using NHS and a carbodiimide agent, such as DCC, optionally catalyzed by a proton scavenger such as dimethylaminopyridine (DMAP). Alternatively, EDC (1-Ethyl-3-[3-dimethylaminopropyl]carbodiimide hydrochloride) is used as the carbodiimide agent. Excess reagents (e.g., DCC, EDC, NHS) and/or byproducts may optionally be separated using an appropriate chromatographic column or through selective crystallization.

As shown in the Examples section that follows, the amount of the activating agents, which form that activated form of the reactive group, utilized can affect the properties of the resulting conjugate (formed upon conjugating the glycosylation reagent to the biomolecule).

The activation of the carboxylate reactive group can optionally be performed prior to the conjugation of the linker to a saccharide moiety. A glycosylating reagent can also be prepared by treating a target saccharide with a HO-A-Z compound under mildly acidic conditions. The hydroxyl group reacts with the anomeric carbon to give a glycosylating reagent. This methodology usually results in a mixture of anomers. These anomers can be further separated by selective crystallization, chromatography or additional common separation techniques.

The glycosylating reagent can also be synthesized by utilizing enzymatic catalysts, preferably immobilized on non-soluble supports, under aqueous, non-aqueous or micro-aqueous conditions. This methodology may employ different commercially available glycosidases as the catalyst.

As discussed hereinabove, the glycosylating reagents described herein are designed suitable for being conjugated to a target biomolecule and are particularly aimed at introducing a saccharide moiety to the biomolecule, for example, so as to beneficially affect its trafficking and uptake by targeted cells, tissues and/or organelles. Herein, a conjugate formed by reacting a biomolecule with a glycosylating reagent having the formula X-A-Z, as defined hereinabove, is described as having a formula X-A-W—B, wherein B is the conjugated biomolecule, W is the chemical group obtained by the reaction of the reactive group Z with the biomolecule, and X and A are defined as for the glycosylating reagent.

Thus, for example, the glycosylating reagent depicted in scheme 1 hereinabove reacts with a biomolecule to form a conjugate having the formula depicted in Scheme 2.

Scheme 2

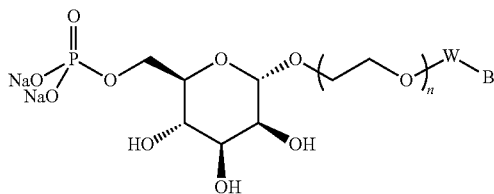

wherein:

n>6;

W is a chemical group obtained by the reaction of the reactive group Z, as defined in Scheme 1, with the biomolecule; and B is the conjugated biomolecule.

The glycosylation reagents of the invention may be used to glycosylate a variety of biomolecules, such as proteins, peptides, oligonucleotides, antisense molecules, polynucleotides, steroids, antibodies, antigens, toxins, growth factors, agonists, antagonists, co-factors, cytokines, enzymes, immunoglobulins, hormones, inhibitors, ligands, prostaglandins, vaccines and vitamins.

The biomolecules can be, for example, derived from eukaryotic (including animal, plant, yeast and fungal), mammalian, human, prokaryotic, bacterial or viral source.

The terms "polypeptide" and "protein", which are used herein interchangeably, refer to a polymeric form of amino acids of 10 or more, and more preferably 100 or more amino acids, which can include coded and non-coded amino acids, chemically or biochemically modified or derivatized amino acids, and polypeptides having modified peptide backbones. Polypeptides may be polymers of naturally occurring amino acid residues; non-naturally occurring amino acid residues, such as, for example N-substituted glycine residues, amino acid substitutes, and the like; and both naturally occurring and non-naturally occurring amino acid residues/substitutes. This term does not refer to or excludes post-translational modifications of the polypeptide, for example, glycosylations, acetylations, phosphorylations and the like. The term includes ribosomally or synthetically made polypeptides, fusion proteins, including, but not limited to, fusion proteins with a heterologous amino acid sequence, fusions with heterologous and homologous leader sequences; immunologically tagged proteins; and the like.

The term "peptide" is defined as is the term "polypeptide" herein, but refers to compounds comprising 2-9 amino acids, rather than compounds having 10 or more amino acids.

As used herein throughout the term "amino acid" or "amino acids" is understood to include the 20 genetically coded or naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids and other non-naturally occurring amino acids.

In some embodiments of the present invention, the biomolecule is a protein, including, for example, hormones, growth factors, enzymes, antibodies, chimeric proteins, structural protein, binding proteins, blood factors and the like. Enzymes are exemplary proteins suitable for inclusion in embodiments of the present invention.

The protein may be a naturally produced protein isolated from a biological source, a synthetically-prepared protein, synthesized (e.g., from amino acids) according methods known in the chemical arts, or a recombinant protein (e.g., produced via genetic engineering). A recombinant protein may be produced, for example, in host cells such as bacterial cells, in fungal cells, in yeast, in whole plants, in plant cells, in mammalian products (e.g., urine, milk) and/or in mammalian cells.

In some embodiments, the protein is recombinantly produced in non-mammalian cells such as, for example, plant cells.

In an exemplary embodiment, the glycosylation reagents of the invention are used to modify lysosomal proteins (e.g. enzymes), such that the biomolecule is a lysosomal protein.

Exemplary lysosomal proteins which may be modified according to embodiments of the present invention include, without limitation, lysosomal protective protein, L-iduronidase, iduronate-2-sulfatase, heparan-N-sulfatase, α-N- acetylglucosaminidase, acetylCoA:α-glucosaminide acetyltransferase, N-acetylglucosamine-6-sulfatase, galactose-6-sulfatase, β-galactosidase, N-acetylgalactosamine-4-sulfatase, β-glucuronidase, hyaluronoglucosaminidase, aspartylglucosaminidase, acid lipase, cystine transporter, Lamp-2, α-galactosidase A, acid ceramidase, α-L-fucosidase, glucocerebrosidase, galactocerebrosidase, α-glucosidase, β-galactosidase, β-hexosaminidase A, β-hexosaminidase B, ganglioside GM2 activator protein, α-D-mannosidase, β-D-mannosidase, arylsulfatase A, saposin B, neuraminidase, phosphotransferase, palmitoyl protein thioesterase, tripeptidyl peptidase I, acid sphingomyelinase, cathepsin K, α-galactosidase B, sialic acid transporter, tartrate-resistant acid phosphatase, asparaginase, ceroid lipofuscinosis neuronal protein 5, CPVL, cathepsin B, dipeptidyl-peptidase I, cathepsin D, cathepsin H, cathepsin L, cathepsin S, cathepsin Z, deoxyribonuclease II, dipeptidyl-peptidase II, N-acetylgalactosamine-6-sulfatase, γ-glutamyl hydrolase, heparanase, legumain, 1-O-acylceramide synthase, myeloperoxidase, α-N-acetylgalactosaminidase, NPC2 protein, plasma glutamate carboxypeptidase, Pro-X carboxypeptidase, proactivator polypeptide, N-sulfoglucosamine sulfohydrolase, sialic acid 9-O-acetylesterase, and tripeptidyl-peptidase I.

Optionally, the lysosomal enzyme is modified by being linked to a M6P moiety. Without being bound by any particular theory, it is believed that the attachment of a M6P moiety facilitates the trafficking of proteins into lysosomes. The trafficking of lysosomal proteins into lysosomes is typically essential for the proper function of lysosomal proteins. Lysosomal enzymes are typically relatively inactive at the pH found outside of the lysosome, and in any case, the activity of a lysosomal enzyme outside a lysosome will in many cases be harmful. Moreover, the proper function of lysosomal proteins is commonly essential for the health of an organism. Thus, for example, deficiencies of many lysosomal proteins result in severe and even lethal diseases or disorders, as discussed in detail hereinbelow.

The conjugation of M6P to a protein is particularly useful for proteins originating from organisms (e.g., microorganisms) or cells (e.g. plants and plant cells) in which there is no M6P glycosylation of proteins.

Embodiments of the present invention may optionally be used to treat a disease or disorder associated with a deficiency of a lysosomal protein in lysosomes. Examples of such diseases and disorders include (deficient protein in parentheses) mucopolysaccharidosis type I (L-iduronase), mucopolysaccharidosis type II (iduronate-2-sulfatase), mucopolysaccharidosis type IIIA (heparan-N-sulfatase), mucopolysaccharidosis type IIIB (α-N-acetylglucosaminidase), mucopolysaccharidosis type IIIC (acetylCoA:α-glucosaminide acetyltransferase), mucopolysaccharidosis type IIID (N-acetylglucosamine-6-sulfatase), mucopolysaccharidosis type IVA (galactose-6-sulfatase), mucopolysaccharidosis type IVB (β-galactosidase), mucopolysaccharidosis type VI (N-acetylgalactosamine-4-sulfatase), mucopolysaccharidosis type VII (β-glucuronidase), mucopolysaccharidosis type IX (hyaluronoglucosaminidase), aspartylglucosaminuria (aspartylglucosaminidase), cholesterol ester storage disease (acid lipase), cystinosis (cystine transporter), Danon disease (Lamp-2), Fabry disease (α-galactosidase A), Farber disease (acid ceramidase), fucosidosis (α-L-fucosidase), galactosialidosis (lysosomal protective protein), Gaucher disease (glucocerebrosidase), globoid cell leucodystrophy (galactocerebrosidase), GM1-gangliosidosis (β-galactosidase), Tay Sachs disease (β-hexosaminidase A), Sandhoff disease (β-hexosaminidase A and B), GM2-gangliosidosis (ganglioside GM2 activator protein), α-mannosidosis (α-D-mannosidase), β-mannosidosis (β-D-mannosidase), metachromatic leucodystrophy (arylsulfatase A, saposin), mucolipidosis type I (neuraminidase), mucolipidosis type II (phosphotransferase), mucolipidosis type IIIC (phosphotransferase), multiple sulfatase deficiency (sulfatases), CLN1 Batten disease (palmitoyl protein thioesterase), CLN2 Batten disease (tripeptidyl peptidase I), Niemann-Pick disease types A and B (acid sphingomyelinase), Niemann-Pick disease type C, pycnodysostosis (cathepsin K), Schindler disease (α-galactosidase B) and sialic acid storage disease (sialic acid transporter).

α-Galactosidase (e.g., α-galactosidase A) and glucocerebrosidase are exemplary lysosomal proteins for use as a biomolecule in conjugates according to embodiments of the present invention. As described herein, α-galactosidase A-containing conjugates may be used for treating Fabry disease, α-galactosidase B-containing conjugates may be used for treating Schindler disease, and glucocerebrosidase-containing conjugates may be used for treating Gaucher's disease.

Alternatively, embodiments of the present invention relate to linking M6P to other (e.g., non-lysosomal) proteins which have been found to be naturally linked to M6P. Exemplary such proteins include, without limitation, lactotransferrin, pancreatic ribonuclease, hornerin, cation-dependent mannose-6-phosphate receptor, ribonuclease K6, intercellular adhesion molecule 1, CREG1 protein, laminin A, hemoglobin ζ chain, cerebellin 4, desmoplakin, fatty acid-binding protein, sulfatase-modifying factor, leukocyte elastase, procollagen-lysine-2-oxoglutarate-5-dioxygenase 1, ferritin light chain, acid sphingomyelinase-like phosphodiesterase 3A, hemoglobin β chain, ribonuclease T2, cat eye syndrome critical region 1, leucine-rich α$_2$-glycoprotein, antithrombin-III, serum amyloid P-component, plasma serine protease inhibitor, haptoglobin-related protein, complement C1q subcomponent A chain, complement C1q subcomponent B chain, complement C1q subcomponent C chain, cholinesterase, angiotensinogen, prostaglandin-H$_2$ D-isomerase, plasma protease C1 inhibitor, mammalian ependymin-related protein, α$_1$B-glycoprotein, plasma kallikrein, hemopexin, AMBP protein, α$_1$-antitrypsin, pigment epithelium-derived factor, α$_2$-macroglobulin, kallistatin, Fc fragment of IgG-binding protein, corticosteroid-binding globulin, zinc-α$_2$-glycoprotein, afamin, serotransferrin, ceruloplasmin, biotimidase, ficolin-3, serum albumin, α$_1$-acid glycoprotein 1, α$_1$-acid glycoprotein 2, CD5 antigen-like, complement C2 precursor, complement C3 precursor, inter-α-trypsin inhibitor heavy chain H4, inter-α-trypsin inhibitor heavy chain 2, inter-α-trypsin inhibitor heavy chain 1, ficolin-2, complement factor B, dopamine β-hydroxylase, fibrinogen β chain, α$_1$-antichymotrypsin, extracellular matrix protein 1, kininogen-1, lumican, complement component 4B, cation-independent mannose-6-phosphate receptor, adipocyte-derived leucine aminopeptidase, fetuin-B, N-acetylmuramoyl-L-alanine amidase, histidine-rich glycoprotein, vitronectin, α$_2$-HS-glycoprotein, clusterin, C4b-binding protein α chain, mannan-binding lectin serine protease 1, and transthyretin (Sleat et al., *Molecular & Cellular Proteomics Methodologies* 5:1942-1956, 2006).

Further alternatively, embodiments of the present invention relate to linking M6P or any other saccharide to any protein which exhibit a therapeutic activity.

These include, in addition to the above-listed proteins, Factor VII, Factor VIII, Factor IX, Protein C (Serine protease), IFN-beta, IFN-alpha DNase, hyaluronidase, fibrolase, plasminogen activator, BMP (bone morphogenetic protein), PDGF (platelete derived growth factor) EPO (Erythropoietin), LH (luteinizing hormone), RHCG (Rh family, C glycoprotein) TNF receptor, IL-1, IL-2, IL-11, urate oxidase, TSH (thyroid stimulating hormone), Glucagon, tPA-(Tissue plasminogen activator), Insulin, Growth Hormone, calcitonin, GM-CSF (granulocyte macrophage colony-stimulating factor), IGF-1 keratinocyte growth factor, TNF-α, Hirudin, Apo2L, Antithrombin III, kallikrein inhibitor, AAT (alpha-1 antitrypsin), lipase, protease, amylase, and VEGF.

As discussed hereinabove, some embodiments of the present invention comprise sialic acid (e.g. N-acetylneuraminic acid) as a saccharide moiety. Follicle-stimulating hormone (FSH) is an exemplary protein for inclusion in conjugates comprising a sialic acid saccharide moiety. Without being bound by any particular theory, it is believed that sialic acid naturally increases the half-life of a glycosylated protein's circulation in serum by masking saccharides from receptors. Thus, it is believed that conjugation of one or more sialic acid moieties to FSH increases the half-life of the FSH in serum, thereby enhancing the efficacy of the FSH. The half-life of biomolecules in serum is highly important from a pharmacological aspect, and increasing the half-life is typically imperative in the development of pharmaceutical biomolecule.

In some embodiments of the present invention, a biomolecule which is suitable for use as a labeling agent is conjugated with the glycosylating agent described herein.

As used herein, the term "labeling agent" refers to a molecule which is readily detected. Exemplary labeling agents include chromophores, fluorophores, chemiluminescent agents, and radiolabeling agents (i.e., radioactive labeling agents). Such a molecule is also referred to herein as being "labeled". Alternatively, a labeling agent may be a molecule that is capable of binding by any of the aforementioned labeling agents. Examples of such molecules include antigens capable of binding to labeled antibodies, antisense molecules capable of binding to labeled oligonucleotides and/or polynucleotides, agonists and antagonists capable of binding to labeled enzymes, ligands capable of binding to labeled receptors and the like. In addition to the aforementioned examples, the antigen, antisense, agonist, antagonist, ligand etc. may be labeled.

The conjugation of a saccharide moiety to a biomolecule that is a labeling agent allows the conjugate to be used for detecting the presence and/or location of particular molecules (e.g., receptors which bind the saccharide), organelles and/or cell types (e.g., organelles or cell types which bind to and/or accumulate the saccharide). For example, a conjugate comprising a biomolecule labeling agent and M6P may be used to detect and/or visualize lysosomes, in which M6P-containing biomolecules typically accumulate, or receptors which bind M6P moieties.

In an exemplary embodiment, the biomolecule is green fluorescent protein (GFP), which is a well-known fluorophore. As exemplified in the Examples section herein, GFP conjugated to M6P enters cells, allowing visualization by fluorescent microscope.

The conjugates described herein may be used, for example, to deliver biomolecules to specific targets bearing a receptor which binds the saccharide moiety of the conjugate. Thus, a polynucleotide or oligonucleotide biomolecule that is complementary to mRNA may be delivered to a particular target in order to inhibit expression of a specific protein via RNA interference, a biomolecule which inhibits a specific enzyme may be targeted to a cell or organelle (e.g., a lysosome) where the enzyme is located, and a biomolecule which is toxic may be delivered to cancer cells.

The conjugation of the glycosylation reagent and the biomolecule is preferably effected by reacting the glycosylation reagent described herein, in which the linker comprises reactive group, with the biomolecule.

The reactive groups of the linker may be conjugated, for example, to different accessible functional groups of the biomolecule.

The phrase "accessible functional group", as used herein, refers to a functional group in the surface area of the polypeptide that is accessible to the molecules of the solvent it is dissolved in. The solvent-accessible surface is often referred to as the Lee-Richards molecular surface [Lee B. and Richards FM., 1971, "The interpretation of protein structures: estimation of static accessibility", *J. Mol. Biol.*, 55 (3), pp. 379-400]. A functional group of an amino-acid residue which is positioned at or near the solvent-accessible surface of a protein is more likely to be available for chemical modifications and polymer conjugation, such as PEGylation.

As used herein, the phrase "functional group" describes a chemical group which exhibits a characteristic chemical property, and includes, for example, the alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino chemical groups defined herein. Exemplary functional groups commonly found on biomolecules include, without limitation, alkyl, aryl, heteroaryl, hydroxy, thiol, amine, carboxylate, amide, guanidino, thioalkoxy, phosphate and sulfate.

Thus, for example, the reactive groups of the linker can be conjugated to functional groups of accessible amino acids on the protein to be modified, preferably carboxylate (e.g., in glutamate and aspartate residues), thiol (e.g., in cysteine residues), amine (e.g., in lysine residues) or hydroxy (e.g., in serine or threonine residues) groups. In addition, the linker can be conjugated to functional groups, typically hydroxy, of accessible saccharide units of a glycoside (e.g., a glycoprotein).

A functional group may optionally be introduced to a biomolecule by modification of the biomolecule. For example, thiol groups may be introduced (i.e., "thiolation") to the side chains of residues (e.g., lysine residues) in proteins according to methods known in the art. Aldehyde group may be introduced by oxidizing a hydroxy group, preferably a saccharide-derived hydroxy group as described hereinabove.

As discussed hereinabove, the reactive groups of the linker may be optionally conjugated to a wide variety of functional groups on a protein. Hence, the conjugation described herein is not limited to natural glycosylation sites on proteins, such as specific asparagine residues (i.e., in N-linked glycosylation) or serine or threonine residues (i.e., in O-linked glycosylation), and is therefore more versatile.

Conjugation of the reactive group of the linker to a functional group of the biomolecule results in the formation of a covalent bond between the reactive group and the functional group.

In an optional embodiment, the reactive group is a carboxylate, as described herein, and the functional group is an amine. Alternatively, the reactive group is an amine and the functional group is a carboxylate. Typically, conjugation of such groups forms an amide. Preferably, the amine is not a tertiary amine (i.e., preferably at least one of R' and R" is hydrogen). More preferably, the amine is a primary amine (i.e., R' and R" are both hydrogen).

In an alternative embodiment, the reactive group is maleimide and the functional group is a thiol. Typically, conjugation of such groups involves addition of the thiol to the C═C bond in the maleimide, forming a succinimide group covalently bound to the sulfur atom of the thiol.

In another example, a reactive group (e.g., carboxy) activated with an NHS group is easily coupled to primary amine groups of a biomolecule, such as a lysine residue on a protein. This coupling is preferably carried out at slightly alkaline pH levels, ensuring that the amines are not protonated and can act as good nucleophiles. Alternatively, the reactive group comprises a carboxylate (e.g., carboxylic acid) group and can be conjugated to a protein's primary amines via the well established carbodiimide coupling chemistry. Similarly, reactive groups comprising an amine group can be coupled to free carboxylic groups on the protein, as in aspartic or glutamic acids, via the same carbodiimide chemistry. Linker chains comprising a maleimide group can be used for coupling the linker chain to free thiol groups, such as in cysteines. In general, various bio-conjugation methods can be used to conjugate the reagents of the invention to biomolecules.

A biomolecule may be modified with one or more molecules of the glycosylating reagent. Thus, the biomolecule may bound, for example, to 1, 2, 3, 4, 5, 6, 7, 8, 9, 10, 11, 12, 13, 14, 15, 16, 17, 18, 19, 20 and even more (e.g., 100) molecules of the glycosylating reagent (on average).

The proportion of glycosylation reagents per biomolecules can be controlled by the conjugation chemistry used. Thus, the identity and number of possible amino acids for conjugation may limit the total number of glycosylation reagents that can be attached to each protein, even when an excess of the glycosylation reagent is used.

Thus, the proportion will depend, for example, on the ratio of glycosylating reagent to biomolecule in the reaction mixture, on the number of accessible functional groups capable of being bound by the reactive group of the glycosylating agent, and in cases where the reactive group is activated, on the ratio of glycosylating reagent and an activator thereof (e.g., a carbodiimide reagent and/or NHS). The proportion can be determined and controlled by a person skilled in the art through routine experimentation.

A biomolecule may be modified with a combination of different glycosylation reagents to enable binding or interaction with multiple receptors or to increase the probability of binding to a receptor.

In some cases a target amino acid to be coupled to the glycosylating reagent is found in the active site of the protein. In such cases, conjugation to the active site amino acid would lead to loss of activity of the protein. For example, a common conjugation methodology to proteins includes targeting the primary amines of lysine residues on the surface of proteins. Human α-galactosidase-A has 16 lysine residues in its sequence and most of these are accessible to the solvent. However, Lys 168 seems to be located in the active-site itself and even participate in the recognition and catalytic machinery. In such cases, conjugation of the desired glycosylation reagent can optionally take place in the presence of an appropriate reversible inhibitor of the specific enzyme to be modified. Optionally, the inhibitor is found in excess and the active site of the enzyme is predominantly occupied by the inhibitor and the active site amino acids are sterically protected from conjugation reagents. The inhibitor is easily evacuated during dialysis, ultra-filtration or chromatographic steps required to remove excess conjugation reagents and side-products.

In the case of human α-galactosidase-A, conjugation of an M6Pylation reagent to surface lysines may take place in the presence of inhibitors such as 1-deoxynojirimycin.

Following the conjugation, the obtained conjugate (e.g., glycosylated protein) can be further purified. Purification is advantageous for removing excess glycosylation reagents, as well as other reagents used in the conjugation protocol or side products formed. Purification steps can also purify or separate modified biomolecules in which the modification profiles are significantly different, for example, proteins which were significantly insufficiently modified or alternatively over modified.

Purification steps employed for the purification of, for example, the modified (conjugated) proteins of the invention include common protein purification steps known in the art. These may include dialysis or ultra-filtration procedures, which are especially efficient in removing low molecular weight species, such as excess glycosylation reagents, other coupling reagents or catalysts, as well as organic co-solvents used in the glycosylation step. Dialysis using membranes with a cut-off of about 10,000 are the most efficient at this stage. Other purification techniques, such as ammonium sulfate precipitation or acetone precipitation may be employed to separate the modified proteins from one or more contaminant or ingredient described above.

In case further purification steps are required, the partially purified conjugated proteins can be further purified by a variety of chromatography techniques. These may include size-exclusion or gel filtration chromatography, as well as a variety of ion exchange and hydrophobic chromatographic separation steps. Hydrophobic chromatography enables the differentiation between proteins with different levels of modifications.

The modified proteins (conjugates) of the invention carry unique predetermined monosaccharides, according to the glycosylation reagent used. These terminal monosaccharides are useful in affinity chromatography using lectins or lectin-like species, specific for the monosaccharide that is conjugated to the protein. Such affinity chromatography methodology is extremely useful in the separation of non-conjugated proteins and conjugated proteins and by differentiating between conjugated proteins according to the level of their derivatization.

The glycosylation of proteins with the reagents described herein typically changes some of their biochemical properties. Thus, the modified proteins are optionally analyzed for changes in their biochemical properties. Purity and molecular weight of the modified protein may be analyzed by SDS or non-denatured PAGE, followed by staining with an appropriate visualization dye, such as coomassie blue or silver stain, or using Western blotting. The molecular weight of the modified proteins is more accurately analyzed by mass spectrometry methods (MALDI-TOF or ESI). Changes to the isoelectric point (pI) of the modified proteins may be ascertained by using isoelectric focusing (IEF). All these methods, as well as other common biochemical protein analyses, are well known in the art and some are described in the Examples section that follows. Other common methods can also be applied.

As used herein, the phrase "biochemical properties" refers to the basic chemical properties of a molecule in an environment (e.g., an aqueous solution at a temperature of 25° C. or 37° C.) characteristic of a biological system. Exemplary biochemical properties include molecular weight, molecular structure, acidity and electrostatic charge.

In one embodiment, when a biomolecule has a biological activity (e.g., enzymatic activity), the biological activity of the biomolecule is unaffected by its conjugation.

In other embodiments, as detailed hereinbelow, the biological activity of the biomolecule is modified (e.g., enhanced or reduced) upon its conjugation.

As used herein, the phrase "biological activity" refers to an interaction with one or more biomolecules and/or other molecules and/or ions present in a biological system (e.g., in a cell or in an organism), wherein the interaction produces a biologically significant effect. Examples of biological activities include, without limitation, specific binding, catalytic activity, cell signaling, immunogenic properties and cell uptake.

Thus, for example, a catalytic activity of an enzyme conjugated to a saccharide may optionally be the same or greater than its catalytic activity when non-conjugated.

A catalytic activity may optionally be increased by increasing the catalytic coefficient ($k_{cat}$) of an enzyme, indicating more efficient conversion of a substrate bound to an enzyme, or optionally by enhancing the binding of a substrate to the enzyme (e.g., reducing the Michaelis-Menten constant $K_m$).

Optionally, the glycosylating reagent is selected for conjugation to a particular enzyme such that the saccharide moiety and/or linker bound to the enzyme increase the catalytic activity thereof. Optimal glycosylation reagents may be selected following routine experimentation with various glycosylation reagents described herein.

Natural glycosylation as well as protein modifications have been known to affect the tertiary structure of proteins, hence influencing the affinity between the protein and its receptor or substrates in the case of enzymes. Thus, the glycosylation may enable higher affinity towards the transition state of the catalyzed reaction, reducing in turn the energetic barrier of the catalyzed reaction. Alternatively, glycosylations, and other protein modifications, may create a micro-environment for the protein, enabling better interaction with a ligand or substrate or stabilizing the protein in a specific environment (e.g. enhancing its solubility).

In cases where the modified biomolecule is an enzyme, the latter is optionally analyzed to ensure that the conjugation has not caused partial or full inactivation of their enzymatic machinery. Activity analysis can be used to fine-tune the modification protocol, level of modification, and specific sites of modification.

The Michaelis-Menten kinetic parameters of the modified enzymes may be analyzed according to known protocols ("*Structure and Mechanism in Protein Science*", Alan Fersht, W.H. Freeman and Company, 1999).

For example, the activity of the exemplary enzyme α-galactosidase A is commonly analyzed by following the enzyme-catalyzed hydrolysis of model galactopyranoside substrates in an appropriate activity buffer, preferably in a buffer of relatively low pH, mimicking the pH conditions in lysosomes, such as 4.6 (Kulkarni et al., *Biotechnol. Appl. Biochem.* 2006, 45, 51; Dean et al. *The Journal of Biological Chemistry*, 1979, 254 (20), 9994). These substrates include p-nitrophenyl-α-D-galacto-pyranoside and 4-methylumbelliferyl-α-D-galactopyranoside. The hydrolysis reactions are carried out at 37° C. and are terminated by quenching with an appropriate alkaline solution, yielding the desired chromophore of p-nitrophenol or fluorophore of 4-methylumbelliferol. The level of hydrolyzed substrates is quantified spectrophotometrically.

The binding affinity of the biomolecule in the conjugate to a target (e.g., a receptor for the biomolecule) may optionally be substantially identical to that of the unmodified biomolecule.

Alternatively, the binding affinity of the conjugate may be greater than the binding affinity of the unmodified biomolecule.

A biomolecule may be capable of binding to a plurality of targets, in which case it may be characterized by a plurality of binding affinities. The binding affinities of the biomolecule to each of the targets may independently be increased, decreased or unaffected by the conjugation of the biomolecule.

In an optional embodiment, the binding of the biomolecule (e.g., a hormone) effects a cell signaling process.

A conjugate may optionally have an increased binding affinity to a receptor, such that a biological activity of the conjugate is greater than a corresponding biological activity in an unmodified biomolecule.

Alternatively or additionally, a conjugate may optionally have a decreased binding to a molecule which eliminates the biomolecule (e.g., by metabolism and/or inactivation), such that the conjugate has a longer lasting biological activity than an unmodified biomolecule.

The binding affinities of a conjugate and the corresponding biomolecule to a target may be determined according to standard protocols.

For example, a solution containing a predetermined concentration of the biomolecule (conjugated or unmodified) may be contacted with an immobilized target, such as a target covalently bound to a solid surface (e.g. a bead). The immobilized target is then rinsed, and the quantity of remaining biomolecule is determined by any method known in the art. Repetition of the experiment using different concentrations of the biomolecule allows the determination of a binding affinity constant, as is well-known in the art. Alternatively, the biomolecule may be immobilized and contacted with a solution containing the target.

Carbohydrates on the surface of proteins are known to elicit immunogenic responses. Different methodologies have been devised following pharmaceutical studies to minimize such response. One of these methodologies involves the masking of surface carbohydrates by using high molecular weight PEG chains. As discussed hereinabove, PEG and similar molecular chains may be used as a linker in embodiments of the present invention. Thus, the linkers in the conjugates of the present embodiments are optionally selected so as to diminish immunogenicity of glycosides on the surface of the protein.

The immunogenicity of the modified proteins is optionally analyzed by standard protocols. In general, a formulation of a modified protein is injected to mice and the response of their immune system is evaluated by the total level of immunoglobulins as well as the generation of specific antibodies. The immunogenic response is compared to the response of the unmodified proteins.

The modified proteins bind to receptors with natural affinity towards the saccharide used in the modification. This binding may lead to internalization of the modified protein into target cells, and even into specific organelles, such as lysosomes.

Uptake of a modified protein can be ascertained by contacting the modified protein with target cells or organelles in vitro and/or in vivo, and measuring an amount of the protein in the target cells or organelles. The amount of a protein may be measured by any suitable method used in the art.

In embodiments wherein a biological activity of the biomolecule involves uptake by a particular cell type (e.g., cells characterized by a lack of activity of the biomolecule), the conjugate described herein is optionally characterized by higher affinity to the cells than the biomolecule per se.

Optionally, the affinity of the modified and non-modified biomolecules to the cell type is determined by incubating the biomolecule with a culture of the cell type for a period of 1 to 24 hours (e.g., 5 hours), replacing the cell medium, collecting and lysing the cells, and assaying the obtained cell extract for the presence of the biomolecule according to a standard assay for the biomolecule.

In exemplary embodiments, uptake of a conjugated biomolecule is at least 10% higher than uptake of a corresponding non-modified biomolecule. Optionally, the uptake is increased by at least 15%, optionally by at least 50%, optionally by at least 75%, optionally by at least 100%, optionally by at least 150%, optionally by at least 200%, and optionally by at least 300%.

For example, proteins may be detected using immunological methods, such as Western blotting and/or immunohistochemistry, by using an antibody against the protein. Such antibodies may be obtained commercially, or by inducing an immune response in an animal against the protein. Antibodies may be labeled (e.g., with a chromophore, fluorophore and/or radiolabel) using techniques known in the art, for use in methods (e.g., immunohistochemistry) in which labeled antibodies are preferred.

In an exemplary embodiment, the uptake of an α-galactosidase-A modified with M6P-PEG$_8$-COOH (M6P(α1)-O—(CH$_2$CH$_2$O)$_8$—CH$_2$CH$_2$COOH) by fibroblasts of a Fabry patient is evaluated. Fabry fibroblasts are pre-cultured in an appropriate medium and incubated with the modified α-galactosidase-A. Following incubation, the cells are washed, centrifuged, lysed and the level of up-taken enzyme is analyzed using the p-nitrophenyl-α-D-galactopyranoside activity assay (see the Examples section below).

In exemplary embodiments, the conjugate comprises M6P-PEG$_8$-COOH, M6P-PEG$_8$-maleimide or M6P-PEG$_{12}$-COOH as described hereinabove, conjugated to a biomolecule. Optionally the biomolecule is an α-galactosidase (e.g., α-galactosidase A), a glucocerebrosidase or GFP.

The above conjugates can be prepared, for example, by conjugating the abovementioned proteins to M6P-PEG$_8$-COO—NHS (M6P(α1)-O—(CH$_2$CH$_2$O)$_7$—CH$_2$CH$_2$COO—NHS.

In another exemplary embodiment, the conjugate has the formula:

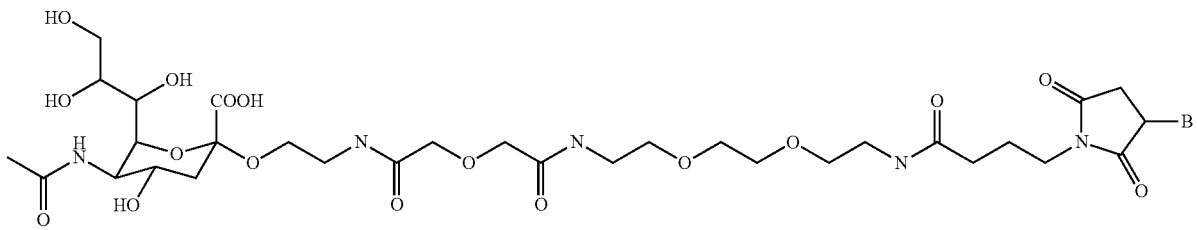

Alternatively, the uptake of an enzyme may be quantified by measuring the rate of a reaction catalyzed by the enzyme. Optionally, the reaction produces or consumes a compound which is readily detected (e.g., a chromophore or fluorophore).

For in vivo testing, the uptake into different tissue types can be compared by collecting the different tissue types and measuring the uptake in each tissue.

For in vitro testing, the uptake into different cell types may be compared by comparing results obtained using cell cultures of different cell types.

wherein B is the biomolecule. This conjugate may be prepared by conjugating the biomolecule with the glycosylating reagent shown in FIG. 3A.

As can be seen in the above formula, a maleimide group in a glycosylating reagent typically does not retain the structure of maleimide in the conjugate. Rather, the maleimide group reacts so as to produce a succinimide moiety bound to the biomolecule, typically to sulfur atom of a thiol in the biomolecule. However, the succinimide group in a conjugate may be referred to herein as a "maleimide", in order to make clear which glycosylating reagent produces the conjugate.

In another exemplary embodiment, the conjugate has the formula:

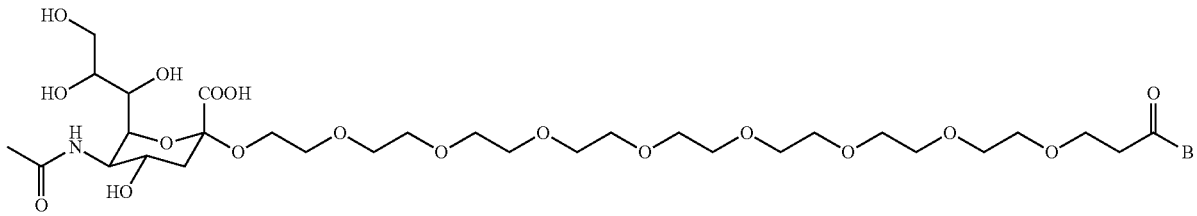

The enhanced uptake of a modified protein can be ascertained by comparing uptake of modified and non-modified proteins.

wherein B is the biomolecule. This conjugate may be prepared by conjugating the biomolecule with the glycosylating reagent shown in FIG. 3B.

In another exemplary embodiment, the conjugate has the formula:

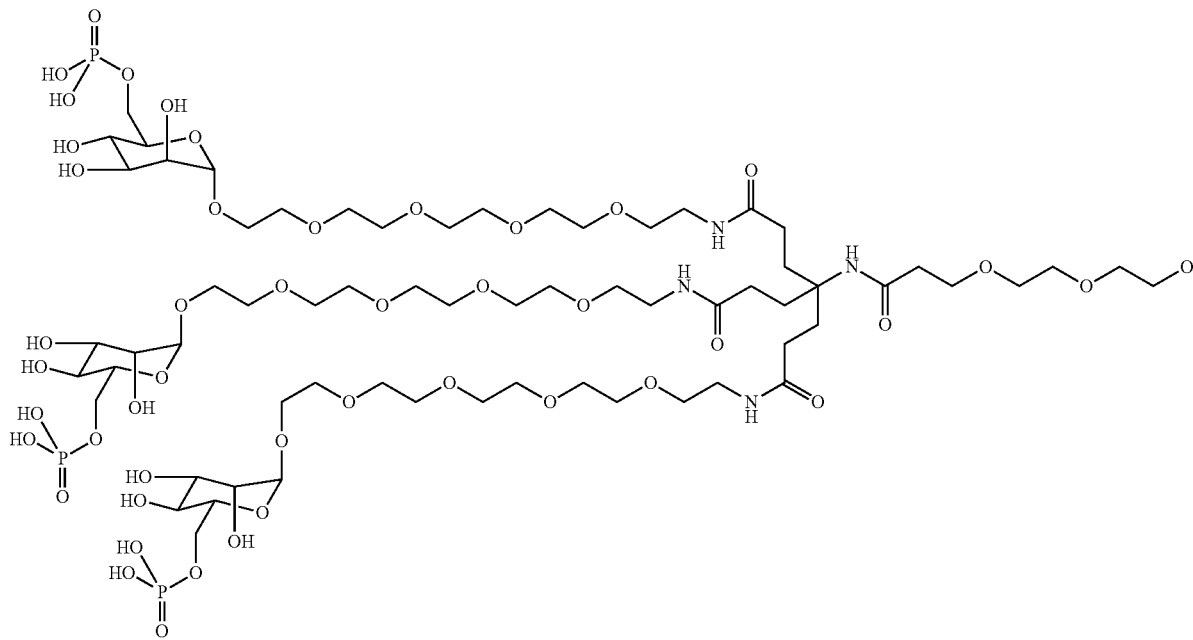

wherein B is the biomolecule. This conjugate may be prepared by conjugating the biomolecule with the glycosylating reagent shown in FIG. 2A.

In another exemplary embodiment, the conjugate has the formula:

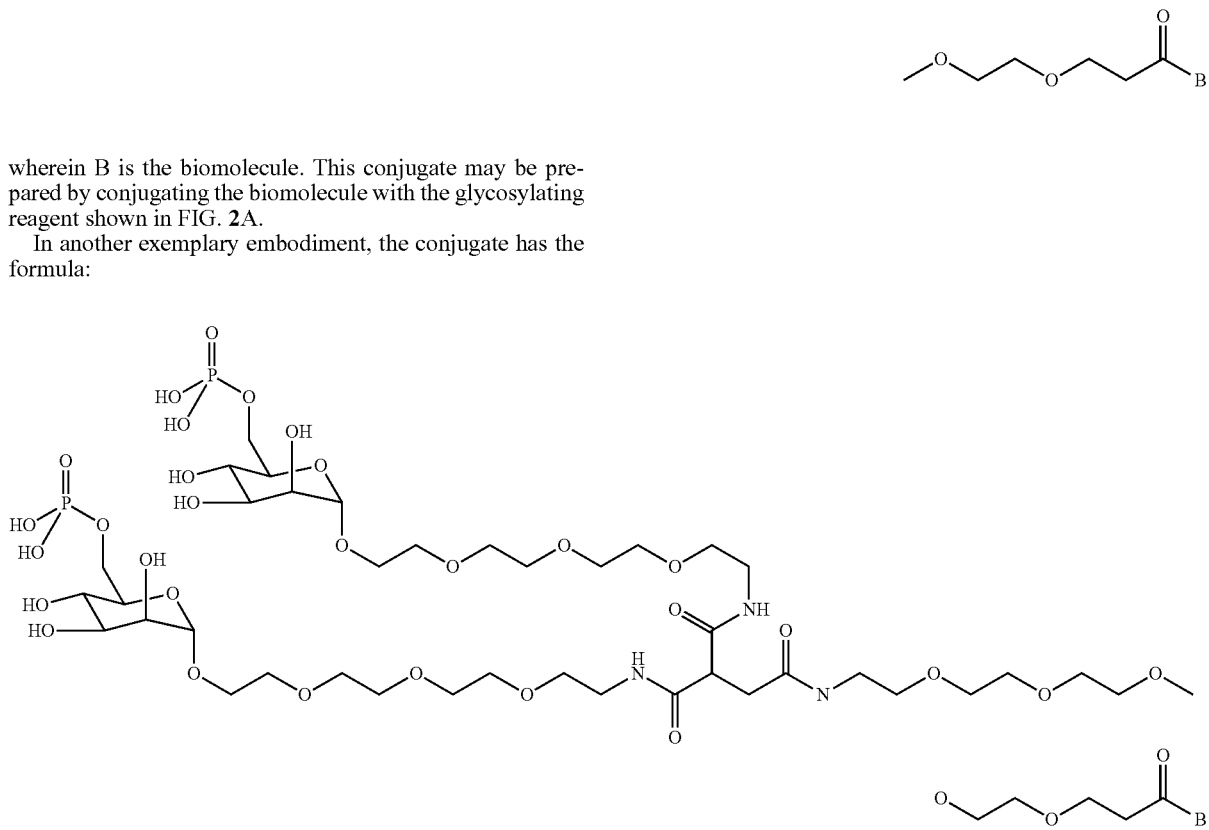

wherein B is the biomolecule. This conjugate may be prepared by conjugating the biomolecule with the glycosylating reagent shown in FIG. 2B.

In another exemplary embodiment, the conjugate has the formula:
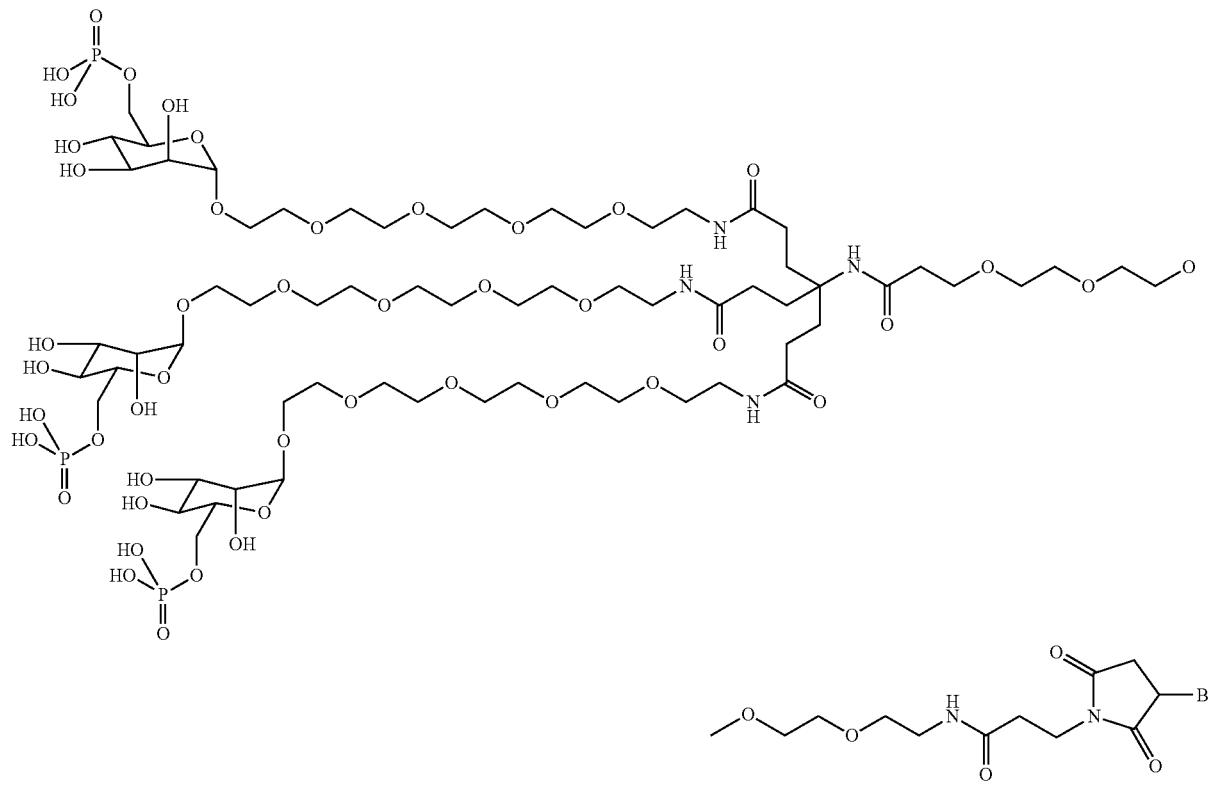
wherein B is the biomolecule. This conjugate may be prepared by conjugating the biomolecule with the glycosylating reagent shown in FIG. 2C.
In another exemplary embodiment, the conjugate has the formula:
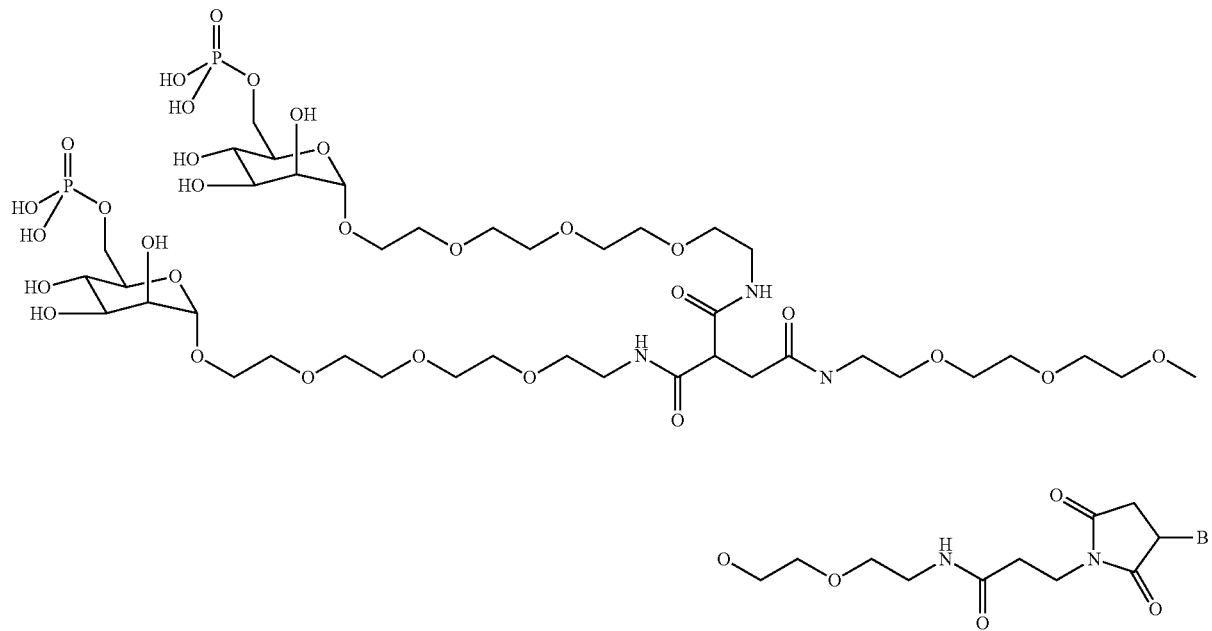

wherein B is the biomolecule. This conjugate may be prepared by conjugating the biomolecule with the glycosylating reagent shown in FIG. 2D.

The glycosphingolipid ceramide trihexoside (Gb3) accumulates in Fabry disease due to improper or lack of activity of endogenous α-galactosidase-A. Thus, the levels of Gb3 and its hydrolytic product, lactosylceramide, are optionally evaluated in the Fabry fibroblasts, following their incubation with the M6P-modified α-galactosidase-A. Reduced levels of Gb3 and elevated levels of lactosylceramide are an excellent indication not just to the mere uptake of the M6P-modified α-galactosidase-A but to its catalytic activity within the cells. Washed and lysed Fabry fibroblasts that are incubated with M6P-modified α-galactosidase-A are extracted with chloroform:methanol (2:1) and following further RP-18 chromatography, the lipids are analyzed using thin layer chromatography against Gb3 and lactosylceramide standards. The latter are also used to create a calibration curve which is used to quantify the levels of Gb3 and lactosylceramide following treatment with the M6P-modified α-galactosidase-A.

The modification with the glycosylation reagents of the invention leads to uptake of the exogenous proteins and enables exerting their therapeutic/biological activity at the target cells by enabling their binding to the target receptor. The modification with the glycosylation reagents of the invention can also lead to stabilization of the protein and enhancement of its half-life in serum and control of its immunogenicity. Enhancement of half-life in serum is of extreme therapeutic importance in case the protein is required to react with receptors and/or be absorbed into target cells in order to exert its activity. Enhancement of half-life in serum is also important for biomolecules which exert an activity in the serum, for example, degrading a specific toxic material. As described hereinabove, the half-life in serum of a protein is optionally increased by modifying the protein with a sialic acid moiety.

The modification of biomolecules with the glycosylation reagents presented herein therefore leads to a change in the interaction profile of the biomolecule as a function of the saccharide moiety utilized. The saccharides which are added to the biomolecule via the glycosylation reagent can result, for example, in interaction (binding) of the biomolecules with new saccharide binding receptors, in interaction of the biomolecule with multiple receptors and/or multiple binding sites, in an improved interaction of the biomolecule with saccharide binding receptors (in terms of e.g., higher affinity and/or increased number of interaction sites), in reduced immunogenity, and/or in increased affinity to target organs, tissues or cells such as macrophages, liver cells, spleen cells, kidney cells, epithelial cells, etc.

The conjugates described herein are therefore characterized by features that render these conjugates highly beneficial for use in various medical applications, including therapeutic and research applications.

For example, the conjugate may localize the biomolecule therein to a particular cell type, organelle or receptor, as discussed hereinabove regarding M6P moieties, and/or the conjugate may enhance the activity of a biomolecule, as discussed hereinabove regarding sialic acid moieties.

Thus, according to the present embodiments, there is provided a pharmaceutical composition that comprises a conjugate as described herein and a pharmaceutically acceptable carrier.

As used herein a "pharmaceutical composition" refers to a preparation of one or more of the conjugates described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the conjugates into preparations which can be used pharmaceutically. Proper formulation is dependent upon the route of administration chosen.

For injection, the conjugates of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the conjugates of the invention can be formulated readily by combining the conjugates with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active conjugate doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the conjugates may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the conjugates for use according to the present invention are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the conjugates and a suitable powder base such as, but not limited to, lactose or starch.

The conjugates described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the conjugate preparation in water-soluble form. Additionally, suspensions of the conjugates may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the conjugates to allow for the preparation of highly concentrated solutions.

Alternatively, the conjugates may be in powder form for constitution with a suitable vehicle, e.g., sterile, pyrogen-free water, before use.

The conjugates of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in the context of the present invention include compositions wherein the active ingredients are contained in an amount effective to achieve the intended purpose. More specifically, a therapeutically effective amount means an amount of conjugates effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any conjugates used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test conjugates, which achieves a half-maximal increase in a biological activity of the conjugate). Such information can be used to more accurately determine useful doses in humans.

As is demonstrated in the Examples section that follows, a therapeutically effective amount for the conjugates of the present invention may range between about 1 µg/kg body weight and about 500 mg/kg body weight.

Toxicity and therapeutic efficacy of the conjugates described herein can be determined by standard pharmaceutical procedures in experimental animals, e.g., by determining the $EC_{50}$, the $IC_{50}$ and the $LD_{50}$ (lethal dose causing death in 50% of the tested animals) for a subject conjugate. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve the desired level of activity in vitro. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a conjugate of the invention formulated in a compatible pharmaceutical carrier may also be prepared, placed in an appropriate container, and labeled for treatment of an indicated condition or diagnosis, as is detailed herein.

Thus, according to an embodiment of the present invention, depending on the selected conjugates, the pharmaceutical composition described herein is packaged in a packaging material and identified in print, in or on the packaging material, for use in the treatment of a condition in which the activity of the conjugate is beneficial, as described hereinabove.

Further, there is provided a use of the conjugates described herein in the manufacture of a medicament. The medicament can be for treating a variety of diseases and disorders, depending on the biomolecule utilized and the nature of the glycosylation reagent. In exemplary embodiments, the medicament can be used in enzyme replacement therapy (ERT), hormone replacement therapy, as vaccines, and the like.

As used herein, the phrase "enzyme replacement therapy" describes a therapy wherein an enzyme is administered to a patient in whom that enzyme is deficient or absent. An enzyme may be deficient in quantity (e.g., expressed at lower than normal levels) and/or in activity (e.g., the activity of the enzyme is reduced or eliminated due to a mutation).

As used herein, the phrase "hormone replacement therapy" describes a therapy wherein a hormone or an analog of a hormone is administered to a patient in whom that hormone is deficient or absent.

As used herein, a hormone or enzyme is termed "deficient" if there is a disease, disorder or discomfort associated with the level of the hormone or enzyme, and the disease, disorder or discomfort is expected to be ameliorated, alleviated or prevented by a higher level of the hormone or enzyme in the patient.

The disease or disorder which the medicament is used to treat may be, for example, a metabolic disease or disorder.

As used herein, the phrase "metabolic disease or disorder" describes a disease or disorder associated with an abnormal form of metabolism. Such conditions (e.g., lysosomal storage diseases) are often a result of a deficiency or absence of an enzyme, and are thus treated with enzyme replacement therapy.

As used herein and in the art, the phrase "lysosomal storage disease" describes a disease associated with a defective function of lysosomes due to a deficiency or absence of an enzyme, which results in a deleterious accumulation of one or more materials in the lysosomes.

In general, in cases where the biomolecule is a protein, the conjugates of the present invention may be used to treat a protein-related disease or disorder.

As used herein, the term "protein-related disease" describes a disease associated with an abnormal function of one or more proteins (e.g., enzymes, hormones, cytokines, receptors etc.). The abnormal function may be, for example, a deficiency of one or more protein.

A protein-related disease may be treated, for example, by administering a conjugate comprising a protein that is deficient in the patient. Alternatively, the conjugate comprises a protein that counteracts an undesirable activity of another protein in the patient, or enhances an activity of another protein which is weaker than desired in the patient.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Materials and Methods

Proteins:

α-Galactosidase A and glucocerebrosidase were recombinantly produced from plant cells as described in International Patent Application PCT/IL2008/000576 and Shaaltiel et al., *Plant Biotechnology Journal* (2007) 5: 579-590.

Green fluorescent protein (Recombinant EGFP Protein, cat# 4999-1000) was purchased from BioVision Research Products (Mountain View, Calif.).

SDS-Page Western Blotting:

SDS-PAGE was effected under standard conditions using 12% SDS-PAGE. Electrophoresis was effected with a Criterion™ cell vertical electrophoresis apparatus (Bio-Rad Laboratories) with premixed electrophoresis Tris-Glycine-SDS running buffer (Bio-Rad Laboratories). 12% acrylamide gels were prepared using premixed solutions of 40% acrylamide/Bis and 10% SDS solution. Transfer of proteins from bis-acrylamide gels to nitrocellulose membrane was effected using a BIO-RAD Criterion™ blotter system overnight at room temperature in 30 V. The membrane was then blocked with PBS containing 5% non-fat dry milk, washed with PBS containing 0.1% Tween-20, and bound to the primary and secondary antibody using PBS containing 0.1% Tween-20. The primary antibody used was Rb-anti-α-GalA (1:1500; H-104 sc-25823, Santa Cruz) or 1:5000 anti-GCD (prepared as described herein). Detection was preformed with an ECL detection kit (Pierce). Bands were detected using the Molecular Imager Gel Doc XR System (Bio-Rad Laboratories) for 30", 60", 90" as needed.

Mass Spectrometry:

Mass-Spectrometry (MS) analysis was performed using a matrix-assisted laser desorption ionization time-of-flight/time-of-flight (MALDI-TOF) mass spectrometer (4700, Applied Biosystems, Foster City Calif.) and an ion-trap mass spectrometer (LCQ classic, Finnigan, San Jose, Calif.).

α-Galactosidase-A-Deficient Mice:

Jackson B6J129Gla α-galactosidase-A-deficient mice ("Fabry mice") were purchased from Jackson Laboratories. These mice are characterized by being totally deficient in α-Galactosidase-A activity and progressively accumulate Gb3 in both plasma and in the lysosomes of most tissues (in particular, the liver, spleen, heart, skin, and kidneys). In addition, these mice have no clinical disease phenotype and survive a normal laboratory life span (>2 years). Hemizygous affected males were bred to homozygous affected females, thereby providing only affected offspring. For these studies, all mice were affected adult males 12 to 30 weeks of age at study initiation.

Fabry Fibroblast Cultures:

Human Fabry (α-galactosidase-deficient) fibroblasts originating from Fabry patients (Cat. ID GMO2775, Cornell Institute) were used. The fibroblasts were cultured in 24-well culture plates containing DMEM (Dulbecco's modified Eagle medium) (cat. D5546, Sigma) supplemented with 12% FBS (fetal bovine serum), 5 ml L-glutamine, 5 ml MEM Eagle vitamin solution, 10 ml MEM amino acid solution, 5 ml MEM Eagle non-essential amino acid solution and 5 ml Pen-Strep solution, all supplements from Biological Industries (Beit Haemek, Ill.).

α-Galactosidase-A Assay:

The level of active α-galactosidase A was determined against a calibration curve of the activity of a commercial α-galactosidase (Fabrazyme®, Genzyme, Cambridge, Mass.) plotted for the concentration range of 200-12.5 ng/ml. Activity was determined using p-nitrophenyl-α-D-galactopyranoside (Sigma) as a hydrolysis substrate. The assay buffer contained 20 mM citric acid, 30 mM sodium phosphate, 0.1% BSA and 0.67% ethanol at pH 4.6. The assay was performed in 96 well ELISA plates (Greiner # 655061). 50 μA of tissue sample lysates were incubated with 150 μl assay buffer and 30 μl substrate was added to obtain a final concentration of 8 mM. The reaction mixture was incubated at 37° C. for 90 minutes and results were plotted against the calibration results. Product (p-nitrophenyl; pNP) formation was detected by absorbance at 405 nm. Absorbance at 405 nm was measured before initiating the reaction. After 90 minutes, 100 μl of 1.98 M sodium carbonate was added to each well in order to terminate the reaction, and absorbance at 405 nm was measured again.

Anti-GCD Antibodies:

75 μg of recombinant GCD (Cerezyme™) was suspended in 3 ml complete Freund's adjuvant and injected to each of two rabbits. Each rabbit was given a booster injection after two weeks. The rabbits were bled approximately 10 days after the booster injection and again at one week intervals until the antibody titer began to drop. Following removal of the clot the serum was divided into aliquots and stored at −20° C.

Example 1

Synthesis of Mannose (α1)-O—CH$_2$CH$_2$—(OCH$_2$CH$_2$)$_7$—O—CH$_2$CH$_2$COO—NHS As mentioned above, the glycosylation reagents of the invention can be synthesized using a variety of synthetic methodologies. One of these methodologies is set forth herein in the synthesis of a specific mannose-containing derivatization reagent (glycosylation reagent):

A protected PEG linker (HO—CH$_2$CH$_2$—(OCH$_2$CH$_2$)$_7$—O—CH$_2$CH$_2$COOR) is synthesized by mono-protecting the nonaethylene glycol (HO—CH$_2$CH$_2$—(OCH$_2$CH$_2$)$_8$—OH) with TBDMS-Cl. The free hydroxyl group is converted to a chloride by reacting the mono-protected PEG with thionyl chloride, using pyridine as a proton scavenger under elevated temperature (60° C.). The chloride is further converted to a carboxyl group by the reaction with Mg° in anhydrous ether and further reacting the resulting organometallic derivative (TBDMS-O—CH$_2$CH$_2$—(OCH$_2$CH$_2$)$_7$—O—CH$_2$CH$_2$MgCl) with carbon dioxide. Following acidification with H$_2$SO$_4$, the carboxylic acid (TBDMS-O—CH$_2$CH$_2$—(OCH$_2$CH$_2$)$_7$—O—CH$_2$CH$_2$COOH) is esterified with methanol to yield the corresponding ester (TBDMS-O—CH$_2$CH$_2$—(OCH$_2$CH$_2$)$_7$—O—CH$_2$CH$_2$COOCH$_3$). The t-butyldimethylsilyl protecting group is removed by treatment with tetrabutylammonium fluoride in THF to yield the mono-protected PEG linker, HO—CH$_2$CH$_2$—(OCH$_2$CH$_2$)$_7$—O—CH$_2$CH$_2$COOR wherein R═CH$_3$.

A mixture of 1,2,3,4-tetra-O-acetyl-D-mannose, the mono-protected PEG linker (HO—CH$_2$CH$_2$—(OCH$_2$CH$_2$)$_7$—O—CH$_2$CH$_2$COOR wherein R═CH$_3$) and ZnCl$_2$ is heated at 100-110° C. with stirring under reduced pressure, with a soda lime trap interposed between the reaction vessel and the vacuum source to remove acetic acid, for 4 hours. The resulting mass is dissolved in ethyl acetate, washed twice with water and dried over anhydrous Na$_2$SO$_4$. The ethyl acetate is removed under reduced pressure and the residue is chromatographed on a silica gel 60 chromatography column to give the 1-PEG-2,3,4-tri-O-acetyl-D-mannoside. The product is further chromatographed to separate the α and β anomers. The α anomer is deprotected by treatment with 2N sodium methoxide. The resulting solid is filtered and washed with ethyl alcohol to give the corresponding salt sodium salt (Mannose-(α1)-O—CH$_2$CH$_2$—(OCH$_2$CH$_2$)$_7$-β-CH$_2$CH$_2$COONa).

The glycosylating reagent can be conjugated to a target protein by using a carbodiimide agent, such as DCC (dicyclohexylcarbodiimide). Alternatively, the carboxylic acid can be activated by transforming it to an N-hydroxy succinimide ester (NHS) or sulfo-NHS ester by reacting the carboxylic acid with the N-hydroxy succinimide in the presence of an appropriate carbodiimide coupling reagent, such as EDC (1-ethyl-3-(3-diaminomethylpropyl)carbodiimide).

Example 2

Synthesis of M6P(α1)-O—CH$_2$CH$_2$—(OCH$_2$CH$_2$)$_7$—O—CH$_2$CH$_2$COOH

The following describes another exemplary methodology for the synthesis of a specific mannose-containing derivatization (glycosylation) reagent having a carboxylate functional group.

A protected PEG linker (HO—CH$_2$CH$_2$—(OCH$_2$CH$_2$)$_7$—O—CH$_2$CH$_2$COOR) is synthesized as described in Example 1.

A mixture of 1,2,3,4-tetra-O-acetyl-D-mannose, the mono-protected PEG linker (HO—CH$_2$CH$_2$—(OCH$_2$CH$_2$)$_7$—O—CH$_2$CH$_2$COOR wherein R═CH$_3$) and ZnCl$_2$ is heated at 100-110° C. with stirring under reduced pressure, with a soda lime trap interposed between the reaction vessel and the vacuum source to remove acetic acid, for 4 hours. The resulting mass is dissolved in ethyl acetate, washed twice with water and dried over anhydrous Na$_2$SO$_4$. The ethyl acetate is removed under reduced pressure and the residue is chromatographed on a silica gel 60 chromatography column to give the 1-PEG-2,3,4-tri-O-acetyl-D-mannoside. The product is further chromatographed to separate the α and β anomers.

To a solution of 2,3,4-tri-O-acetyl-mannose-(α1)-O—CH$_2$CH$_2$—(OCH$_2$CH$_2$)$_7$-β-CH$_2$CH$_2$COOCH$_3$ in dry pyridine is added diphenyl chlorophosphate dropwise at room temperature over 1 hour and the mixture is allowed to stand at room temperature overnight. The mixture is the heated at 40° C. for 3 hours. The solvent is evaporated under reduced pressure and the residue chromatographed on a silica gel chromatography column (silica gel 60) to give 2,3,4-tri-O-acetyl-6-diphenylphosphate-mannose-(α1)-β-CH$_2$CH$_2$—(OCH$_2$CH$_2$)$_7$—O—CH$_2$CH$_2$COOCH$_3$.

The latter is dissolved in dry methanol and is hydrogenated in the presence of platinum oxide catalyst at slightly greater than atmospheric pressure. When the calculated amount of hydrogen is taken up, the catalyst is removed by filtration and the solvent evaporated under reduced pressure. The residue is chromatographed on a silica gel chromatography column (silica gel 60) to give 2,3,4-tri-O-acetyl-M6P-(α1)-β-$CH_2CH_2$—$(OCH_2CH_2)_7$—O—$CH_2CH_2COOCH_3$, which is further deprotected by treatment with 2N sodium methoxide. The resulting solid is filtered and washed with ethyl alcohol to give the tri-sodium salt (M6P(α1)-O—$CH_2CH_2$—$(OCH_2CH_2)_7$-β-$CH_2CH_2COONa$).

Following are the spectral data of (M6P(α1)-O—$CH_2CH_2$—$(OCH_2CH_2)_7$—O—$CH_2CH_2COOH$):

$^1$H NMR (400 MHz, $D_2O$): δ=4.72 (m, 1H), 3.82 (m, 1H), 3.75 (m, 1H), 3.71-3.65 (m, 1H), 3.65 (t, J=6.1 Hz, 2H), 3.61-3.57 (m, 2H), 3.55 (m, 32H), 3.5 (m, 1H), 2.52 (t, J=6.1 Hz, 2H) ppm;

$^{13}$C-NMR ($D_2O$): δ=176.75, 100.21, 71.88, 71.79, 70.50, 70.09, 69.73, 69.65, 66.62, 66.50, 66.34, 64.15, 34.81 ppm;

$^{31}$P-NMR ($D_2O$): δ=1.69 (s);

MS (ESI): 603.4 (M-$PO_3H_2$).

Example 3

Characterization of Glycosylating Reagents

The glycosylating reagents M6P-$PEG_{12}$-COOH and M6P-$PEG_8$-maleimide were prepared using common methodologies.

Following are the spectral data of M6P-$PEG_{12}$-COOH:

$^1$H NMR (400 MHz, $D_2O$): δ=4.90 (m, 1H), 4.12 (m, 1H), 3.98 (m, 1H), 3.94-3.88 (m, 1H), 3.87-3.83 (m, 1H), 3.81 (t, J=6.1 Hz, 2H), 3.78-3.74 (m, 1H), 3.73-3.68 (m, 48H), 2.67 (t, J=6.1 Hz, 2H) ppm;

$^{13}$C-NMR ($D_2O$): δ=176.55, 100.22, 71.87, 71.80, 70.51, 70.09, 69.73, 69.66, 69.61, 66.62, 66.42, 66.34, 64.10, 34.65 ppm; and $^{31}$P-NMR ($D_2O$): δ=1.64 (s).

Following are the spectral data of M6P-$PEG_8$-maleimide:

$^1$H NMR (400 MHz, $D_2O$): δ=6.86 (m, 1H), 4.90 (m, 1H), 3.75 (m, 1H), 4.12 (m, 1H), 3.98 (m, 1H), 3.92-3.83 (m, 1H), 3.76 (m, 2H), 3.74-3.67 (m, 28H), 3.62 (t, J=5.2 Hz, 2H), 3.55 (t, J=6.4 Hz, 2H), 3.39 (s, 1H), 3.36 (t, J=5.2 Hz, 2H), 2.28 (t, J=7.6 Hz, 2H), 1.91 (quintet, J=7.2 Hz, 2H) ppm; and $^{31}$P-NMR ($D_2O$): δ=1.64 (s).

Example 4

M6P Derivatization of α-galactosidase-A Amines

One methodology for conjugating moieties to human α-galactosidase-A is by targeting the primary amines of the side chains of lysine residues on the surface of the protein. Human α-galactosidase-A has 16 Lysine residues in its sequence, most of which are solvent accessible.

The following describes an exemplary procedure according to this methodology.

1 mg of M6P(α1)-O—$CH_2CH_2$—$(OCH_2CH_2)_7$—O—$CH_2CH_2COONa$, prepared as described in Example 2 hereinabove, was activated by reaction with EDC (1-ethyl-3-[3-dimethylaminopropyl]carbodiimide hydrochloride) and S—NHS (sulfo-N-hydroxysuccinimide) in a 1:1.3:1.3 molar ratio. The reaction was performed in 37.4 µl DMSO (dimethyl sulfoxide), overnight, at room temperature. The obtained reaction mixture was used without purification.

The obtained reaction mixture was added to 800 µl of a solution of α-galactosidase A (1.65 mg/ml) in a phosphate buffer solution (pH 7.4, 50 mM). The solution was mixed well and the reaction was then allowed to proceed overnight at 4° C. The modified protein was separated from low-molecular weight moieties by dialysis (10,000 Da cut-off) against phosphate buffer (pH 6, 25 mM).

As shown in FIG. 4, conjugation of M6P-$PEG_8$-$CO_2H$ to α-galactosidase-A resulted in an increase in the mass of the α-galactosidase-A, as measured by SDS-PAGE.

As shown in FIG. 5, conjugation of M6P-$PEG_8$-$CO_2H$ to α-galactosidase-A resulted in a shift of the pI of the α-galactosidase-A.

These results presented in FIGS. 4 and 5 confirm the successful conjugation of M6P-$PEG_8$-$CO_2H$ to the protein.

Conjugation of M6P-$PEG_8$-$CO_2H$ to the protein was performed on a larger scale using the methodology described above.

4.1 mg of S—NHS, 10 mg of M6P(α1)-O—$CH_2CH_2$—$(OCH_2CH_2)_7$—O—$CH_2CH_2COONa$ (in 200 µl of DMSO) and 4.3 mg of EDC (in 93 µl DMSO) were mixed, and the reaction mixture was stored overnight at room temperature.

263 µl of the obtained reaction mixture was added to 7.2 ml phosphate buffer solution (50 mM, pH=7.1) containing 1.65 mg/ml α-galactosidase-A. The obtained reaction mixture was stirred at 4° C. overnight. The modified protein was separated from low-molecular weight moieties by dialysis (10,000 Da cutoff) against phosphate buffer (pH 6, 25 mM).

As shown in FIG. 6, conjugation of M6P-$PEG_8$-$CO_2H$ to α-galactosidase-A resulted in a shift of the pI of the α-galactosidase-A.

As shown in FIG. 7, conjugation of M6P-$PEG_8$-$CO_2H$ to α-galactosidase-A resulted in an increase in the mass of the α-galactosidase-A, as measured by SDS-PAGE.

Figure 8:
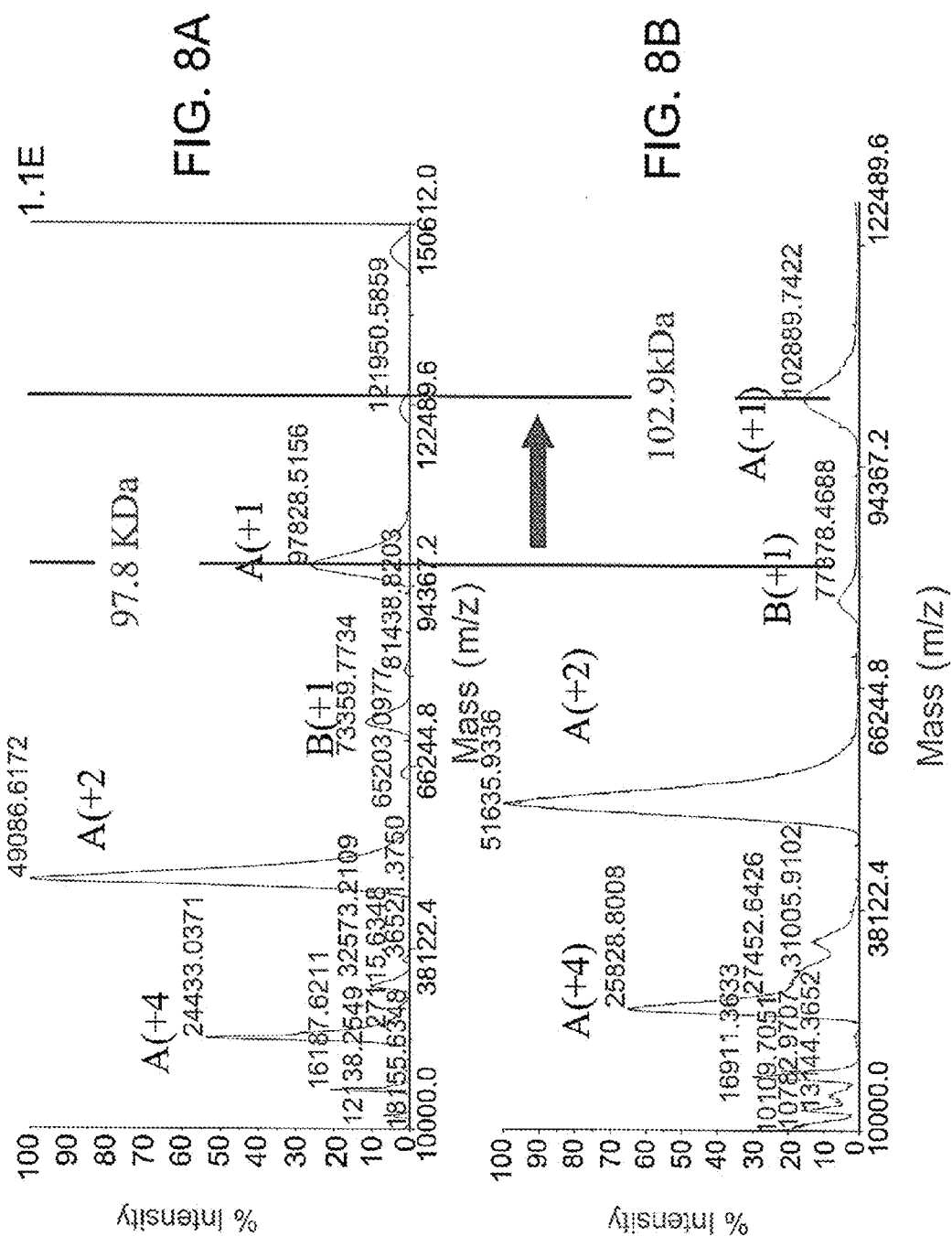

As shown in FIG. 8, the MALDI-TOF mass spectrum of homo-dimeric α-galactosidase-A conjugated to M6P-$PEG_8$-$CO_2H$ exhibits an increase of 5.1 kDa in relation to the mass spectrum of the native homo-dimeric α-galactosidase-A, indicating an average incorporation of 7-8 M6P-$PEG_8$-$CO_2H$ moieties per homo-dimer of α-galactosidase-A.

Example 5

M6P Derivatization of Glucocerebrosidase (GCD)

13 mg of M6P-$PEG_8$-COOH in 260 ml DMSO was added to 4.7 mg of S—NHS. 80 µl of freshly prepared EDC solution (5.5 mg in 110 µl DMSO) was then added. The obtained reaction mixture was shaken overnight at room temperature.

The reaction mixture was then added to 12 mg GCD in 9 ml of phosphate buffer (50 mM, pH 7.4). The reaction mixture was shaken for 2 hours at room temperature. The solution was then dialyzed using Vivaspin (6 ml, cutoff of 10,000 Da) against saline.

As shown in FIG. 9, conjugation of M6P-$PEG_8$-$CO_2H$ to GCD resulted in a shift of the pI of the GCD.

As shown in FIG. 10, conjugation of M6P-$PEG_8$-$CO_2H$ to GCD resulted in an increase in the mass of the GCD, as measured by SDS-PAGE.

As shown in FIGS. 11A-B, the MALDI-TOF mass spectrum of GCD conjugated to M6P-$PEG_8$-$CO_2H$ exhibits an increase of 2.5 kDa in relation to the mass spectrum of the native GCD, indicating an average incorporation of 3-4 M6P-$PEG_8$-$CO_2H$ moieties per GCD molecule.

These results presented in FIGS. 9-11 confirm the successful conjugation of M6P-$PEG_8$-$CO_2H$ to GCD.

Example 6

Preparation of M6P-Derivatized GFP

GFP (Green fluorescent protein) was modified by M6P-$PEG_8$-COOH, using the methodology described in Example 3, to test uptake of a modified protein via M6P receptor.

M6P-PEG$_8$-COOH was activated by EDC and S—NHS in a 1:1.1:1.1 ratio (M6P-PEG$_8$-COOH:EDC:S—NHS) in DMSO. After the activation, GFP was added in phosphate buffer (66 mM, pH 8) and the reaction mixture was stored overnight at 4° C. The results were analyzed by SDS-PAGE (12%), isoelectric focusing and mass spectroscopy.

As shown in FIG. 12A, conjugation of M6P-PEG$_8$-CO$_2$H to GFP resulted in an increase in the mass of the GFP, as measured by SDS-PAGE.

As shown in FIG. 12B, conjugation of M6P-PEG$_8$-CO$_2$H to GFP resulted in a shift of the pI of the GFP.

As shown in FIGS. 13A-B, conjugation of M6P-PEG$_8$-CO$_2$H to GFP resulted in an increase in the mass of the GFP, as measured by mass spectrometry.

The above results confirm that M6P-PEG$_8$-CO$_2$H was successfully conjugated to GFP.

Example 7

M6P Derivatization of α-Galactosidase-A Through Protein Thiols

Maleimide-activated reagents are effective for protein modification of sulfhydryl groups. Maleimide groups react efficiently and specifically with free (reduced) sulfhydryls at pH 6.5-7.5 to form stable thioether bonds. Thus, a suitable reagent for M6P derivatization of α-galactosidase-A through protein thiols is a maleimide activated M6P-PEG.

Protein modification via free sulfhydryl(thiol) groups is effected via conjugation to free thiol moieties of the side chain of cysteine residues.

Human α-galactosidase-A has 12 cysteine residues, 10 of which are engaged in intra-molecular disulfide bonds and cannot be targeted by maleimide activated M6P-PEGs. One of the free cysteine residues (Cys 90) is buried in the protein and is not accessible for conjugation. However, Cys 174 is relatively exposed to the solvent and can be used for mono-derivatization of human α-galactosidase-A.

As human α-galactosidase A has only one cysteine residue available for conjugation, the lysine residues of α-galactosidase A were thiolated using Traut reagent (2-iminothiolane hydrochloride) and then coupled to a M6Pylation reagent terminated with the maleimide reactive group.

A stock solution of 10 mg/ml Traut's reagent in DMSO was prepared just before the reaction. 80 μl of the Traut's stock solution was added to 1.6 ml of α-galactosidase A (3.2 mg/ml) that was diluted with 1.6 ml of phosphate buffer (pH 8, 50 mM). Following incubation for 30 minutes at room temperature, 4 ml of phosphate buffer (pH 6, 200 mM) was added. The obtained reaction mixture was dialyzed via Vivaspin 6 (Sartorius) with a 50 kDa cutoff in to phosphate buffer (pH 6 50 mM).

1 mg of M6P-PEG$_8$-maleimide (as depicted in FIG. 1B) in 20 μl DMSO was added to the reaction mixture, and the reaction mixture was then shaken for 8 hours at 4° C. An additional 1 mg of M6P-PEG$_8$-maleimide was then added. After being kept for two days at 4° C., the obtained reaction mixture was purified using dialysis via Vivaspin with a 50 kDa cutoff in saline solution.

The derivatized protein was further analyzed by SDS-PAGE and isoelectric focusing.

As shown in FIG. 14A, conjugation of M6P-PEG$_8$-maleimide to α-galactosidase-A resulted in a shift of the pI of the α-galactosidase-A.

As shown in FIG. 14B, conjugation of M6P-PEG$_8$-maleimide to α-galactosidase-A resulted in an increase in the mass of the α-galactosidase-A, as measured by SDS-PAGE.

These changes in pI and SDS-PAGE migration correspond to an average incorporation of 1-2 M6P-PEG$_8$-Mal moieties per α-galactosidase-A dimer as indicated in the MALDI-TOF MS results (not shown).

Example 8

M6P Derivatization of α-Galactosidase-A Through Protein Carboxylates

Human α-galactosidase-A has 44 carboxylic acid-containing side chains in its sequence, being residues of aspartic and glutamic acids. An M6P-PEG reagent according to the present embodiments can be coupled to the solvent-exposed carboxylic acid residues by utilizing an amine terminated M6P-PEG derivative, and a carbodiimide catalyst. In order to avoid cross-linking between α-galactosidase-A amines and carboxylic residues, a large excess of the M6P-PEG reagent is used.

Following is an exemplary synthesis for conjugating amine-terminated M6P-PEGs to human α-galactosidase-A via protein carboxylates.

α-Galactosidase-A (1 mg/mL) in an appropriate buffer (pH 6) is added to a solution containing the amine terminated M6P-PEG reagent in 50-fold molar excess, DCC (in 60-fold molar excess) and DMAP (in 100-fold molar excess) at 4° C. The reaction mixture is kept at 4° C. with gentle agitation for 12 hours and is further dialyzed to remove excess reagents and by products. The derivatized protein is analyzed by SDS-PAGE.

The reaction can optionally be performed in the presence 1-deoxynojirimycin, or any other α-galactosidase-A inhibitor, in order to avoid loss of enzymatic activity due to conjugation of the M6P-PEG reagent to the aspartic acid residues within the active site.

Example 9

Mannose Derivatization of Proteins

A glycosylating reagent comprising mannose (obtained, for example, as described in Example 2 hereinabove, wherein the phosphorylation of the mannose moiety is omitted) can be conjugated to a protein's primary amine groups by using a carbodiimide agent, such as DCC or EDC, optionally catalyzed by a proton scavenger such as dimethylamino pyridine (DMAP). As described in Example 4, the terminal carboxylic acid can be activated by transforming it to an NHS or sulfo-NHS ester by the reaction of the carboxylic acid with N-hydroxy succinimide in the presence of an appropriate carbodiimide coupling reagent, such as EDC.

Following is an exemplary methodology for conjugating a mannose-PEG-COOH reagent to a protein.

Glycosylating reagent activation: A 10-fold molar excess of EDC is added to a glycosylating reagent mannose (α1)-O—CH$_2$CH$_2$—(OCH$_2$CH$_2$)$_7$—O—CH$_2$CH$_2$COOH, which is prepared according to the methodology described in Example 2, to give a 2 mM solution in a 0.1 M phosphate citrate buffer, pH 5.0. NHS is further added in a 25-fold molar excess. The reaction components are allowed to react with agitation for 15 minutes at room temperature. The pH is elevated to 6.0 and human GCD is added to the solution to give a 5-fold molar excess of mannose-PEG-NHS. The solution is mixed well and the reaction is allowed to proceed overnight at 4° C. The modified protein is separated from low-molecular weight moieties by dialysis (10,000 Da cutoff).

As with α-galactosidase-A, other proteins can typically be derivatized at free and accessible thiol groups of cysteine residues and carboxylic acid groups of aspartic acid and glutamic acid residues.

Example 10

Activity of Derivatized α-Galactosidase-A

A M6P-derivatized α-galactosidase-A, as described, for example, in Example 4 hereinabove, is assayed for its catalytic activity following its M6Pyaltion, in order to ensure that the derivatization with M6P did not impair the catalytic activity of the enzyme.

Non-modified α-galactosidase-A is assayed in order to provide a control.

The modified or non-modified enzyme is dialyzed (×2) against 2 Liters of citrate phosphate buffer (20 mM, pH 4.6), diluted to give a 50 nM solution, and is allowed to react at 37° C. with its substrate analog, p-nitrophenyl-α-D-galactopyranoside (5000 μM). The reaction is allowed to continue for 15 minutes and is quenched with 5N NaOH. The concentration of the hydrolysis reaction, p-nitrophenol, is measured spectrophotometrically (401 nm) in a 1 cm cuvette and quantified using a p-nitrophenol calibration curve. The α-galactosidase-A activity is defined as the μM of p-nitrophenol liberated per 1 minute per 1 nM of enzyme.

The activity of the M6P-derivatized α-galactosidase-A prepared as described in Example 4 was tested as described herein. The α-galactosidase-A was found to have retained enzymatic activity following derivatization.

Example 11

Activity of Mannose Derivatized GCD

A derivatized glucocerebrosidase as described in Example 9 hereinabove is assayed for its catalytic activity following its mannose derivatization, so as to ensure that the derivatization did not impair the catalytic activity of the enzyme.

Following is an exemplary methodology for assaying the catalytic activity of mannose derivatized GCD. The enzyme is dialyzed (×2) against 2 liters of phosphate citrate buffer (0.1M, pH 5.5), diluted to give a 25 nM solution and allowed to react at 37° C. with its substrate analog, p-nitrophenyl-beta-D-glucopyranoside (5000 μM). The reaction is allowed to continue for 15 minutes and is then quenched with 5 N NaOH. The concentration of the hydrolysis product, p-nitrophenol, is measured spectrophotometrically (401 nm) in a 1 cm cuvette and quantified using a p-nitrophenol calibration curve. The GCD activity is defined as the μM of p-nitrophenol liberated per 1 minute per 1 nM of enzyme.

Example 12

Biochemical Properties of M6P and Mannose Derivatized GCD

A derivatized glucocerebrosidase as described in Example 9 hereinabove is assayed for its biochemical properties following its mannose or M6P derivatization, so as to ensure that the derivatization with mannose or M6P residues does not impair the catalytic characteristics of the enzyme, and to establish its new biochemical properties, including its molecular weight (Mw), isoelectric point (pI), and its Michaelis-Menten constant ($K_M$) as well as its maximum velocity ($V_{max}$) and catalytic coefficient ($k_{cat}$). Furthermore, human GCD is a monomer and further analyses are carried out to ensure that the enzyme retains its monomeric form following mannose derivatization.

The Mw of the derivatized GCD is assayed by mass spectrometry (MALDI-TOF). The existence of the monomeric form can also be established by a gel-filtration analysis using an analytical HPLC. The Michaelis-Menten kinetics are carried out at an enzyme concentration of 30 nM using p-nitrophenyl-beta-D-glucopyranoside as substrate, at substrate concentrations ranging from 50 μM to 10000 μM. Reaction mixtures are incubated at 37° C. for 10 to 180 minutes, ensuring conversion levels do not exceed 5%. Reactions are then quenched with 5N NaOH and the level of the p-nitrophenol product is quantified spectrophotometrically using a calibration curve (401 nm). The velocity of each reaction is calculated by dividing the concentration of p-nitrophenol by the reaction time and the velocity vs. substrate concentration curve (Michaelis-Menten plot) is used to calculate the enzyme's $K_M$, $V_{max}$ and $k_{cat}$, using non-linear regression.

Non-modified GCD is assayed as described above in order to provide a comparison.

Example 13

In-vitro Uptake of Derivatized α-Galactosidase-A

Targeting and uptake of α-galactosidase-A to target cells and tissues is mediated by the M6P receptor and can be determined using a fibroblast cell line expressing M6P receptors.

The uptake of α-galactosidase A conjugated with either M6P-PEG$_{12}$-CO$_2$H (see FIG. 1A) or M6P-PEG$_8$-maleimide (see FIG. 1B) was compared with that of non-modified α-galactosidase A.

Fibroblasts (GMO2775, Coriell institute) of Fabry affected Caucasian male were pre-cultured in 48-well plates (1×10$^5$ cells per ml) with DMEM (D5546, Sigma) containing 12% FBS, 200 mM L-Glutamine, MEM Vitamins solution (01-326-1, Biological industries Ltd., Israel), essential and non-essential amino acid solutions (Biological industries Ltd., Israel, 01-325-1 and 01-340-1, respectively) and Penicillin-Streptomycin solution, 10,000 units per ml Penicillin G. α-Galactosidase-A was diluted in medium, and 50 μl of the solution were then added to each well to obtain a final concentration of 0.5-30 μg/ml. Following incubation of 5 hours, the medium was collected. Cells were washed with PBS and trypsinized. Following neutralization, cells were centrifuged at 2,000 g for 4 minutes. Pellets were washed in PBS and centrifuged again. Pellets were vigorously pipetted with 60 μl of lysis buffer containing protease inhibitors. Lysed cells were frozen and thawed twice and α-galactosidase A uptake was measured by Western blotting, as described hereinabove.

As shown in FIGS. 15A-B, uptake of α-galactosidase A into Fabry fibroblasts was increased following conjugation with either M6P-PEG$_{12}$-CO$_2$H or M6P-PEG$_8$-maleimide.

Example 14

In-vivo Uptake of α-Galactosidase-A Derivatized with M6P-PEG$_8$-CO$_2$H

Targeting and uptake of α-galactosidase-A to target organs and tissues is mediated by the M6P receptor and was determined by measuring the levels of alpha-galactosidase-A in the tissues of "Fabry Mice" (Jackson B6J129Gla). α-Galactosidase-A accumulation in mouse liver and spleen following i.v. administration of derivatized α-galactosidase-A and untreated α-galactosidase-A is measured by enzymatic activity.

Fabry mice received a single intravenous (i.v.) bolus injection of α-galactosidase-A or derivatized α-galactosidase-A (conjugated to M6P(α1)-O—CH$_2$CH$_2$—(OCH$_2$CH$_2$)$_7$—O—CH$_2$CH$_2$COONa, as described in Example 4 hereinabove, and referred to herein as M6P-PEG$_8$-CONH-α-galactosidase-A). Prior to injection, each sample for injection was tested for protein activity as described hereinbelow. Animals were sacrificed 24 hours or 7 days post-injection. The experiments performed are summarized in Table 1 below.

TABLE 1 in vivo M6P-PEG$_8$-CONH-α-Gal-A experiments

| Group | 24 hours | 7 days | Number of animals | Dosing volume (ml/kg) | Comments |
|---|---|---|---|---|---|
| α-Gal-A 18.75 mg/kg | 3 | 3 | 6 mice | 5 | Test group |
| M6P-PEG$_8$-CONH-α-Gal-A 3 mg/kg | 4 | 4 | 8 mice | | Test group |
| M6P-PEG$_8$-CONH-α-Gal-A 10 mg/kg | 4 | 4 | 8 mice | | Test group |
| Saline | 3 | 3 | 6 mice | | Negative control |

Prior to sacrifice (on Day 1 or 7) individual blood samples were obtained by retro-orbital sinus bleeding under anesthesia. The volume of blood obtained did not exceed 15% of the circulating blood volume (72 ml/kg). Samples were collected to pre-labeled Li-Heparinized coated tubes (mini collect 0.5 mL tubes, Greiner Bio One, Cat# 6-450479), and centrifuged to obtain plasma samples.

Following blood collection, animals were perfused (to remove heme, which interferes with the fluorometric a-Gal A enzymatic assay) with 0.9% saline, administered to the left ventricle of the heart, with concurrent severing of the right atrium or jugular. Perfusion was performed until no blood poured from the right atrium or jugular, after which the lungs, liver, spleen, heart and kidneys were collected from each mouse. Each sample was frozen immediately in liquid nitrogen and then transferred to storage at about −70° C. for enzyme or Gb-3 analyses.

Soluble tissue samples were assayed for α-galactosidase-A activity as described herein 24 hours after injection.

As shown in FIGS. 16A-B and FIG. 17, uptake of M6P-PEG$_8$-CONH-α-galactosidase A into the liver was greater than uptake of plant recombinant α-galactosidase-A.

As shown in FIGS. 18A-B, uptake of M6P-PEG$_8$-CONH-α-galactosidase A into the spleen was greater than uptake of plant recombinant α-galactosidase-A.

As shown in FIGS. 19A-B, uptake of M6P-PEG$_8$-CONH-α-galactosidase A into the heart was greater than uptake of plant recombinant α-galactosidase-A.

As shown in FIGS. 20A-B, uptake of M6P-PEG$_8$-CONH-α-galactosidase A into the lungs was greater than uptake of plant recombinant α-galactosidase-A.

As shown in FIGS. 21A-B, uptake of M6P-PEG$_8$-CONH-α-galactosidase A into the kidneys was greater than uptake of plant recombinant α-galactosidase-A.

Soluble tissue samples were also assayed for α-galactosidase-A activity 7 days after injection.

As shown in FIGS. 22A-B, 23 and 24, uptake of M6P-PEG$_8$-CONH-α-galactosidase A remained higher than uptake of plant recombinant α-galactosidase A in spleen, liver and heart tissues 7 days after injection.

In kidney and lung tissue, no α-galactosidase activity was detected above background levels for either modified or unmodified α-galactosidase A.

In addition, plasma samples were assayed for α-galactosidase A activity. High plasma levels indicate lack of uptake into the cells.

As shown in FIG. 25, unmodified α-galactosidase A remained in the plasma both 24 hours and 7 days after injection, whereas, M6P-PEG$_8$-CONH-α-galactosidase A was absent from plasma.

The results presented hereinabove demonstrate that modification of plant recombinant α-galactosidase A with an M6P-PEG$_8$-COOH moiety considerably improved uptake of the α-galactosidase A in a wide variety of tissue types both 24 hours and 7 days after injection.

Example 15

In-vivo Uptake of Additional Forms of Derivatized α-Galactosidase-A

α-Galactosidase A was derivatized with the glycosylation reagents M6P-PEG$_8$-maleimide (depicted in FIG. 1B) and M6P-PEG$_{12}$-CO$_2$H (depicted in FIG. 1A). The resulting conjugates are referred to herein as M6P-PEG$_8$-maleimide-α-galactosidase-A and M6P-PEG$_{12}$-CONH-α-galactosidase-A, respectively.

Uptake of the derivatized α-galactosidase A was determined in vivo, using the methodology described in Example 14.

Preliminary results were obtained and are shown in FIGS. 26A-B.

As shown in FIGS. 26A-B, the uptake of the derivatized α-galactosidase A into heart (FIG. 26A) and lung (FIG. 26B) tissue was greater in most groups tested than uptake of non-derivatized α-galactosidase A.

Determination of optimal conditions for conjugation with the aforementioned glycosylation reagents is currently ongoing, in order to allow for more consistent results.

Example 16

In-vitro Uptake of Mannose Derivatized GCD

Targeting and uptake of GCD to macrophages is mediated by the mannose/N-acetylglucosamine (Man/GlcNAc) receptor and can be determined using murine thioglycolate-elicited peritoneal macrophages or macrophage cell line expressing Man/GlcNAc receptors.

Following is an exemplary methodology for assaying the in-vitro uptake of mannose derivatized GCD. Rat macrophage cell line (ATCC# R8383) is cultured in DMEM (Beit Haemek, Israel) containing 10% fetal calf serum, plated at 2-5×10$^5$ cells/well in 96-well plates, and incubated at 37° C. for 90 minutes with culture medium containing GCD. Medium is subsequently removed, cells are washed three times with PBS, and activity is measured in cell extract.

The activity of GCD taken up by the cells is determined by enzymatic activity assay using p-nitrophenyl-beta-D-glucopyranoside. The assay buffer contains 4 mM p-nitrophenyl-beta-D-glucopyranoside, 1.3 mM EDTA, 0.15% Triton X-100, 0.125% sodium taurocholate, 60 mM phosphate-citrate buffer, pH 6.0. After 60 minutes at 37° C., the reaction is terminated using 5N NaOH, and the reaction product (p-nitrophenol) is determined by its absorbance at 405 nm.

Example 17

In-vivo Uptake of Mannose Derivatized GCD

Targeting and uptake of GCD to macrophages in spleen and liver is mediated by the mannose/N-acetylglucosamine (Man/GlcNAc) receptor and can be determined by measuring the levels of GCD in the tissues, and the levels of glucosylceramide, the substrate of GCD. GCD accumulation in mouse liver and spleen following i.v. administration of derivatized GCD and untreated GCD is measured by enzymatic activity and analysis of glucosylceramide levels. Following is an exemplary methodology for assaying the in-vivo uptake of mannose derivatized GCD.

Animals, Materials and Experimental Procedures:

Mice: BALB/C female mice 7-8 weeks, n=5.

i.v. administration: Mice are i.v. injected with derivatized GCD and untreated GCD. Animals are sacrificed after 1, 2, 4 and 18 hours post-injection. The liver and spleen from each animal are removed, frozen in liquid nitrogen and stored at −70° C. until analysis.

Preparation of Liver and Spleen Tissue Samples: Each tissue sample is washed with 0.9% NaCl and homogenized with homogenization buffer (60 mM phosphate citrate, 1.5% Triton X-100, 1 mM PMSF), 5 ml buffer per gram tissue using a ULTRA-TURRAX T 25 basic IKA-WERKE homogenizer at low speed (11,000-13,000 l/min) for 45-60 seconds, on ice. Samples are centrifuged at 10,000 g for 10 minutes at 4° C. The supernatant is collected and divided to aliquots, and frozen at −70° C. until analysis.

In vitro glycosidase activity assay: The activity of GCD taken up by the cells is determined by enzymatic activity assay using p-nitrophenyl-beta-D-glucopyranoside. The assay buffer contains 4 mM p-nitrophenyl-beta-D-glucopyranoside, 1.3 mM EDTA, 0.15% Triton X-100, 0.125% sodium taurocholate, 60 mM phosphate-citrate buffer, pH 6.0. After 60 minutes at 37° C., the reaction is terminated using 5N NaOH, and the reaction product (p-nitrophenol) is determined by its absorbance at 405 nm.

Example 18

In-vitro Uptake of Derivatized GFP

In order to investigate the general utility of M6P derivatization to increase uptake into cells, GFP (green fluorescent protein) was conjugated to an M6P-PEG$_8$-CH$_2$CH$_2$CO$_2$H moiety, using the protein glycosylation procedure described hereinabove (see, Example 6.

Following 1 day of culture at 37° C., the cell medium was replaced with fresh serum-free medium containing 1 μM of GFP or 1 μM M6P-PEG-GFP. Cells were incubated for 24 hours and then visualized using an inverse-fluorescent microscope.

As shown in FIGS. 27A-B, uptake of M6P-PEG$_S$-GFP was greater than uptake of GFP.

Example 19

Optimization of Reaction Conditions for Conjugation

α-Galactosidase A was conjugated with 5 kDa mPEG-COOH that was preactivated with EDC and sulfo-NHS. The effect of reaction conditions on the efficacy of conjugation was tested.

The α-galactosidase A was reacted with 100 equivalents of 5 kDa mPEG using various concentrations of EDC and sulfo-NHS. The molar ratios of the reactants in each group are summarized in Table 2.

TABLE 2

| Molar equivalents of reactants in experimental groups | | | | | | | | |
|---|---|---|---|---|---|---|---|---|
| | group | | | | | | | |
| | 1 | 2 | 3 | 4 | 5 | 6 | 7 | 8 |
| PEG | 100 | 100 | 100 | 100 | 100 | 100 | 100 | 100 |
| EDC | 100 | 130 | 200 | 100 | 100 | 130 | 200 | 100 |
| S-NHS | 100 | 130 | 200 | 100 | 100 | 130 | 200 | 100 |
| α-Gal | 1 | 1 | 1 | 1 | 1 | 1 | 1 | 1 |

The preactivation of PEG in all the experiments was performed in DMSO. The coupling reaction was performed at pH=7.4.

The resulting conjugates were examined using SDS-PAGE.

As shown in FIG. 28, higher ratios of EDC and sulfo-NHS to PEG and protein resulted in higher molecular weights, indicating more effective conjugation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A conjugate comprising a single lysosomal protein and a saccharide moiety being covalently linked to said lysosomal protein via a non-hydrophobic linker, said linker being a non-saccharide linker and comprising a poly(alkylene glycol) of at least 18 atoms in length, and said saccharide moiety being a M6P.

2. The conjugate of claim 1, wherein said linker is attached to an anomeric carbon of said saccharide moiety.

3. The conjugate of claim 2, wherein said linker is attached to said anomeric carbon via a bond having an α configuration.

4. The conjugate of claim 1, wherein said poly(alkylene glycol) comprises poly(ethylene glycol) (PEG).

5. A conjugate comprising a single protein and a saccharide moiety being covalently linked to said protein via a non-hydrophobic linker, said linker being a non-saccharide linker and comprising a poly(alkylene glycol) of from 24 to 36 atoms in length, and said saccharide moiety being a monosaccharide.

6. A conjugate comprising a single protein and a saccharide moiety being covalently linked to said protein via a non-hydrophobic linker, said linker being a non-saccharide linker and comprising a poly(alkylene glycol) of at least 18 atoms in length, said poly(ethylene glycol) comprising from 8 to 12 ethylene glycol units, and said saccharide moiety being a monosaccharide.

7. The conjugate of claim 1, wherein said linker is a branched linker comprising at least two linear chemical moieties which are covalently linked to one another, each of said linear chemical moieties being attached to said saccharide moiety, such that said linker is attached to at least two saccharide moieties, each of said saccharide moieties being a M6P.

8. The conjugate of claim 7, wherein said branched linker comprises at least two linear poly(alkylene glycol) moieties which are covalently linked to one another.

9. The conjugate of claim 5, wherein said monosaccharide is a sialic acid.

10. The conjugate of claim 5, wherein said monosaccharide is a hexose.

11. The conjugate of claim 10, wherein said hexose is a D-hexose.

12. The conjugate of claim 11, wherein said linker is attached to said anomeric carbon via a bond having α configuration.

13. The conjugate of claim 5, wherein said monosaccharide is selected from the group consisting of a mannose and a M6P.

14. The conjugate of claim 1, wherein said protein is a recombinant protein produced by a host cell.

15. The conjugate of claim 5, wherein said protein is a green fluorescent protein.

16. The conjugate of claim 5, wherein said protein is a lysosomal protein.

17. The conjugate of claim 1, wherein said lysosomal protein is a glucocerebrosidase.

18. A conjugate comprising a single α-galactosidase protein and a saccharide moiety being covalently linked to said α-galactosidase protein via a non-hydrophobic linker, said linker being a non-saccharide linker and comprising a poly(alkylene glycol) of at least 18 atoms in length, and said saccharide moiety being a monosaccharide.

19. The conjugate of claim 16, wherein said saccharide is M6P.

20. The conjugate of claim 9, wherein said sialic acid is N-acetylneuraminic acid.

21. The conjugate of claim 20, wherein said protein is a follicle-stimulating hormone (FSH).

22. The conjugate of claim 1, wherein an uptake of said conjugate into cells is at least 10% higher than an uptake of said protein into said cells.

23. A process of preparing the conjugate of claim 1, the process comprising reacting a glycosylation reagent, which comprises said saccharide moiety having attached thereto a non-hydrophobic linker having a reactive group, with said lysosomal protein, said linker being a non-saccharide linker and comprising a poly(alkylene glycol) of at least 18 atoms in length, and said saccharide moiety being a M6P.

24. The process of claim 23, wherein said reactive group is selected from the group consisting of an amine, a maleimide and a carboxylate.

25. A pharmaceutical composition comprising the conjugate of claim 1 and a pharmaceutically acceptable carrier.

26. A method of fluorescently labeling a saccharide-binding receptor in a cell, the method comprising contacting the cell with the conjugate of claim 15, wherein said receptor is capable of binding said monosaccharide, thereby fluorescently labeling the saccharide-binding receptor.

27. A method of treating a protein-related disease or disorder in a subject in need thereof, the method comprising administering to the subject a therapeutically effective amount of the conjugate of claim 1, thereby treating the protein-related disease or disorder.

28. The method of claim 27, wherein said protein is a lysosomal protein and said protein-related disease or disorder is a metabolic disease.

29. The method of claim 28, wherein said disease is a lysosomal storage disease.

30. The method of claim 27, wherein said protein-related disease is associated with a deficiency of said at least one protein.

31. The conjugate of claim 4, wherein said poly(alkylene glycol) is from 24 to 36 atoms in length.

32. The conjugate of claim 4, wherein said poly(ethylene glycol) comprises from 8 to 12 ethylene glycol units.

33. The conjugate of claim 1, wherein said lysosomal protein is an α-galactosidase.

34. The conjugate of claim 5, wherein said protein is an α-galactosidase.

35. The conjugate of claim 6, wherein said protein is an α-galactosidase.

36. The conjugate of claim 6, wherein said saccharide is M6P.

37. The conjugate of claim 18, wherein said poly(alkylene glycol) is from 24 to 36 atoms in length.

38. The conjugate of claim 18, wherein said poly(alkylene glycol) comprises poly(ethylene glycol), said poly(ethylene glycol) comprising from 8 to 12 ethylene glycol units.

39. The conjugate of claim 18, wherein said saccharide is M6P.

40. A method of fluorescent labeling lysosomes in a cell, the method comprising contacting the cell with the conjugate of claim 1, wherein said protein is a green fluorescent protein, thereby fluorescently labeling the lysosomes.

41. A method of treating a protein-related disease or disorder in a subject in need thereof, the method comprising administering to the subject a therapeutically effective amount of the conjugate of claim 5, thereby treating the protein-related disease or disorder.

42. A method of treating a protein-related disease or disorder in a subject in need thereof, the method comprising administering to the subject a therapeutically effective amount of the conjugate of claim 6, thereby treating the protein-related disease or disorder.

43. A method of treating a protein-related disease or disorder in a subject in need thereof, the method comprising administering to the subject a therapeutically effective amount of the conjugate of claim 18, thereby treating the protein-related disease or disorder.

* * * * *